(12) United States Patent
Zhang et al.

(10) Patent No.: US 10,980,809 B2
(45) Date of Patent: Apr. 20, 2021

(54) UREA-SUBSTITUTED AROMATIC RING-LINKED DIOXANE-QUINAZOLINE AND -LINKED DIOXANE-QUINOLINE COMPOUNDS, PREPARATION METHOD THEREFOR AND USE THEREOF

(71) Applicant: BEIJING SCITECH-MQ PHARMACEUTICALS LIMITED, Beijing (CN)

(72) Inventors: Qiang Zhang, Beijing (CN); Hongbo Zhang, Beijing (CN); Leifu Yang, Beijing (CN); Hailong Yang, Beijing (CN); Likai Zhou, Beijing (CN); Nanqiao Zheng, Beijing (CN); Shannan Yu, Beijing (CN); Zhongxiang Wang, Beijing (CN); Shouye Feng, Beijing (CN); Zhanqiang Xu, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 0 days.

(21) Appl. No.: 16/489,989

(22) PCT Filed: Feb. 11, 2018

(86) PCT No.: PCT/CN2018/076232
§ 371 (c)(1),
(2) Date: Aug. 29, 2019

(87) PCT Pub. No.: WO2018/157730
PCT Pub. Date: Sep. 7, 2018

(65) Prior Publication Data
US 2020/0061065 A1 Feb. 27, 2020

(30) Foreign Application Priority Data

Mar. 1, 2017 (CN) .......................... 201710117662.0
Mar. 17, 2017 (CN) .......................... 201710161891.2

(51) Int. Cl.
*A61K 31/517* (2006.01)
*A61P 35/00* (2006.01)
*A61K 31/4741* (2006.01)
*C07D 491/056* (2006.01)

(52) U.S. Cl.
CPC ........ *A61K 31/517* (2013.01); *A61K 31/4741* (2013.01); *A61P 35/00* (2018.01); *C07D 491/056* (2013.01)

(58) Field of Classification Search
CPC .............. C07D 491/056; A61K 31/517; A61K 31/519; A61P 35/00
See application file for complete search history.

(56) References Cited

U.S. PATENT DOCUMENTS

2011/0118245 A1    5/2011  Abraham et al.

FOREIGN PATENT DOCUMENTS

| CN | 1543459 A | 11/2004 |
| CN | 102026985 A | 4/2011 |
| CN | 102311395 A | 1/2012 |
| CN | 102532042 A | 7/2012 |
| CN | 104530063 A | 4/2015 |
| CN | 105837586 A | 8/2016 |
| CN | 105884699 A | 8/2016 |
| EP | 1566379 A1 | 8/2005 |
| EP | 1949902 A1 | 7/2008 |
| WO | 2014/127214 A1 | 8/2014 |

OTHER PUBLICATIONS

Zawilska. Pharmacological Reports, 2013, 65, 1-14. (Year: 2013).*
Karoulia, Nature Reviews: Cancer, 2017, 17, 676-691. (Year: 2017).*
Fan. European Journal of Medicinal Chemistry, 2019, 175, 349-356 (Year: 2019).*
BLACK. Journal of Chemical Education, 1990, 67(2), 141-142 (Year: 1990).*
International Search Report and Written Opinion for Application No. PCT/CN2018/076232, dated Apr. 23, 2018, 7 pages.
Zhang et al., Design and discovery of 4-anilinoquinazoline-urea derivatives as dual TK inhibitors of EGFR and VEGFR-2. Eur J Med Chem. Jan. 5, 2017;125:245-254.

* cited by examiner

*Primary Examiner* — Noble E Jarrell
(74) *Attorney, Agent, or Firm* — McCarter & English, LLP; Xin Zhang

(57) ABSTRACT

The present invention relates to a urea-substituted aromatic ring-linked dioxinoquinazoline and a urea-substituted aromatic ring-linked dioxinoquinoline of Formula (I), or a pharmaceutically acceptable salt thereof or a hydrate thereof. Also provided are the preparation of the compound as shown in Formula (I) and the pharmaceutically acceptable salt thereof and the use thereof as a drug. The drug is used as an inhibitor of tyrosine kinases (e.g., VEGFR-2, C-RAF, B-RAF) for treating tyrosine kinase-related diseases.

Formula (I)

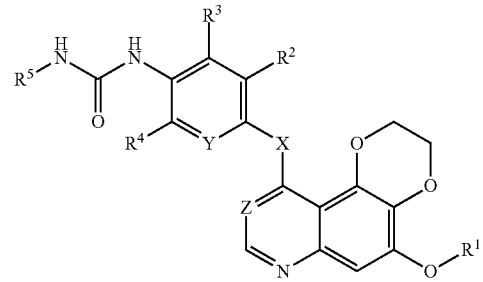

21 Claims, No Drawings

UREA-SUBSTITUTED AROMATIC RING-LINKED DIOXANE-QUINAZOLINE AND -LINKED DIOXANE-QUINOLINE COMPOUNDS, PREPARATION METHOD THEREFOR AND USE THEREOF

CROSS REFERENCE TO RELATED APPLICATIONS

The present application is a national application of PCT/CN2018/076232 filed on Feb. 11, 2018, which claims the priority of the Chinese Patent Application No. 201710117662.0 filed on Mar. 1, 2017, and the Chinese Patent Application No. 201710161891.2 filed on Mar. 17, 2017. The Chinese Patent Application No. 201710117662.0 and No. 201710161891.2 are incorporated herein by reference as part of the disclosure of the present application.

TECHNICAL FIELD

The present disclosure relates to a urea-substituted aromatic ring-linked dioxinoquinazoline and dioxinoquinoline compound, preparation method thereof and application thereof, and belongs to the technical field of medicinal chemistry.

BACKGROUND OF THE INVENTION

VEGF (vascular endothelial growth factor) must present for neovascularization and angiogenesis. During embryogenesis, the formation of blood vessels is divided into two stages, neovascularization and angiogenesis. Neovascularization is the differentiation of primitive progenitor cells into endothelial cells; and angiogenesis is the outgrowth of the nascent capillaries from the existing blood vessels in the form of budding. In normal adult mammals, there is only one type of blood vessels formation, i.e., angiogenesis, decomposition of local basement membrane around endothelial cells, and invasion of endothelial cells into the matrix. Such invasion is accompanied by the proliferation of endothelial cells, forming a migration column of endothelial cells that changes shape and forms a ring with each other. Thus, the new blood vessel cavity is formed.

VEGF is also essential for the angiogenesis of tumor tissues, and vascular endothelial growth factor A (VEGFA) and vascular endothelial growth factor receptor 2 (VEGFR-2) signaling pathways play the most important role, affecting the proliferation, survival, budding, migration of endothelial cells in tumor tissues, as well as affecting the permeability of tumor blood vessels. Endothelial cells without VEGF protein stimulation can also rely on autocrined VEGF proteins to maintain their integrity and survival. Vascular endothelial growth factor C (VEGFR-C)/vascular endothelial growth factor D (VEGF-D) mediates lymphangiogenesis in tumor tissues and promotes the metastasis of tumor tissues. Therefore, the development of drugs targeting angiogenesis have become a hot spot.

Bevacizumab is a 93% humanized murine VEGF monoclonal antibody, capable of binding to all subtypes of human VEGF A, blocks the VEGF/VEGFR signaling pathway, and inhibits tumor angiogenesis. In 2004, bevacizumab (trade name Avastin) was approved by FDA for selling in the United States, and became the first anti-tumor angiogenesis drug as the first-line drugs for the treatment of metastatic colorectal cancer used in combination with chemotherapeutic drugs. Bevacizumab could improve the abnormal tumor blood vessels, making them normalized and assisting chemotherapy drugs to reach tumor tissues. Due to the apoptosis mechanism induced by radiotherapy and chemotherapy, the hypoxic partial pressure in tumor tissues induces the expression of VEGF, and thus the combination of bevacizumab and chemoradiotherapy drugs effectively prevents such secondary reactions.

To date, there are nine drugs targeting VEGFR-2/KDR: sorafenib, sunitinib, pazopanib, axitinib, vandetanib, regorafenib, lenvatinib, nintedanib and Cediranib (AZD2171), which have been approved by the FDA for the treatment of cancer.

Lenvatinib, trade name Lenvima, is a drug for thyroid cancer developed by Eisai Corporation, Japan, which has specific inhibitory effects on VEGFR-1, VEGFR-2 and VEGFR-3, and also inhibits PDGFRP3 and FGFR-1. It is a class of TKI that selectively targets multiple receptors. With a similar mechanism to sorafenib, it inhibits neovascularization by inhibiting VEGFR-1, 2, 3 and PDGFR on one hand, and directly inhibits tumor cell proliferation by inhibiting FGFR-1 on the other hand. In 2015, the FDA approved Lenvatinib for the treatment of thyroid cancer.

B-RAF is a kind of tyrosine kinase receptor, and its abnormal activation plays an important role in the occurrence and development of various malignant tumors. In most cases, abnormal activation of B-RAF is caused by gene mutations. B-RAF belongs to the proto-oncogene. Studies have shown that more than 30 types of B-RAF gene mutations are associated with cancer, especially the V600E gene mutation. Mutations in the B-RAF gene usually cause two diseases. First, mutations can be inherited and cause birth defects. Second, as oncogenes, inherited mutations can lead to cancer in future life. B-RAF gene mutations have been found in many cancer tissues, including melanoma, colon cancer, thyroid cancer, non-small cell lung cancer, and glioma.

Sorafenib, trade name Nexavar, is a drug developed by Onyx Pharmaceuticals of the United States and Bayer AG of Germany, targeting the RAF/MEK/ERK signaling pathway, which mainly inhibits C-RAF and B-RAF, and also inhibits the activities of VEGFR-2, VEGFR-3, PDGFR-β, Flt-3, and c-Kit receptors. It can effectively inhibit tumor cell proliferation and angiogenesis in preclinical experiments. In a phase III clinical trial of metastatic renal cell carcinoma, sorafenib significantly increased the overall survival of the patient. In July of 2005, sorafenib was approved by the FDA as a drug for the treatment of advanced renal cell carcinoma.

There are many advantages for multi-targets inhibitors similar to Lenvatinib and Sorafenib, and research on such type of inhibitors is also a hot spot. However, currently, there are still very few similar drugs on the market, with limited availability, and the drugs on the market are subject to drug resistance and side effects. Therefore, such multi-targets small molecule inhibitor will have better therapeutic effects and application prospects compared to the existing single-target inhibitors on the market.

SUMMARY OF THE INVENTION

In view of the deficiencies of the prior art, the present disclosure provides a compound of Formula (I), or pharmaceutically acceptable salts, isomers, hydrates, solvates, or prodrugs thereof, Formula (I)

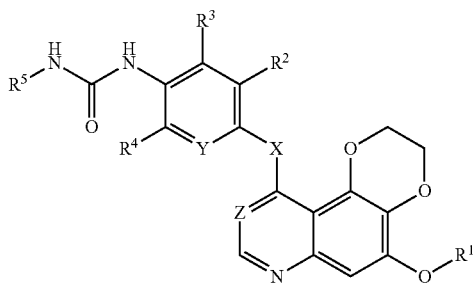

in the Formula (I),
X is O or NH;
Y is N or CH;
Z is N or CH;
$R^1$ is H, a $C_1$-$C_9$ alkyl, a $C_3$-$C_7$ cycloalkyl, a 4-7 membered heterocyclyl, a $C_1$-$C_6$ alkyl substituted by $C_3$-$C_7$ cycloalkyl, a $C_1$-$C_6$ alkyl substituted by 4-7 membered heterocyclyl, or a substituted $C_1$-$C_9$ alkyl, and the substituents in the substituted $C_1$-$C_9$ alkyl are one or more of the following groups consist of hydroxyl, $C_1$-$C_6$ alkoxyl, $C_1$-$C_6$ alkylthio group, amino group substituted by one or two $C_1$-$C_6$ alkyl, and unsubstituted amino group,
the said 4-7 membered heterocyclyl is a 4-7 membered heterocyclyl containing 1-2 atoms selected from N, O, and S, and the 4-7 membered heterocyclyl is unsubstituted or substituted by $C_1$-$C_6$ alkyl, $C_1$-$C_3$ acyl, or is oxidized by one to two oxygen atoms;
$R^2$ is H or halogen;
$R^3$ is H or halogen;
$R^4$ is H or halogen;
$R^5$ is H, $C_1$-$C_9$ alkyl, $C_3$-$C_8$ cycloalkyl, $C_1$-$C_6$ alkyl substituted by $C_3$-$C_8$ cycloalkyl, or substituted or unsubstituted aryl or heteroaryl, and the substituents of the substituted aryl or heteroaryl are one or more of the following groups consist of $C_1$-$C_3$ alkyl, $C_1$-$C_3$ alkoxyl, $C_1$-$C_3$ alkylthio group, amino group substituted by one or two $C_1$-$C_3$ alkyl or unsubstituted amino group, halogen, trifluoromethyl, aryloxy, or methylsulfonyl; and
the heteroaryl is a monocyclic or bicyclic group having 5 to 10 ring atoms, and containing 1-3 atoms selected from N, O, and S in the ring.

In a preferred embodiment, $R^1$ is H, $C_1$-$C_6$ alkyl, $C_3$-$C_6$ cycloalkyl, 5-6 membered heterocyclyl, $C_1$-$C_3$ alkyl substituted by $C_3$-$C_6$ cycloalkyl, $C_1$-$C_3$ alkyl substituted by 5-6 membered heterocyclyl, or substituted $C_1$-$C_6$ alkyl, and the substituents in the substituted $C_1$-$C_6$ alkyl are one or more of the following groups consist of hydroxyl, $C_1$-$C_3$ alkoxyl, $C_1$-$C_3$ alkylthio group, amino group substituted by one or two $C_1$-$C_3$ alkyl, and unsubstituted amino group,
the said 5-6 membered heterocyclyl is a 5-6 membered heterocyclyl having 1-2 atoms selected from N, O, and S, and the 5-6 membered heterocyclyl is unsubstituted or substituted by $C_1$-$C_3$ alkyl, $C_1$-$C_3$ acyl, or is oxidized by one or two oxygen atoms.

In a preferred embodiment, $R^1$ is selected from the groups consisting of: H, methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholinyl)-4-ethyl, (1,1-dioxothiomorpholinyl)-4-propyl, methylthioethyl, methylthiopropyl, dimethylaminoethyl, dimethylaminopropyl, dimethylaminobutyl, diethylaminoethyl, diethylaminopropyl, hydroxyethyl, hydroxypropyl, hydroxybutyl, hydroxypentyl, hydroxyhexyl, aminoethyl, aminopropyl, aminobutyl, 2-methyl-2-hydroxypropyl, 3-methyl-3-hydroxybutyl, (3S)-3-aminobutyl, (3R)-3-aminobutyl, (3S)-3-hydroxybutyl, or (3R)-3-hydroxybutyl.

In a preferred embodiment, the halogen in $R^2$, $R^3$, $R^4$ is F, Cl or Br.

In a preferred embodiment, $R^5$ is H, $C_1$-$C_6$ alkyl, $C_3$-$C_6$ cycloalkyl, $C_1$-$C_3$ alkyl substituted by $C_3$-$C_6$ cycloalkyl, or substituted or unsubstituted aryl or heteroaryl, and the substituents of the substituted aryl or heteroaryl are one or more of the following groups consist of $C_1$-$C_3$ alkyl, $C_1$-$C_3$ alkoxyl, $C_1$-$C_3$ alkylthio group, amino group substituted by one or two $C_1$-$C_3$ alkyl or unsubstituted amino group, halogen, trifluoromethyl, aryloxy and methylsulfonyl;
the heteroaryl is a monocyclic or bicyclic group having 5-10 ring atoms, and containing 1-2 ring atoms selected from N, O, and S in the ring.

In a preferred embodiment, $R^5$ is H, $C_1$-$C_6$ alkyl, $C_3$-$C_6$ cycloalkyl, $C_1$-$C_3$ alkyl substituted by $C_3$-$C_6$ cycloalkyl, or substituted or unsubstituted phenyl, naphthyl or heteroaryl, wherein the substituents of phenyl, naphthyl or heteroaryl are one or more of the following groups consist of methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluoro, chloro, bromo, trifluoromethyl, phenoxy, and methylsulfonyl;
the heteroaryl is selected from the groups consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

In a preferred embodiment, $R^5$ is selected from the groups consisting of H, methyl, ethyl, propyl, isopropyl, isopentyl, cyclopropyl, cyclobutyl, cyclopentyl, cyclohexyl, phenyl, 2-methoxyphenyl, 3-methoxyphenyl, 4-methoxyphenyl, 2-fluorophenyl, 3-fluorophenyl, 4-fluorophenyl, 4-phenoxyphenyl, 3-(methylsulfonyl)phenyl, 4-(methylsulfonyl)phenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-trifluoromethyl-4fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-trifluoromethyl-4-chlorophenyl, 2-chloro-4-fluorophenyl, 2-chloro-5-fluorophenyl, 3-chloro-4-fluorophenyl, pyridin-2-yl, pyridin-3-yl, pyridin-4-yl, 2-methoxy-pyridin-4-yl, 3-methyl-isoxazol-5-yl, and naphthalen-1-yl.

The present disclosure also provides a salt of the compounds represented by Formula (I), wherein the salt is an acidic/anionic salt or a basic/cationic salt; a pharmaceutically acceptable acidic/anionic salt is usually in the form in which the basic nitrogen is protonated by an inorganic or organic acid; representative organic or inorganic acids include hydrochloric acid, hydrobromic acid, hydroiodic acid, perchloric acid, sulfuric acid, nitric acid, phosphoric acid, formic acid, acetic acid, propionic acid, glycolic acid, lactic acid, succinic acid, maleic acid, tartaric acid, malic acid, citric acid, fumaric acid, gluconic acid, benzoic acid, mandelic acid, methanesulfonic acid, isethionic acid, benzenesulfonic acid, oxalic acid, palmitic acid, 2-naphthalenesulfonic acid, p-toluenesulfonic acid, cyclohexylsulfamic acid, salicylic acid, hexonic acid, trifluoroacetic acid. Pharmaceutically acceptable basic/cationic salts include but are not limited to salts of aluminum, calcium, chloroprocaine, choline, diethanolamine, ethylenediamine, lithium, magnesium, potassium, sodium and zinc.

In one embodiment of the present disclosure, provided herein is a method of preparing the compounds represented by Formula (I), or pharmaceutically acceptable salts, isomers, hydrates, solvates, or prodrugs thereof, comprising the preparation of the compounds of Formula (I) from the reaction of the compounds of Formula (II) and $H_2N-R^5$, wherein, X, Y, Z, $R^1$, $R^2$, $R^3$, $R^4$, and $R^5$ are as defined above,

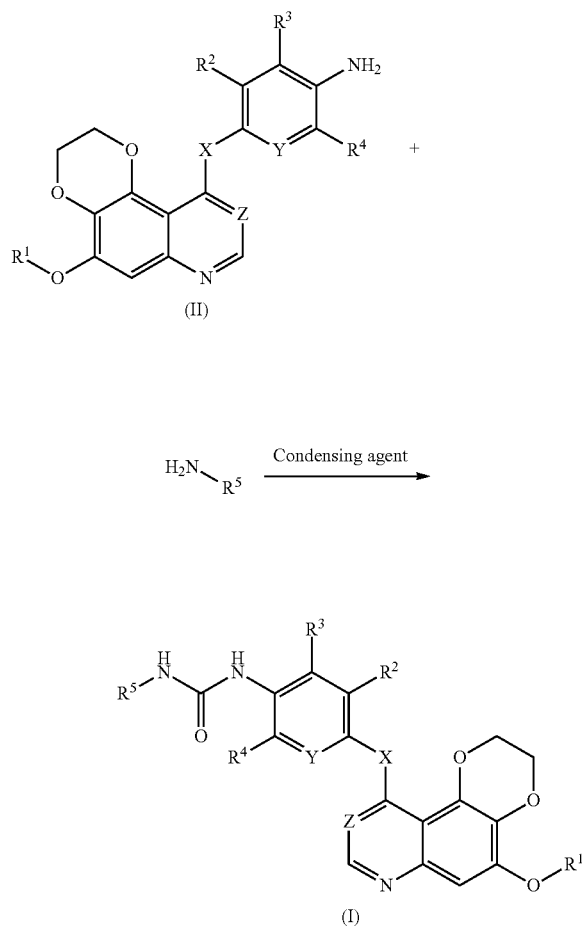

In another embodiment of the present disclosure, provided herein is a method of preparing the compounds represented by Formula (I), or pharmaceutically acceptable salts, isomers, hydrates, solvates, or prodrugs thereof, comprising the preparation of the compounds of Formula (I) from the reaction of the compounds of Formula (II') and the compounds of Formula (III), wherein, X, Y, Z, $R^1$, $R^2$, $R^3$, $R^4$, and $R^5$ are as defined above,

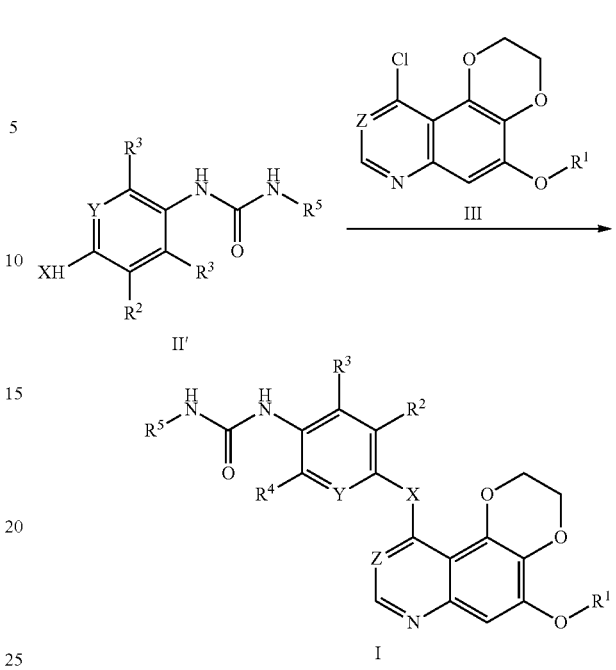

DETAILED DESCRIPTION

The term "substituted" as used herein, includes multiple substituents (e.g., phenyl, aryl, heteroalkyl, heteroaryl), preferably 1 to 5 substituents, more preferably 1 to 3 substituents, most preferably 1 or 2 substituents, independently selected from the list of substituents.

Unless otherwise specified, alkyl includes saturated linear and branched hydrocarbon group, $C_1$-$C_9$ represents the number of carbon atoms of an alkyl is 1-9. Similarly, for example, $C_1$-$C_3$ represents the number of carbon atoms of an alkyl is 1-3, e.g., $C_1$-$C_6$ alkyl includes methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl, and 2-methylpentyl. Alkoxyl is an alkylether consisting of a linear or branched chain as previously described. Similarly, alkenyl and alkynyl groups include linear or branched alkenyl or alkynyl groups.

Cycloalkyl refers to a cyclic group formed by carbon atoms. For example, $C_3$-$C_7$ represents an cycloalkyl group having 3 to 7 carbon atoms, including cyclopropyl, cyclobutyl, cyclopentyl, cyclohexyl, and cycloheptyl. Similarly, cyclic alkenyl group is also included herein.

The term "aryl" as used herein, unless otherwise specified, refers to an unsubstituted or substituted aromatic group, such as phenyl, naphthyl, anthracenyl. The term "aroyl" refers to —C(O)-aryl.

"Oxidized by one or two oxygen atoms" refers to a sulfur atom oxidized by one oxygen atom to form a double bond between the sulfur and oxygen, or oxidized by two oxygen atoms to form double bonds between the sulfur and two oxygen atoms.

The term "heterocyclyl" as used herein, unless otherwise specified, represents an unsubstituted or substituted stable 3 to 8 membered monocyclic saturated ring system consisting of carbon atoms and 1 to 3 heteroatoms selected from N, O, and S, wherein the N, S heteroatoms can be optionally oxidized, and the N heteroatoms can also be optionally quaternized. The heterocyclic ring can be attached at any heteroatom or carbon atom to form a stable structure. Examples of such heterocyclyl rings include, but are not limited to, azetidinyl, pyrrolidinyl, tetrahydrofuranyl, tetrahydrothiazolyl, tetrahydropyranyl, morpholinyl, thiomorpholinyl, piperidinyl, piperazinyl, oxopiperazinyl, oxopiperidinyl, dioxolanyl, dioxanyl, tetrahydroimidazolyl, tetrahydrooxazolyl, thiamorpholinyl sulfoxide, thiomorpholine sulfone and oxadiazolyl.

The term "heteroaryl" as used herein, unless otherwise specified, represents an unsubstituted or substituted stable 5 or 6 membered monocyclic aromatic ring system, and may also represent unsubstituted or substituted 9 or 10-membered benzo-fused heteroaromatic ring system or a bicyclic heteroaromatic ring system consisting of carbon atoms and one to three heteroatoms selected from N, O, S, wherein the N, S heteroatoms may optionally be oxidized, and N heteroatoms may optionally be quaternized. Heteroaryl can be attached at any heteroatom or carbon atom to form a stable structure. Heteroaryl includes but is not limited to thienyl, furyl, imidazolyl, pyrrolyl, thiazolyl, oxazolyl, isoxazolyl, pyranyl, pyridinyl, piperazinyl, pyrimidinyl, pyrazinyl, pyridazinyl, pyrazolyl, thiadiazolyl, triazolyl, indolyl, azaindolyl, indazolyl, azaindazolyl, benzimidazolyl, benzofuryl, benzothienyl, benzoisoxazolyl, benzoxazolyl, benzopyrazolyl, benzothiazolyl, benzothiadiazolyl, benzotriazolyl, adeninyl, quinolinyl, or isoquinolinyl.

The term "carbonyl" refers to a C(O) group.

Whenever the terms "alkyl" or "aryl" or either of their prefix roots appear in the name of a substituent (eg, aralkyl, dialkylamino), it shall be interpreted to contain those limitations given for the above "alkyl" and "aryl". Designated numbers of carbon atoms (e.g., $C_1$-$C_6$) shall independently represent the number of carbon atoms in an alkyl moiety or an alkyl moiety in a larger substituent (wherein the alkyl group is the prefix root).

In a preferred embodiment of the present disclosure, provided herein is a compound of Formula (I), or an isomer, tautomer, solvate, hydrate thereof, and pharmaceutically acceptable salts thereof.

The disclosure also provides methods for preparing the corresponding compounds, wherein the compounds disclosed herein can be prepared using a variety of synthetic methods, including the methods described below. The compounds of the present disclosure, or pharmaceutically acceptable salts, isomers or hydrates thereof could be synthesized using the following methods and the known synthetic methods in the art of organic synthesis, or by variations of those methods as understood by those skilled in the art. The preferred methods include, but are not limited to, the methods described below.

In one embodiment, the compound of the present disclosure, or a pharmaceutically acceptable salt, isomer or hydrate thereof is prepared by the following method:

Scheme 1, wherein, X is N, Z is N, Y, $R^1$, $R^2$, $R^3$, $R^4$ and $R^5$ are as described above,

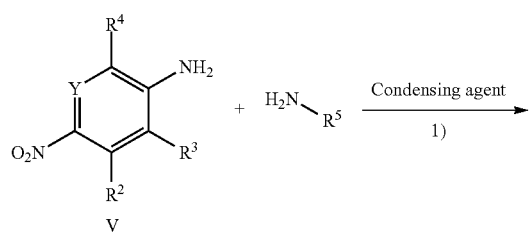

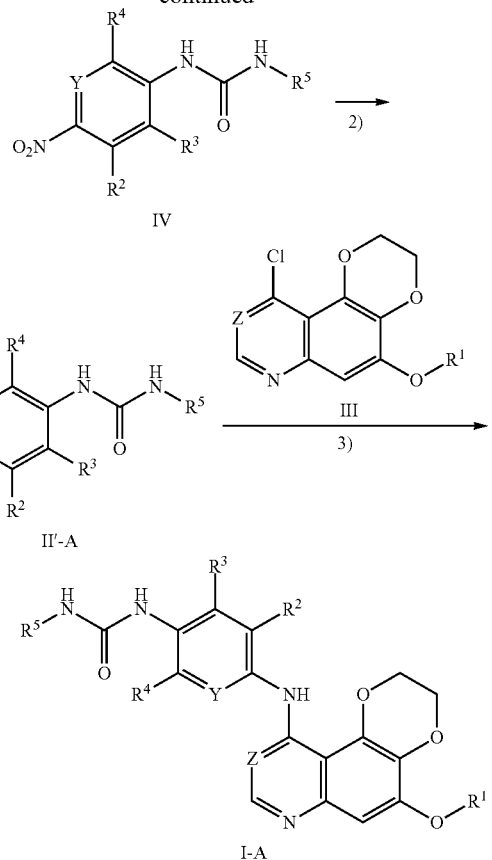

Reaction Conditions:

Step 1) the compound of the Formula (V) is reacted with $NH_2$—$R^5$ in the presence of a condensing agent to obtain a compound of the Formula (IV), preferably, the condensing agent includes, but is not limited to, triphosgene, carbonyl diimidazole, phenyl chloroformate, phenyl p-nitrochloroformate;

this reaction can also be carried out in the presence of a base. The base includes, but is not limited to, one of triethylamine, diisopropylethylamine, pyridine, 4-dimethylaminopyridine, 1,8-diazabicycloundec-7-ene or N-methylmorpholine, or a combination of two or more of the above bases; and the aprotic solvent includes, but is not limited to, one of dichloromethane, tetrahydrofuran, DMF, dioxane, dichloroethane, and a combination of two or more of the above agents;

preferably, step 1) is carried out in an aprotic solvent, including but not limited to one of dichloromethane, tetrahydrofuran, DMF, dioxane, dichloroethane, and a combination of two or more thereof.

Step 2) the compound represented by Formula (IV) is subjected to a nitro reduction reaction to obtain a compound of Formula (II'-A), and the nitro reduction can be conventionally carried out by a person skilled in the art;

preferably, the conditions of the nitro reduction reaction include, but are not limited to, hydrogen and Raney nickel, hydrogen and palladium on carbon, iron powder, zinc powder, and stannous chloride.

Step 3) a compound of Formula (II'-A) is reacted with a compound of Formula (III) in a base and an organic solvent to obtain a compound of Formula (I-A), the preferable reaction temperature in Step 3) is from room temperature to reflux temperature; the base is selected from one of sodium carbonate, potassium carbonate and cesium carbonate, or a combination of two or more thereof; and the organic solvent is selected from one of tetrahydrofuran, dioxane, isopropanol, ethanol, DMF, DMA, acetonitrile, DMSO or a combination of two or more thereof.

Scheme 2, wherein, X is O, Z is N, Y, $R^1$, $R^2$, $R^3$, $R^4$ and $R^5$ are as described above, Scheme 3, the compound of Formula (I), wherein, Z is CH, X, Y, $R^1$, $R^2$, $R^3$, $R^4$ and $R^5$ are as described above.

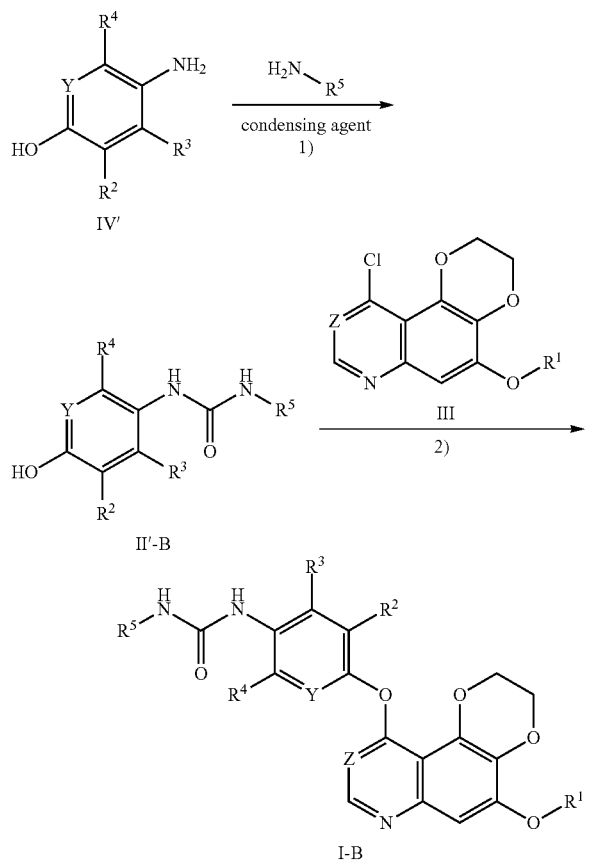

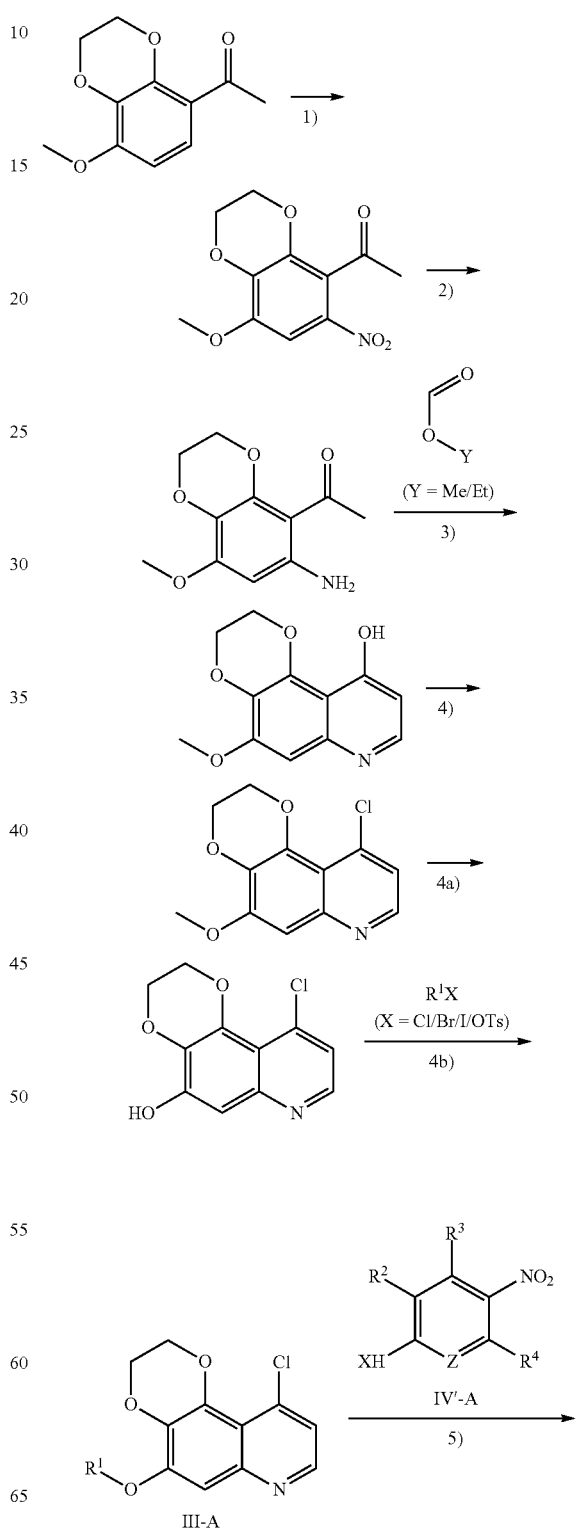

Reaction Conditions:

Step 1) the compound of Formula (IV') is reacted with the Formula $NH_2$—$R^5$ in the presence of a condensing agent to afford a compound of Formula (II'-B), preferably, the condensing agent comprises, but is not limited to, triphosgene, carbonyl diimidazole, phenyl chloroformate, and phenyl p-nitrochloroformate;

this reaction can also be carried out in the presence of a base. The base includes, but is not limited to, one of triethylamine, diisopropylethylamine, pyridine, 4-dimethylaminopyridine, 1,8-diazabicycloundec-7-ene or N-methylmorpholine or a combination of two or more thereof;

preferably, Step 1) is carried out in an aprotic solvent, including but not limited to one of dichloromethane, tetrahydrofuran, DMF, dioxane, dichloroethane, and a combination of two or more thereof.

Step 2) the compound of Formula (II'-B) is reacted with a compound of Formula (III) in a base and an organic solvent to give a compound of Formula (I-B);

the preferable reaction temperature in Step 2) is from room temperature to reflux temperature; the base is selected from one of sodium carbonate, potassium carbonate and

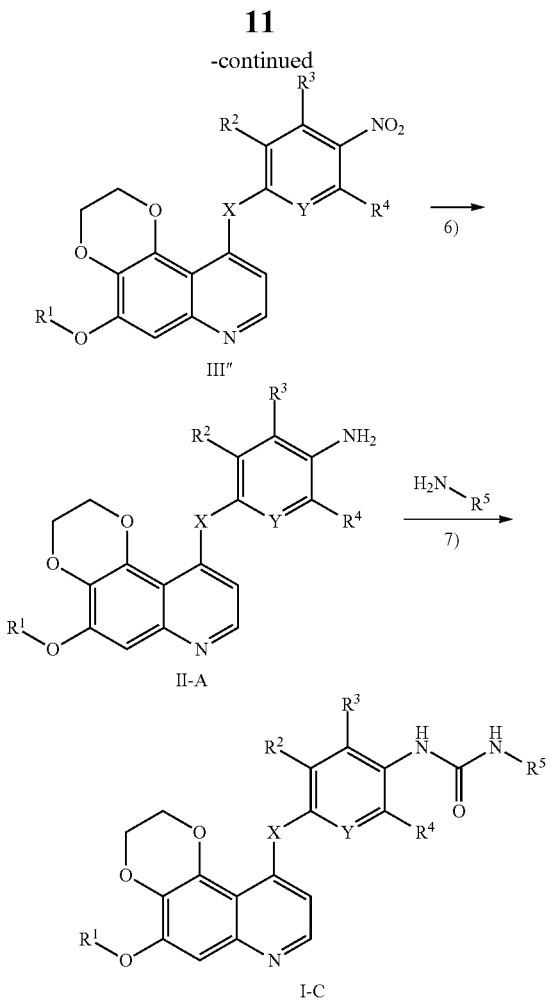

Reaction Conditions:

The nitrification conditions in step 1) are nitric acid and acetic acid.

Step 2) performing a nitro reduction reaction, and the nitro reduction can be conventionally carried out by a person skilled in the art;

preferably, the conditions of the nitro reduction reaction include, but are not limited to, hydrogen and Raney nickel, hydrogen and palladium on carbon, iron powder, zinc powder or stannous chloride.

In Step 3) 1-(8-methoxy-6-amino-2,3-dihydrobenzo[b][1,4]dioxin-5-yl)ethan-1-one is reacted with methyl formate or ethyl formate in an organic solvent, catalyzing by a base to give 10-hydroxy-5-methoxy-2,3-dihydro-[1,4]dioxino[2,3-f]quinoline, wherein the organic solvent includes, but is not limited to, one of ethylene glycol dimethyl ether, dioxane, tetrahydrofuran, tert-butanol, ethanol, methanol or a combination of two or more thereof; the base includes but is not limited to sodium t-butoxide, potassium t-butoxide, sodium methoxide, and sodium ethoxide; and the reaction can also be carried out under heating, and the temperature of the heating is from room temperature to reflux temperature.

In Step 4), 10-hydroxy-5-methoxy-2,3-dihydro-[1,4]dioxino[2,3-f]quinoline is reacted with a chlorinating reagent in an organic solvent to prepare 10-chloro-5-methoxy-2,3-dihydro-[1,4]dioxino[2,3-f]quinoline, wherein the chlorinating reagent is phosphorus oxychloride. The organic solvent includes, but is not limited to, one of benzene, toluene, chlorobenzene, and xylene or a combination of two or more thereof. The reaction can also be carried out in the presence of an organic base, which is triethylamine or diisopropyl ethylamine.

In Step 4a), 10-chloro-5-methoxy-2,3-dihydro-[1,4]dioxino[2,3-f]quinoline is converted to 5-hydroxy-10-chloro-2,3-dihydro-[1,4]dioxino[2,3-f]quinoline in an organic solvent under the action of a Lewis acid, wherein the Lewis acid is boron tribromide or boron trichloride; and the organic solvent is dichloromethane.

In Step 4b), the compound of Formula III-A is prepared from 5-hydroxy-10-chloro-2,3-dihydro-[1,4]dioxino[2,3-f]quinoline and $R^1X$ in an organic solvent, wherein $R^1$ is as defined in claims 1-3; the organic solvent includes, but is not limited to, one of tetrahydrofuran, dioxane, DMF, DMA, DMSO, acetonitrile or a combination of two or more thereof; and X in $R^1X$ is chlorine, bromine, iodine, mesylate, p-toluenesulfonate or triflate.

Step 5) the compound of Formula III-A is mixed with the compound of Formula IV'-A in an organic solvent and heated to 100° C. to 140° C. to obtain a compound of II-A. The organic solvent is selected from one of toluene, chlorobenzene, xylene, DMF, DMA, DMSO or a combination of two or more thereof.

Step 6) performing a nitro reduction reaction, and the nitro reduction can be routinely carried out by a person skilled in the art;

preferably, the conditions of the nitro reduction reaction include, but are not limited to, hydrogen and Raney nickel, hydrogen and palladium on carbon, iron powder, zinc powder, stannous chloride.

Step 7) the compound of Formula (II-A) is reacted with the Formula $NH_2$—$R^5$ in the presence of a condensing agent to obtain a compound of Formula (I-C);

preferably, the condensing agent includes, but is not limited to, triphosgene, carbonyl diimidazole, phenyl chloroformate, and phenyl p-nitrochloroformate;

this reaction can also be carried out in the presence of a base. The base includes, but is not limited to, one of triethylamine, diisopropylethylamine, pyridine, 4-dimethylaminopyridine, 1,8-diazabicycloundec-7-ene or N-methylmorpholine, or a combination of two or more thereof. The aprotic solvent includes, but is not limited to, one of dichloromethane, tetrahydrofuran, DMF, dioxane, dichloroethane, and a combination of two or more thereof.

Preferably, Step 7) is carried out in an aprotic solvent, including but not limited to one of dichloromethane, tetrahydrofuran, DMF, dioxane, dichloroethane, and a combination of two or more thereof;

when $R^1$ is —$CH_3$, Step 4a) and Step 4b) may be omitted, and the operation of Step 5) may be performed after the completion of Step 4).

The disclosure also provides a method for preparing the corresponding compounds, in particular by the methods described below.

The synthetic method of Intermediate (2) is as follows:

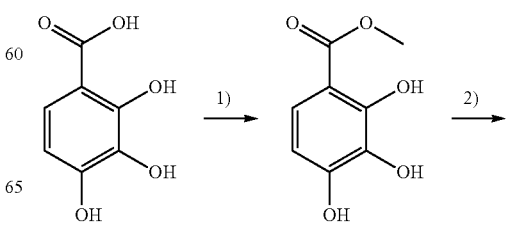

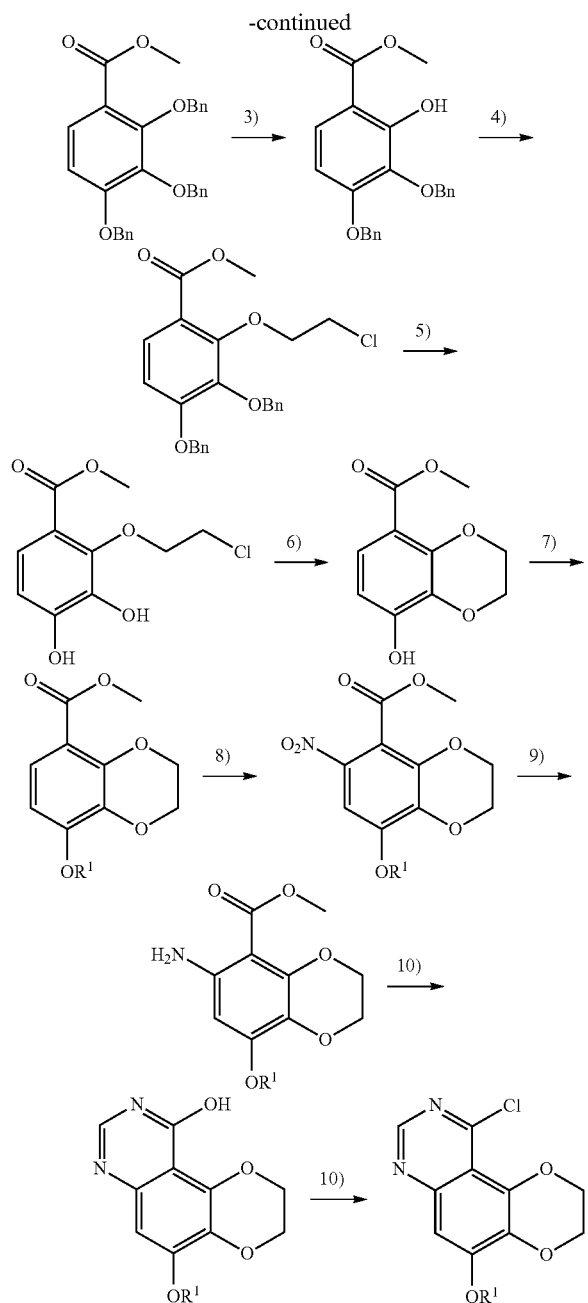

The synthetic method of Intermediate (2) is in accordance with the patent CN104530063.

It is apparent that the compounds of Formula I, the isomers, crystalline forms or prodrugs, and pharmaceutically acceptable salts thereof, may exist in both solvated and unsolvated forms. For example, the solvated form can be a hydrate form. The disclosure includes both solvated and unsolvated forms.

The compounds of the present disclosure may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound, separating the diastereomers and converting (e.g., hydrolyzing) the individual diastereomers to the corresponding pure enantiomers. All such isomers, including diastereomer mixtures and pure enantiomers are considered as part of the disclosure.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into a compound of Formula (I) of the present disclosure in vivo. Such transformation is affected by hydrolysis of the prodrug in the blood or enzymatic conversion to the parent compound in the blood or tissue.

Pharmaceutical compositions of this disclosure comprise a compound of the formula (I) described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyper proliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, including a method for administering to the subject a therapeutically effective amount of a composition containing the compound of the present disclosure.

The present disclosure also includes the use of a compound of the present disclosure, or a pharmaceutically acceptable derivative thereof, in the manufacture of a medicament for treating cancer (including non-solid tumors, solid tumors, primary or metastatic cancer, as indicated elsewhere herein and including one or more of other therapies to which the cancer is resistant or refractory), as well as other diseases (including, but not limited to, ocular fundus diseases, psoriasis, atheroma, pulmonary fibrosis, liver fibrosis, myelofibrosis, and the like). The cancer includes, but is not limited to any one of non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal interstitialoma, thyroid cancer, chronic granulocytic leukemia, acute myeloid leukemia, non-Hodgkin's lymphoma, nasopharyngeal carcinoma, esophageal cancer, brain tumor, B cell and T cell lymphoma, lymphoma, multiple myeloma, biliary cancer and sarcoma, and cholangiocarcinoma.

The present disclosure is better illustrated by the examples provided below, wherein all temperatures are in degrees Celsius unless otherwise stated.

DETAILED EMBODIMENTS

Preparation of Intermediates

Preparation of Intermediate 1)
2-chloro-4-nitroaniline

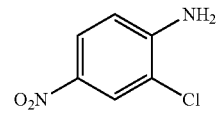 [SMILES: Nc1ccc([N+](=O)[O-])cc1Cl]

14 g (100 mmol) of the compound 4-nitroaniline, and 200 mL of isopropanol were added to a reaction vessel, which were stirred, and heated to 60° C., and 13.4 g (100 mmol) of N-chlorosuccinimide was added, and the temperature of the mixture was raised to 80° C., and stirred for half an hour. After the reaction was completed, the reaction mixture was cooled, poured into 2 L of ice water, stirred for half an hour, filtered, washed with water, and dried to give 16 g of a yellow solid, with a yield of 90%.

Preparation of Intermediate 2)
1-(2-chloro-4-nitrophenyl)-3-cyclopropylurea

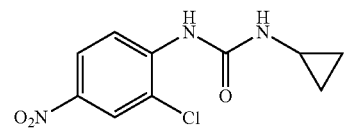 [SMILES: O=C(Nc1ccc([N+](=O)[O-])cc1Cl)NC1CC1]

173 mg (1 mmol) of 2-chloro-4-nitroaniline, 200 mg (0.67 mmol) of triphosgene, 10 mL of dichloromethane were added to a reaction vessel, which were stirred at 0° C. for 10 minutes, and 405 mg (4 mmol) of triethylamine was added dropwise. The reaction was continued at 0° C. for 2 hours, to which 114 mg (2 mmol) of cyclopropylamine was added dropwise, and stirred at room temperature for 15 hours. The reaction was completed, concentrated and recrystallized from methanol to yield 180 mg of a yellow solid, with a yield of 67%.

Preparation of Intermediate 3)
1-(4-aminophenyl)-3-cyclopropylurea

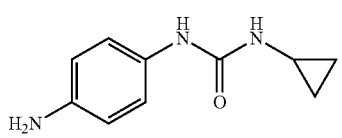 [SMILES: Nc1ccc(NC(=O)NC2CC2)cc1]

90 mg (0.35 mmol) of 1-(2-chloro-4-nitrophenyl)-3-cyclopropylurea, 10 mg wet palladium on carbon (5% purity, containing 55% water), and 10 mL methanol were added to a reaction vessel. The reaction system was pumped and purged with hydrogen for three times, and stirred at room temperature for 5 hours under 1 atm of a hydrogen atmosphere. The reaction was completed, filtered, and the filtrate was concentrated to give 60 mg of a light purple solid, with a yield of 90%. MS: 192[M+H]$^+$.

Preparation of Intermediate 4)
1-(4-amino-2-chlorophenyl)-3-cyclopropylurea

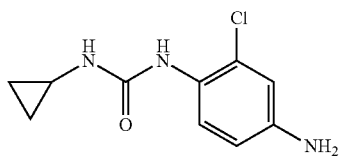 [SMILES: Nc1ccc(NC(=O)NC2CC2)c(Cl)c1]

90 mg (0.35 mmol) 1-(2-chloro-4-nitrophenyl)-3-cyclopropylurea, and 230 mg (4 mmol) zinc powder were added to a reaction kettle containing 15 mL of acetic acid, which were stirred at 60° C. for 2 hours. The reaction mixture was filtered, and the filtrate was concentrated to give a purple oil. The oil was dissolved into dichloromethane, and washed with saturated sodium bicarbonate and saturated brine sequentially. The organic phase was dried and concentrated to give 60 mg of a purple solid, with a yield of 76%. MS: 226[M+H]$^+$.

Preparation of Intermediate 5) 1-(2-chloro-4-nitrophenyl)-3-(3-methoxyphenyl)urea

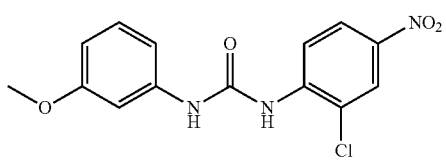 [SMILES: COc1cccc(NC(=O)Nc2ccc([N+](=O)[O-])cc2Cl)c1]

According to the operation for Intermediate 2), 200 mg 1-(2-chloro-4-nitrophenyl)-3-(3-methoxyphenyl)urea was obtained from 2-chloro-4-nitroaniline (173 mg, 1 mmol) and 3-methoxyaniline (250 mg, 2 mmol), with a yield of 68%.

$^1$HNMR (CD$_3$OD, 400 MHz) δ ppm: 3.81 (3H, s), 6.66 (1H, d, J=8.0 Hz), 6.96 (1H, d, J=8.0 Hz), 7.21 (1H, d, J=8.0 Hz), 7.25 (1H, s), 8.19 (1H, d, J=8.0 Hz), 8.35 (1H, s), 8.61 (1H, d, J=8.0 Hz). MS: 322[M+H]$^+$.

Intermediate 6)
1-(4-aminophenyl)-3-(3-methoxyphenyl)urea

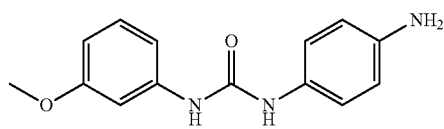 [SMILES: COc1cccc(NC(=O)Nc2ccc(N)cc2)c1]

According to the operation for Intermediate 3), 60 mg product was obtained from 1-(2-chloro-4-nitrophenyl)-3-(3-methoxyphenyl)urea (100 mg, 0.3 mmol) by reduction with hydrogen, with a yield of 75%, MS: 258[M+H]$^+$.

Preparation of Intermediate 7) 1-(4-amino-2-chlorophenyl)-3-(3-methoxyphenyl)urea

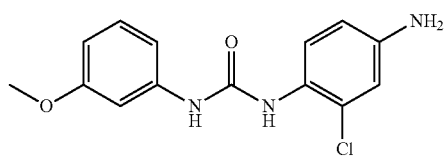

According to the operation for Intermediate 4), 70 mg product was obtained from 1-(2-chloro-4-nitrophenyl)-3-(3-methoxyphenyl)urea (100 mg, 0.3 mmol) by reduction with zinc powder, with a yield of 77%, MS: 292[M+H]$^+$.

Preparation of Intermediate 8) 1-(4-amino-2-chlorophenyl)-3(pyridin-2-yl)urea

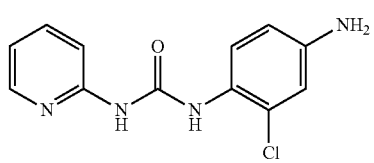 [SMILES: Nc1ccc(NC(=O)Nc2ccccn2)c(Cl)c1]

According to the operation for Intermediate 2), and 4), 160 mg target product was obtained from the reaction of 2-aminopyridine (94 mg, 1 mmol) and 2-chloro-4-nitroaniline (142 mg, 1 mmol), with a yield of 62% (two steps); MS: 263[M+H]$^+$.

Intermediate 9) 1-(4-amino-2-chlorophenyl)-3-(3-fluorophenyl)urea

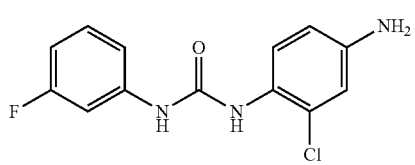 [SMILES: Nc1ccc(NC(=O)Nc2cccc(F)c2)c(Cl)c1]

According to the operation for Intermediate 2), and 4), 200 mg target product was obtained from the reaction of 3-fluoroaniline (111 mg, 1 mmo) and 2-chloro-4-nitroaniline (142 mg, 1 mmol), with a yield of 71% (two steps).

$^1$HNMR (CD$_3$OD, 400 MHz) δ ppm: 6.66 (1H, d, J=8.0 Hz), 6.80 (1H, s), 7.04 (2H, d, J=8.0 Hz), 7.41 (2H, d, J=8.0 Hz), 7.50 (1H, d, J=8.0 Hz), MS: 280[M+H]$^+$.

Intermediate 10) 1-(4-amino-2-chlorophenyl)-3-(3-methylisoxazol-5-yl)urea

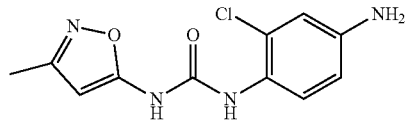 [SMILES: Cc1cc(NC(=O)Nc2ccc(N)cc2Cl)on1]

According to the operation for Intermediate 2), and 4), 220 mg target product was obtained from the reduction of the nitro substituted product, which was obtained by reacting 3-methylisoxazol-5-amine (98 mg, 1 mmol) and 2-chloro-4-nitroaniline (142 mg, 1 mmol), with zinc powder, with a yield of 84%;

$^1$HNMR (CD$_3$OD, 400 MHz) δ ppm: 2.39 (3H, s), 6.34 (1H, s), 6.65 (1H, d, J=8.0 Hz), 6.80 (1H, s), 7.51 (1H, d, J=8.0 Hz), MS: 267[M+H]$^+$.

Intermediate 11) 1-(4-nitro-2-chlorophenyl)-3-isopropylurea

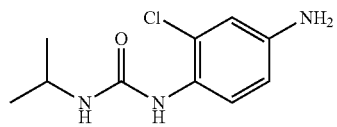

According to the operation for Intermediate 2), and 4), 215 mg nitro product was obtained from reacting isopropylamine (110 mg, 2 mmol) and 2-chloro-4-nitroaniline (142 mg, 1 mmol), with a yield of 86%. MS: 258[M+H]$^+$.

Intermediate 12) 1-(2-chloro-4-aminophenyl)-3-(2-methoxypyridin-4-yl)urea

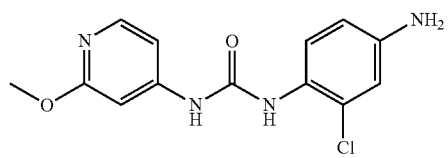 [SMILES: COc1cc(NC(=O)Nc2ccc(N)cc2Cl)ccn1]

According to the operation for Intermediate 2), and 4), 206 mg target product was obtained from the reduction of the nitro substituted product, which was obtained by reacting 2-methoxy-4-aminopyridine (124 mg, 1 mmol) and 2-chloro-4-nitroaniline (142 mg, 1 mmol), with zinc powder, with a yield of 70%;

$^1$HNMR (CD$_3$OD, 400 MHz) δ ppm: 3.80 (3H, s), 6.65 (1H, d, J=8.0 Hz), 6.79 (1H, s), 6.95 (1H, d, J=8.0 Hz), 7.07 (1H, s), 7.51 (1H, d, J=8.0 Hz), 7.93 (1H, s), MS: 293[M+H]$^+$.

Intermediate 13) 1-(4-amino-2-chlorophenyl)-3-(4-chloro-3-(trifluoromethyl)phenyl)urea

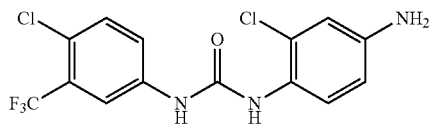 [SMILES: Nc1ccc(NC(=O)Nc2ccc(Cl)c(C(F)(F)F)c2)c(Cl)c1]

According to the operation for Intermediate 2), and 4), 250 mg target product was obtained from the reduction of the nitro substituted product, which was obtained by reacting 4-chloro-3-trifluoromethylaniline (200 mg, 1 mmol) and 2-chloro-4-nitroaniline (142 mg, 1 mmol), with zinc powder, with a yield of 73%, MS: 364[M+H]$^+$.

Intermediate 14) 1-(4-amino-2-chlorophenyl)-3-(2-fluoro-4-(trifluoromethyl)phenyl)urea

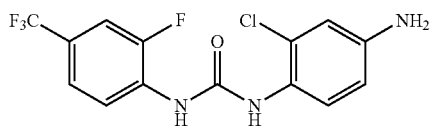 [SMILES: Nc1ccc(NC(=O)Nc2ccc(C(F)(F)F)cc2F)c(Cl)c1]

According to the operation for Intermediate 2), and 4), 208 mg target product was obtained from the reduction of the nitro substituted product, which was obtained by reacting 2-fluoro-4-(trifluoromethyl)aniline (180 mg, 1 mmol) and 2-chloro-4-nitroaniline (142 mg, 1 mmol), with zinc powder, with a yield of 65%, MS: 348[M+H]$^+$.

Intermediate 15) 1-(4-amino-2-chlorophenyl)-3-(4-(phenoxy)phenyl)urea

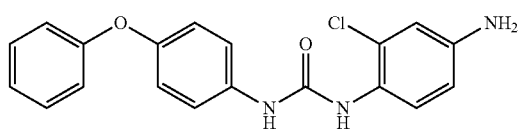 [SMILES: Nc1ccc(NC(=O)Nc2ccc(Oc3ccccc3)cc2)c(Cl)c1]

According to the operation for Intermediate 2), and 4), 235 mg target product was obtained from the reduction of the nitro substituted product, which was obtained by reacting 4-phenoxyaniline (185 mg, 1 mmol) and 2-chloro-4-nitroaniline (142 mg, 1 mmol), with zinc powder, with a yield of 72%, MS: 354[M+H]$^+$.

Intermediate 16) 1-(4-amino-2-chlorophenyl)-3-(3-(methylsulfonyl)phenyl)urea

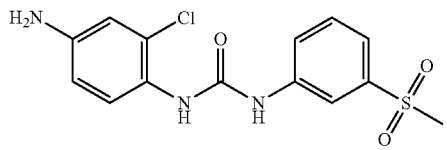 [SMILES: CS(=O)(=O)c1cccc(NC(=O)Nc2ccc(N)cc2Cl)c1]

According to the operation for Intermediate 2), and 4), 190 mg target product was obtained from the reduction of the nitro substituted product, which was obtained by reacting 3-(methylsulfonyl)aniline (170 mg, 1 mmol) and 2-chloro-4-nitroaniline (142 mg, 1 mmol), with zinc powder, with a yield of 61%, MS: 340[M+H]$^+$.

Preparation of Intermediate 17) 1-(4-chloro-3-(trifluoromethyl)phenyl)-3-(4-hydroxyphenyl)urea

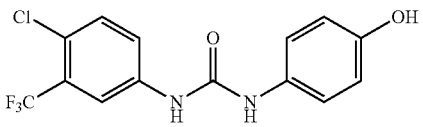 [SMILES: O=C(Nc1ccc(O)cc1)Nc1ccc(Cl)c(C(F)(F)F)c1]

300 mg triphosgene, 0.3 ml triethylamine, and 5 ml toluene were added in a reaction vessel, and 5 ml solution of toluene containing 490 mg 4-chloro-3-(trifluoromethyl)aniline was added dropwise thereto in an ice-water bath. After completion of the dropwise addition, the reaction was carried out in an ice-water bath for 1 h, and then for 2 hours after the temperature was raised to 80° C. After cooling, the solvent was evaporated to dryness and the residue was dissolved in 10 ml of dichloromethane. 270 mg 4-aminophenol was added, and the reaction was carried out overnight at room temperature. The reaction mixture was concentrated to give a purple solid, which was purified by column chromatography (Silica gel 200-300 mesh, the volume ratio of petroleum ether and ethyl acetate is 4:1), to obtain 530 mg of a grey solid, with a yield of 65%. MS: 331[M+H]$^+$.

Preparation of Intermediate 18) 1-(4-chloro-3-(trifluoromethyl)phenyl)-3-(2-fluoro-4-hydroxyphenyl)urea

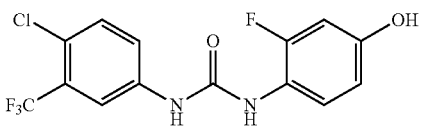 [SMILES: O=C(Nc1ccc(Cl)c(C(F)(F)F)c1)Nc1ccc(O)cc1F]

According to the operation for Intermediate 17), an off-white target compound was obtained from 4-chloro-3-(trifluoromethyl)aniline and 3-fluoro-4-aminophenol, with a yield of 72%. MS: 349[M+H]$^+$.

Preparation of Intermediate 19) 1-(2-fluoro-5-(trifluoromethyl)phenyl)-3-(4-hydroxyphenyl)urea

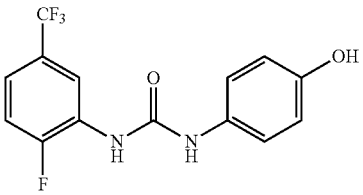 [SMILES: O=C(Nc1ccc(O)cc1)Nc1cc(C(F)(F)F)ccc1F]

According to the operation for Intermediate 17), a purple target compound was obtained from 2-fluoro-5-(trifluoromethyl)aniline and 4-aminophenol, with a yield of 82%. MS: 283[M+H]$^+$.

$^1$H NMR (DMSO-d$_6$, 400 MHz) δ 6.57-6.79 (2H, m), 7.18-7.28 (2H, m), 7.30-7.40 (1H, m), 7.42-7.58 (1H, m), 8.55-8.71 (1H, m), 8.80 (1H, d, J=3.0 Hz), 8.91 (1H, s), 9.18 (1H, s).

Preparation of Intermediate 20) 1-(2,4-difluorophenyl)-3 (2-fluoro-4-hydroxyphenyl)urea

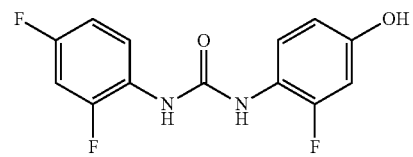 [SMILES: O=C(Nc1ccc(O)cc1F)Nc1ccc(F)cc1F]

According to the operation for Intermediate 17), an off-white target compound was obtained from 2,4-difluoroaniline and 3-fluoro-4-aminophenol, with a yield of 68%. MS: 283[M+H]$^+$.

Preparation of Intermediate 21) 1-(2-chloro-4-hydroxyphenyl)-3-cyclopropylurea

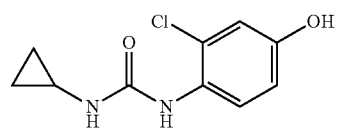 [SMILES: O=C(Nc1ccc(O)cc1Cl)NC1CC1]

0.3 ml pyridine, 300 mg 4-amino-3-chlorophenol hydrochloride, and 5 ml DMF were added in a reaction vessel. The mixture was reacted in an ice bath for 30 min. then, 0.3 ml phenyl chloroformate was added dropwise, and the reaction was carried out for 30 min. The reaction mixture was extracted with 1N HCl solution and ethyl acetate. The organic phase was washed, dried and concentrated. The concentrate was dissolved in 5 ml DMF, 0.3 ml cyclopropylamine was added, and the reaction was carried out overnight at room temperature. The reaction mixture was extracted with 1N HCl solution and ethyl acetate. The organic phase was washed with saturated NaCl solution, dried and concentrated to obtain 325 mg of a white powder, with a yield of 85%. MS: 227[M+H]$^+$.

Preparation of Intermediate 22) 1-(2-chloro-4-aminophenyl)-3-cyclohexylurea

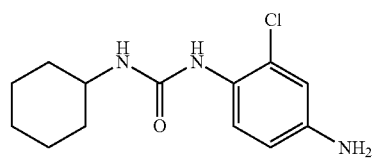 [SMILES: Nc1ccc(NC(=O)NC2CCCCC2)c(Cl)c1]

According to the operation for Intermediate 2) and 4), a pale yellow solid was obtained from the reaction of 2-chloro-4-nitroaniline and cyclohexylamine, with a yield of 56%, MS: 268[M+H]$^+$ Preparation of Intermediate 23) 1-(4-hydroxy-2-chlorophenyl)-3-(4-fluorophenyl)urea

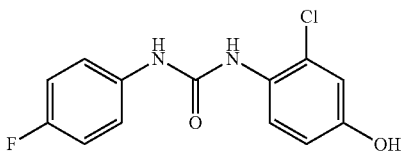

According to the operation for Intermediate 17), an off-white target compound was obtained from 4-fluoroaniline and 3-chloro-4-aminophenol, with a yield of 68%. MS: 281[M+H]$^+$.

Preparation of Intermediate 24) 1-(3-chloro-4-fluorophenyl)-3-(4-hydroxyphenyl)urea

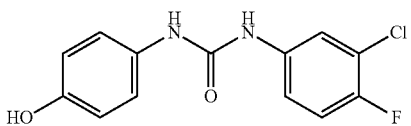 [SMILES: O=C(Nc1ccc(O)cc1)Nc1ccc(F)c(Cl)c1]

According to the operation for Intermediate 17), a white solid compound was obtained from the reaction of 4-aminophenol and 3-chloro-4-fluoroaniline, with a yield of 45%; $^1$H NMR (DMSO-d$_6$, 400 MHz) δ 6.65-6.72 (2H, m), 7.18-7.23 (2H, m), 7.29-7.32 (1H, m), 7.35-7.37 (1H, m), 7.67-7.71 (1H, m), 7.79-7.82 (1H, m), 8.57 (1H, s), 8.96 (1H, s), MS: 281 [M+H]$^+$.

Preparation of Intermediate 25) 1-(4-fluoro-3-(trifluoromethyl)phenyl)-3-(4-hydroxyphenyl)urea

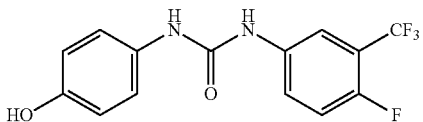 [SMILES: O=C(Nc1ccc(O)cc1)Nc1ccc(F)c(C(F)(F)F)c1]

According to the operation for Intermediate 17), a white solid compound was obtained from the reaction of 4-aminophenol and 4-fluoro-3-(trifluoromethyl)aniline, with a yield of 55%; 1H NMR (DMSO-d6, 400 MHz) δ 6.66-6.73 (2H, m), 7.17-7.26 (2H, m), 7.36-7.50 (2H, m), 7.56-7.64 (1H, m), 8.00-8.11 (1H, m), 8.63 (1H, s), 9.14 (1H, s); MS: 315[M+H]$^+$ Preparation of Intermediate 26) 1-(5-chloro-2-fluorophenyl)-3-(4-hydroxyphenyl)urea

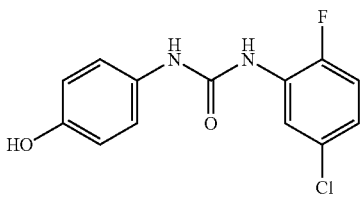 [SMILES: O=C(Nc1ccc(O)cc1)Nc1cc(Cl)ccc1F]

According to the operation for Intermediate 17), a white solid compound was obtained from the reaction of 4-aminophenol and 5-chloro-2-fluoroaniline, with a yield of 63%; 1H NMR (DMSO-d6, 400 MHz) δ 6.66-6.74 (2H, m), 6.98-7.05 (1H, m), 7.19-7.25 (2H, m), 7.25-7.32 (1H, m), 8.28-8.31 (1H, m), 8.65 (1H, s), 8.85 (1H, s), 9.16 (1H, s); MS: 281 [M+H]+

Preparation of Intermediate 27) 1-(4-hydroxyphenyl)-3-(naphthalen-1-yl)urea

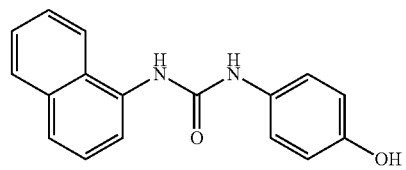 [SMILES: O=C(Nc1ccc(O)cc1)Nc1cccc2ccccc12]

According to the operation for Intermediate 21), a white solid compound was obtained from the reaction of 4-hydroxybenzene and naphthalen-1-amine, with a yield of 65%; MS: 279[M+H]$^+$ Synthetic Method of Intermediate 28) Preparation of 10-chloro-5-methoxy-2,3-dihydro-[1,4]dioxino[2,3-f]quinazoline

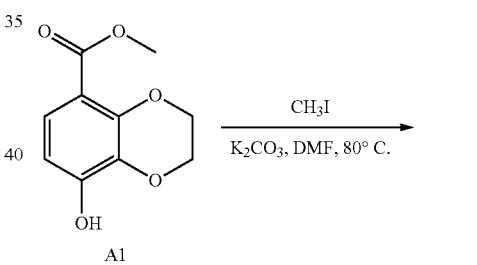

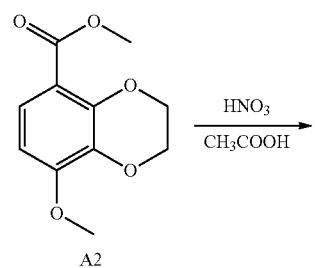

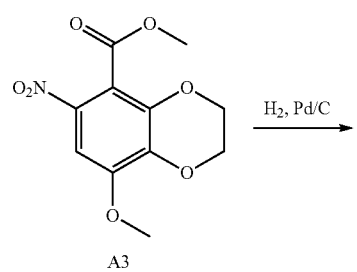

-continued

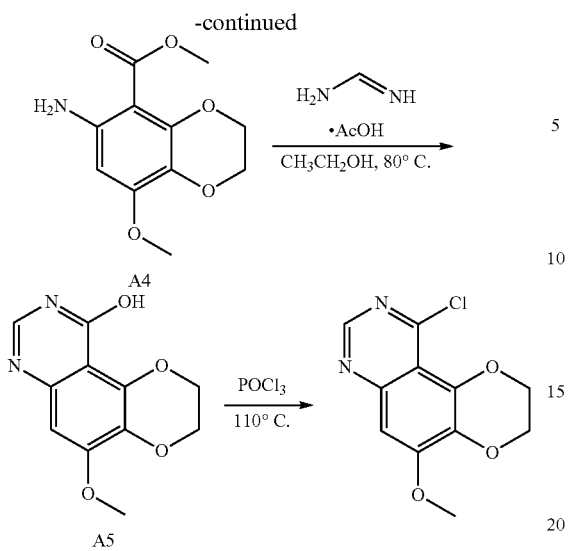

For detailed synthetic method for the Intermediate, see patent document No. CN104530063. Compound A1 was reacted with methyl iodide in a solution of potassium carbonate in N'N-dimethylformamide by heating to a temperature of 80° C. for 2 hours. The mixture was added to water, filtered and dried to obtain a white solid A2. A2 was dissolved in acetic acid, and at 0° C. the mixture of fuming nitric acid and acetic acid was added dropwise thereto, and after the dropwise addition is completed, the reaction mixture was reacted at 0° C. for one hour. The reaction mixture was poured into crushed ice and stirred, and filtered and dried to obtain a pale yellow solid A3. A3 was dissolved in methanol and the reaction was carried out for 1 hour with palladium on carbon under hydrogen atmosphere. The mixture was filtered, and the filtrate was concentrated to give a pale purple oil A4. Compound A4 and formamidine acetate were reacted under reflux in ethanol for 10 hours, and after cooled overnight, the reaction mixture was filtered and dried to give a pale gray solid A5. The Compound A5 was heated under reflux for 10 hours in phosphorus oxychloride. The reaction was completed, concentrated, and dichloromethane, crushed ice, and potassium carbonate were added thereto respectively, and the pH of the mixture was adjusted to 9. After extraction, the organic phase was washed with saturated brine and dried. Concentration provided the target product as a yellow solid, with a yield of 55%. MS: 253 [M+H]$^+$ Preparation of Intermediate 29: 10-chloro-5-((tetrahydro-2H-pyran-4-yl)oxy)-2,3-dihydro-[1,4]dioxino[2,3-f]quinazoline

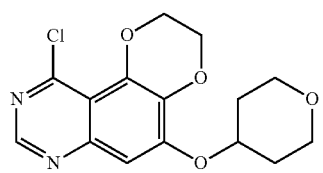 [SMILES: Clc1ncnc2cc(OC3CCOCC3)c3c(c12)OCCO3]

According to the same procedure as Intermediate 28), a yellow solid product was obtained, with a yield of 45%. MS: 323[M+H]$^+$ Preparation of Intermediate 30: 10-chloro-5-(2-methoxyethoxy)-2,3-dihydro-[1,4]dioxino[2,3-f]quinazoline

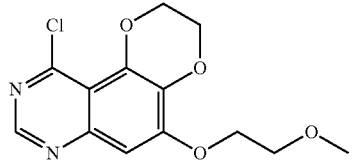 [SMILES: COCCOc1cc2ncnc(Cl)c2c2c1OCCO2]

According to the same procedure as Intermediate 28), a yellow solid product was obtained, with a yield of 60%. MS: 297[M+H]$^+$ Preparation of Intermediate 31: 10-chloro-5-(2-morpholinoethoxy)-2,3-dihydro-[1,4]dioxino[2,3-f]quinazoline

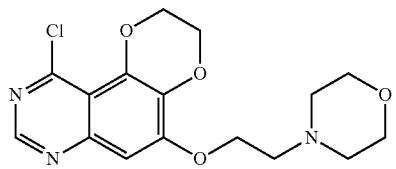 [SMILES: Clc1ncnc2cc(OCCN3CCOCC3)c3c(c12)OCCO3]

According to the same procedure as Intermediate 28), a yellow solid product was obtained, MS: 352[M+H]$^+$ $^1$H NMR (DMSO-d$_6$, 300 MHz) δ ppm: 3.16 (1H, d, J=5.0 Hz), 3.43 (4H, s), 3.71 (4H, d, J=5.1 Hz), 3.87 (1H, s), 4.29-4.55 (6H, m), 6.90 (1H, s), 8.38 (1H, d, J=2.9 Hz).

Preparation of Intermediate 32: 10-chloro-5-((2-tetrahydropyrrol-1-yl)ethoxy)-2,3-dihydro-[1,4]dioxino[2,3-f]quinazoline

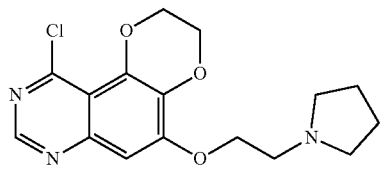 [SMILES: Clc1ncnc2cc(OCCN3CCCC3)c3c(c12)OCCO3]

According to the same procedure as Intermediate 28), a yellow solid product was obtained, MS: 336[M+H]$^+$ Preparation of Intermediate 33: 3-((10-chloro-2,3-dihydro-[1,4]dioxino[2,3-f]quinazoline-5-yl)oxy)-N,N-dimethylpropane-1-amine

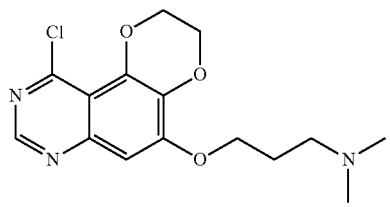 [SMILES: CN(C)CCCOc1cc2ncnc(Cl)c2c2c1OCCO2]

According to the same procedure as Intermediate 28), a yellow solid product was obtained, MS: 324[M+H]⁺

Preparation of Intermediate 34: 10-chloro-5-(3-(tetrahydropyrrol-1-yl)propoxy)-2,3-dihydro-[1,4]dioxino[2,3-f]quinazoline

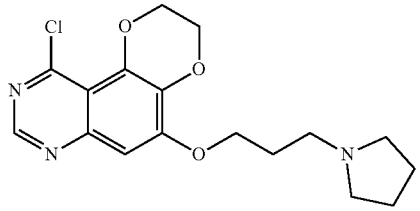 [SMILES: Clc1ncnc2cc(OCCCN3CCCC3)c3c(c12)OCCO3]

According to the same procedure as Intermediate 28), a yellow solid product was obtained, MS: 350[M+H]⁺

Preparation of Intermediate 35: 10-chloro-5-(3-morpholinopropoxy)-2,3-dihydro-[1,4]dioxino[2,3-f]quinazoline

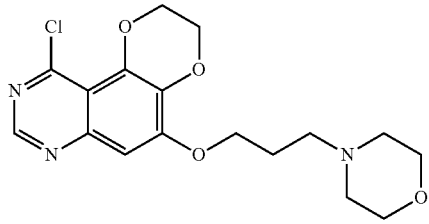 [SMILES: Clc1ncnc2cc(OCCCN3CCOCC3)c3c(c12)OCCO3]

According to the same procedure as Intermediate 28), a yellow solid product was obtained, MS: 366[M+H]⁺

Preparation of Intermediate 36: 10-chloro-5-(1-methylthiopropoxy)-2,3-dihydro-[1,4]dioxino[2,3-f]quinazoline

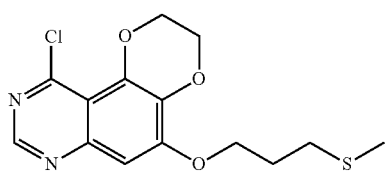 [SMILES: CSCCCOc1cc2ncnc(Cl)c2c2c1OCCO2]

According to the same procedure as Intermediate 28), a yellow solid product was obtained, MS: 327[M+H]⁺

Preparation of Intermediate 37: 10-chloro-5-(3-(4-methylpiperazin-1-yl)propoxy)-2,3-dihydro-[1,4]dioxino[2,3-f]quinazoline

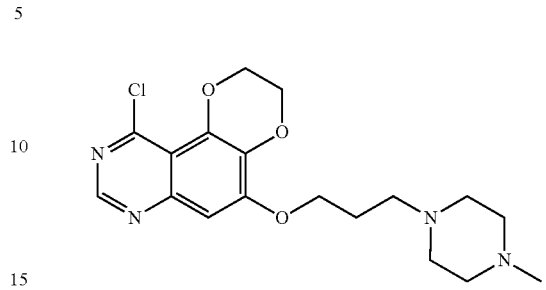

According to the same procedure as Intermediate 28), a yellow solid product was obtained, MS: 379[M+H]⁺

Preparation of Intermediate 38: 10-chloro-5-(3-(piperidin-1-yl)propoxy)-2,3-dihydro-[1,4]dioxino[2,3-f]quinazoline

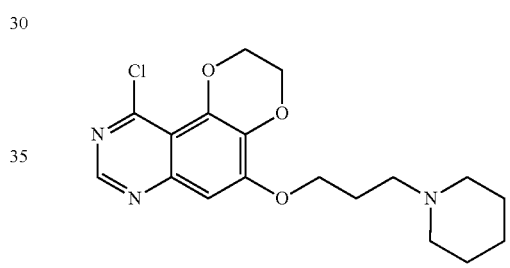

According to the same procedure as Intermediate 28), a yellow solid product was obtained, MS: 364[M+H]⁺

Preparation of Intermediate 39: 4-(3-((10-chloro-2,3-dihydro-[1,4]dioxino[2,3-f]quinazoline-5-yl)oxy)propyl)thiomorpholine 1,1-dioxide

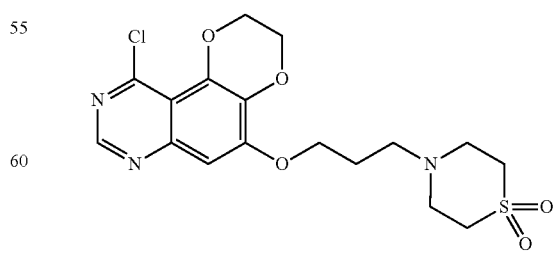

According to the same procedure as Intermediate 28), a yellow solid product was obtained, MS: 414[M+H]⁺

Preparation of Intermediate 40: 10-chloro-5-(6-methoxyhexyloxy)-2,3-dihydro-[1,4]dioxino[2,3-f]quinazoline

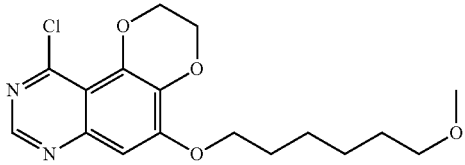 [SMILES: COCCCCCCOc1cc2ncnc(Cl)c2c2c1OCCO2]

According to the same procedure as Intermediate 28), a yellow solid product was obtained, MS: 353[M+H]+

Preparation of Intermediate 41: 10-chloro-5-(6-(dimethylamino)hexyl)-2,3-dihydro-[1,4]dioxino[2,3-f]quinazoline

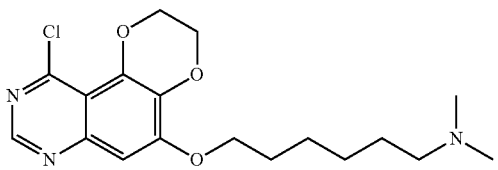 [SMILES: CN(C)CCCCCCOc1cc2ncnc(Cl)c2c2c1OCCO2]

According to the same procedure as Intermediate 28), a yellow solid product was obtained, MS: 366[M+H]+

Preparation of Intermediate 42: 10-chloro-5-isopropoxy-2,3-dihydro-[1,4]dioxino[2,3-f]quinazoline

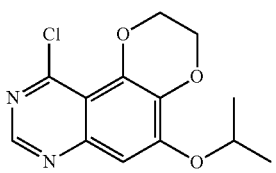 [SMILES: CC(C)Oc1cc2ncnc(Cl)c2c2c1OCCO2]

According to the same procedure as Intermediate 28), a yellow solid product was obtained, MS: 281[M+H]+

Preparation of Intermediate 43) 1-(2-chloro-4-hydroxyphenyl)-3-phenylurea

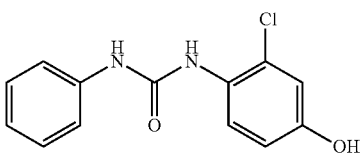 [SMILES: O=C(Nc1ccccc1)Nc1ccc(O)cc1Cl]

According to the operation for Intermediate 21), a white solid compound was obtained from the reaction of 4-amino-3-chlorophenol and aniline, with a yield of 70%; MS: 263[M+H]+

Preparation of Intermediate 44) 1-(2-chloro-4-hydroxyphenyl)-3-isopropylurea

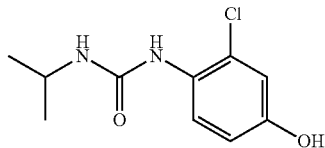

According to the operation for Intermediate 21), a white solid compound was obtained from the reaction of 4-amino-3-chlorophenol and isopropylamine, with a yield of 72%; MS: 229[M+H]+

Preparation of Intermediate 45) 1-(2-chloro-4-hydroxyphenyl)-3-(4-fluorophenyl)urea

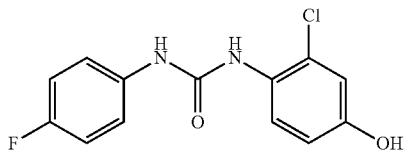 [SMILES: O=C(Nc1ccc(F)cc1)Nc1ccc(O)cc1Cl]

According to the operation for Intermediate 21), a white solid compound was obtained from the reaction of 4-amino-3-chlorophenol and p-fluoroaniline, with a yield of 60%; MS: 281[M+H]+

Preparation of Intermediate 45) 1-(4-hydroxyphenyl)-3-(2-methoxypyridin-4-yl)urea

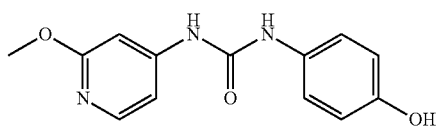 [SMILES: COc1cc(NC(=O)Nc2ccc(O)cc2)ccn1]

According to the operation for Intermediate 21), a white solid compound was obtained from the reaction of 4-aminophenol and 2-methoxypyridin-4-amine, with a yield of 50%; MS: 260[M+H]+

Preparation of Intermediate 46) 1-(2-chloro-4-hydroxyphenyl)-3-cyclopentylurea

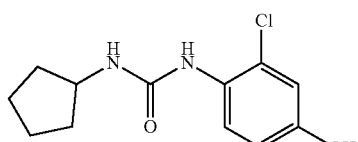

According to the operation for Intermediate 21), a white solid compound was obtained from the reaction of 4-amino-3-chlorophenol and cyclopentylamine, with a yield of 70%; MS: 254[M+H]+

Preparation of Intermediate 47)
1-(2-chloro-4-hydroxyphenyl)-3-cyclobutylurea

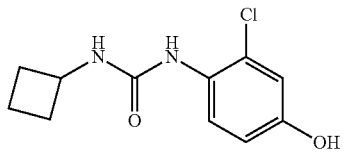 [SMILES: O=C(Nc1ccc(O)cc1Cl)NC1CCC1]

According to the operation for Intermediate 21), a white solid compound was obtained from the reaction of 4-amino-3-chlorophenol and cyclobutylamine, with a yield of 50%; MS: 240[M+H]$^+$ Intermediate 48)
1-(4-amino-2-chlorophenyl)-3-cyclobutylurea

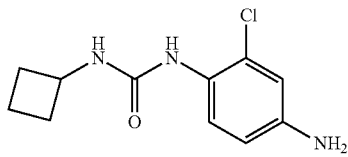 [SMILES: Nc1ccc(NC(=O)NC2CCC2)c(Cl)c1]

According to the operation for Intermediate 2) and 4), a white solid compound was obtained from the reaction of 2-chloro-4-nitroaniline and cyclobutylamine, with a yield of 50%; MS: 240[M+H]$^+$ Intermediate 49)
1-(4-amino-2-chlorophenyl)-3-cyclopentylurea

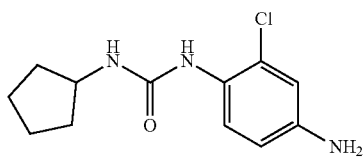 [SMILES: Nc1ccc(NC(=O)NC2CCCC2)c(Cl)c1]

According to the operation for Intermediate 2) and 4), a white solid compound was obtained from the reaction of 2-chloro-4-nitroaniline and cyclopentylamine, with a yield of 50%; MS: 254[M+H]$^+$ Intermediate 50)
1-(4-amino-2-chlorophenyl)-3-isopentylurea

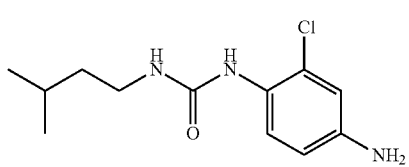 [SMILES: CC(C)CCNC(=O)Nc1ccc(N)cc1Cl]

According to the operation for Intermediate 2) and 4), a white solid compound was obtained from the reaction of 2-chloro-4-nitroaniline and isopentylamine, with a yield of 50%; MS: 256[M+H]$^+$ Preparation of Intermediate 51) 1-(4-chloro-3-(trifluoromethyl)phenyl)-3-(6-hydroxypyridin-3-yl)urea

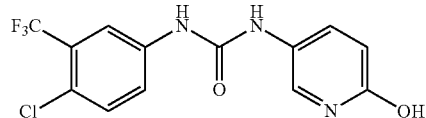 [SMILES: O=C(Nc1ccc(O)nc1)Nc1ccc(Cl)c(C(F)(F)F)c1]

According to the operation for Intermediate 17), a white solid compound was obtained from the reaction of 5-aminopyridin-2(1H)-one and 4-chloro-3-(trifluoromethyl) aniline, with a yield of 45%; MS: 332[M+H]$^+$ Preparation of Intermediate 52) 1-(3-chloro-4-hydroxyphenyl)-3-(2-methoxypyridin-4-yl) urea

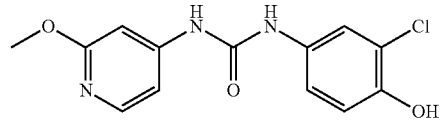 [SMILES: COc1cc(NC(=O)Nc2ccc(O)c(Cl)c2)ccn1]

According to the operation for Intermediate 17), a white solid compound was obtained from the reaction of 4-amino-2-chlorophenol and 2-methoxypyridin-4-amine, with a yield of 45%; MS: 295[M+H]$^+$ Example 1. Preparation of 1-(4-((5-methoxy-2,3-dihydro-[1,4]dioxino[2,3-f]quinazolin-10-yl)amino)phenyl)-3-cyclopropylurea

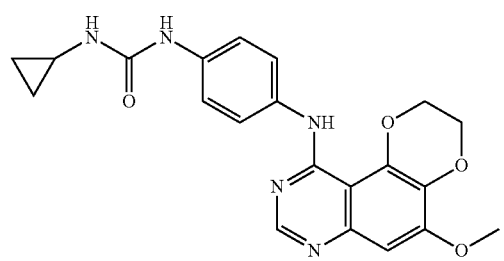 [SMILES: COc1cc2ncnc(Nc3ccc(NC(=O)NC4CC4)cc3)c2c2c1OCCO2]

51 mg (0.2 mmol) 10-chloro-5-methoxy-2,3-dihydro-[1,4]dioxino[2,3-f]quinazoline, 38.5 mg (0.2 mmol) 1-(4-aminophenyl)-3-cyclopropylurea, and 10 mL isopropanol were added in a reaction vessel, and the reaction was carried out at 80° C. for 5 hours. After the reaction was completed, the mixture was cooled, filtered, washed with isopropanol for three times, and dried to obtain 45 mg of a yellow solid, with a yield of 50%; $^1$H NMR (DMSO-d$_6$, 400 MHz) δ ppm: 0.41 (2H, br), 0.64 (2H, br), 2.50 (1H, br), 3.98 (3H, s), 4.44 (2H, br), 4.61 (2H, br), 6.63 (1H, s), 7.00 (1H, s), 7.45 (2H, d, J=8.0 Hz), 7.50 (2H, d, J=8.0 Hz), 8.69 (1H, s), 8.76 (1H, s), 10.51 (1H, s); MS: 408[M+H]$^+$.

Example 2. Preparation of 1-(2-chloro-4-((5-methoxy-2,3-dihydro-[1,4]dioxino[2,3-f]quinazolin-10-yl)amino)phenyl)-3-cyclopropylurea

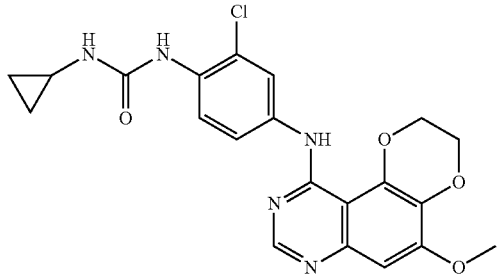 [SMILES: COc1cc2ncnc(Nc3ccc(NC(=O)NC4CC4)c(Cl)c3)c2c2c1OCCO2]

According to the same procedure in Example 1, the target product as a yellow solid was obtained from the reaction of 10-chloro-5-methoxy-2,3-dihydro-[1,4]dioxino[2,3-f]quinazoline and 1-(4-amino-2-chlorophenyl)-3-cyclopropylurea, with a yield of 58%;

$^1$HNMR (DMSO-$d_6$, 400 MHz) δ ppm: 0.43 (2H, br), 0.67 (2H, br), 2.51 (1H, br), 3.98 (3H, s), 4.44 (2H, br), 4.60 (2H, br), 6.97 (1H, s), 7.30 (1H, s), 7.49 (1H, d, J=8.0 Hz), 7.79 (1H, s), 8.04 (1H, s), 8.23 (1H, d, J=8.0 Hz), 8.74 (1H, s), 10.47 (1H, s); MS: 442[M+H]$^+$.

Example 3. Preparation of 1-(4-((5-methoxy-2,3-dihydro-[1,4]dioxino[2,3-f]quinazolin-10-yl)amino)phenyl)-3-(3-methoxyphenyl)urea

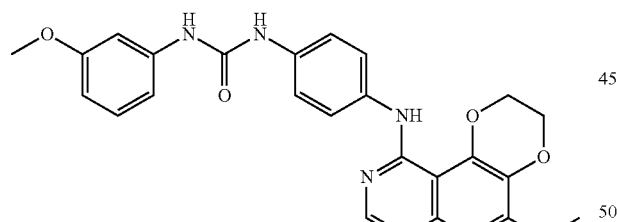

According to the same procedure in Example 1, the product as a yellow solid was obtained from 10-chloro-5-methoxy-2,3-dihydro-[1,4]dioxino[2,3-f]quinazoline and 1-(4-aminophenyl)-3-(3-methoxyphenyl)urea, with a yield of 58%; $^1$HNMR (DMSO-$d_6$, 400 MHz) δ ppm: 3.55 (3H, s), 3.98 (3H, s), 4.44 (2H, br), 4.61 (2H, br), 6.56 (1H, d, J=4.0 Hz), 6.94-6.99 (2H, m), 7.18-7.21 (2H, m), 7.50 (2H, d, J=8.0 Hz), 7.56 (2H, d, J=8.0 Hz), 8.71 (1H, s), 9.19 (1H, s), 9.33 (1H, s), 10.55 (1H, s); MS: 474[M+H]$^+$.

Example 4. Preparation of 1-(2-chloro-4-((5-methoxy-2,3-dihydro-[1,4]dioxino[2,3-f]quinazolin-10-yl)amino)phenyl)-3-(3-methoxyphenyl)urea

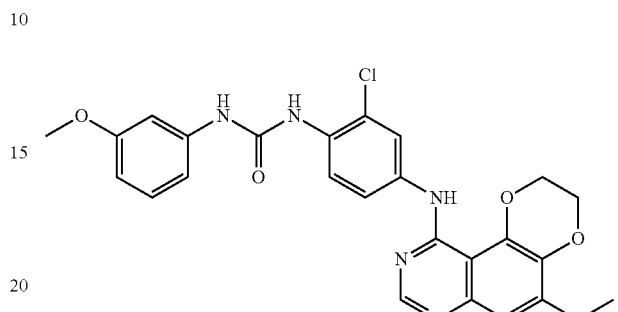

According to the same procedure in Example 1, the product as a yellow solid was obtained from 10-chloro-5-methoxy-2,3-dihydro-[1,4]dioxino[2,3-f]quinazoline and 1-(4-amino-2-chloro-phenyl)-3-(3-methoxyphenyl)urea, with a yield of 58%;

$^1$HNMR (DMSO-$d_6$, 400 MHz) δ ppm: 3.75 (3H, s), 3.93 (3H, s), 4.40 (2H, br), 4.60 (2H, br), 6.58 (1H, d, J=4.0 Hz), 6.96 (2H, d, J=8.0 Hz), 7.22 (2H, t, J=8.0 Hz), 7.65 (1H, d, J=8.0 Hz), 8.09 (1H, d, J=8.0 Hz), 8.18 (1H, s), 8.26 (1H, s), 8.43 (1H, s), 9.34 (1H, s), 9.58 (1H, s), MS: 508[M+H]$^+$.

Example 5. Preparation of 1-(2-chloro-4-((5-methoxy-2,3-dihydro-[1,4]dioxino[2,3-f]quinazolin-10-yl)amino)phenyl)-3-(pyridin-2-yl)urea

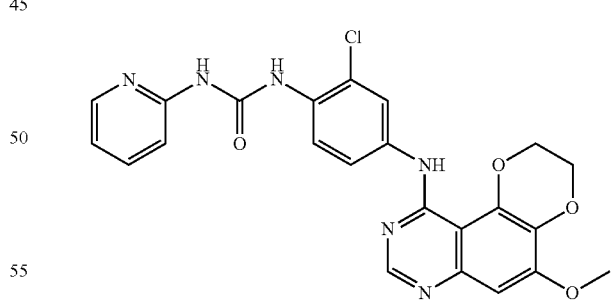

According to the same procedure in Example 1, a yellow solid was obtained from 10-chloro-5-methoxy-2,3-dihydro-[1,4]dioxino[2,3-f]quinazoline and 1-(4-amino-2-chlorophenyl)-3-(pyridin-2-yl)urea, with a yield of 71%; $^1$HNMR (DMSO-$d_6$, 400 MHz) δ ppm: 3.97 (3H, s), 4.41-4.44 (2H, m), 4.60-4.63 (2H, m), 6.94 (1H, s), 7.06 (1H, t, J=8.0 Hz), 7.25 (1H, d, J=8.0 Hz), 7.61 (1H, d, J=8.0 Hz), 7.79 (1H, d, J=8.0 Hz), 7.98 (1H, s), 8.33 (1H, s), 8.39 (1H, d, J=8.0 Hz), 8.68 (1H, s), 10.05 (1H, s), 10.29 (1H, s), MS: 479[M+H]$^+$.

Example 6. Preparation of 1-(2-chloro-4-((5-methoxy-2,3-dihydro-[1,4]dioxino[2,3-f]quinazolin-10-yl)amino)phenyl)-3-phenylurea

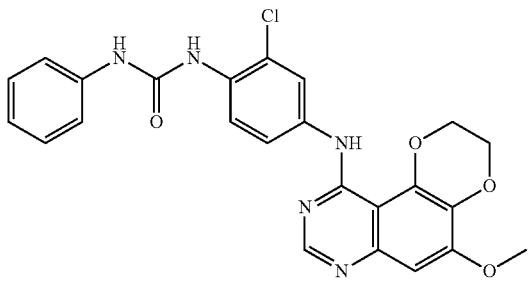 [SMILES: COc1cc2ncnc(Nc3ccc(NC(=O)Nc4ccccc4)c(Cl)c3)c2c2c1OCCO2]

According to the same procedure in Example 1, a yellow solid was obtained from 10-chloro-5-methoxy-2,3-dihydro-[1,4]dioxino[2,3-f]quinazoline and 1-(4-amino-2-chlorophenyl)-3-phenylurea, with a yield of 62%; $^1$H NMR (DMSO-d$_6$, 400 MHz) δ ppm: 3.98 (3H, s), 4.44 (2H, s), 4.62 (2H, s), 7.00 (2H, t, J=8.0 Hz), 7.30 (2H, t, J=8.0 Hz), 7.52 (2H, d, J=8.0 Hz), 7.55 (1H, d, J=8.0 Hz), 7.86 (1H, s), 8.23 (1H, d, J=8.0 Hz), 8.57 (1H, s), 8.74 (1H, s), 9.77 (1H, br), 10.47 (1H, s), MS: 478[M+H]$^+$.

Example 7. Preparation of 1-(2-chloro-4-((5-methoxy-2,3-dihydro-[1,4]dioxino[2,3-f]quinazolin-10-yl)amino)phenyl)-3-(4-fluorophenyl)urea

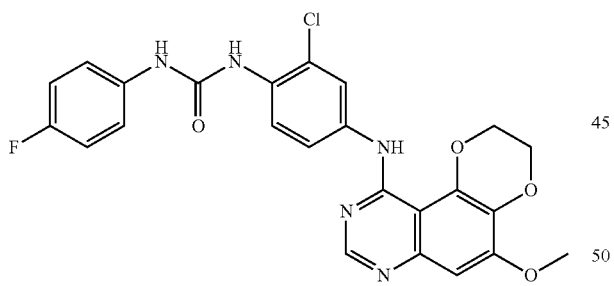

According to the same procedure in Example 1, a yellow solid was obtained from 10-chloro-5-methoxy-2,3-dihydro-[1,4]dioxino[2,3-f]quinazoline and 1-(4-amino-2-chlorophenyl)-3-(3-fluorophenyl)urea, with a yield of 51%;

$^1$H NMR (DMSO-d$_6$, 400 MHz) δ ppm: 3.92 (3H, s), 4.40 (2H, s), 4.60 (2H, s), 6.90 (1H, t, J=8.0 Hz), 7.15 (2H, t, J=12.0 Hz), 7.49 (2H, t, J=8.0 Hz), 7.66 (1H, d, J=8.0 Hz), 8.08 (1H, d, J=8.0 Hz), 8.18 (1H, s), 8.27 (1H, s), 8.43 (1H, s), 9.37 (1H, s), 9.60 (1H, s); MS: 496[M+H]$^+$.

Example 8. Preparation of 1-(2-chloro-4-((5-methoxy-2,3-dihydro-[1,4]dioxino[2,3-f]quinazolin-10-yl)amino)phenyl)-3-(3-methylisoxazol-5-yl)urea

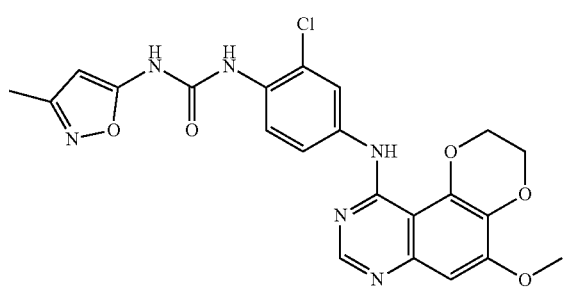

According to the same procedure in Example 1, a yellow solid was obtained from 10-chloro-5-methoxy-2,3-dihydro-[1,4]dioxino[2,3-f]quinazoline and 1-(4-amino-2-chlorophenyl)-3-(3-methylisoxazol-5-yl)-urea, with a yield of 80%;

$^1$HNMR (DMSO-d$_6$, 400 MHz) δ ppm: 2.38 (3H, s), 3.98 (3H, s), 4.44 (2H, s), 4.62 (2H, s), 6.51 (1H, s), 7.03 (1H, s), 7.58 (1H, d, J=8.0 Hz), 7.89 (1H, s), 8.19 (1H, d, J=8.0 Hz), 8.74 (1H, s), 8.90 (1H, s), 10.30 (1H, s), 10.45 (1H, s); MS: 483[M+H]$^+$.

Example 9. Preparation of 1-(2-chloro-4-((5-methoxy-2,3-dihydro-[1,4]dioxino[2,3-f]quinazolin-10-yl)amino)phenyl)-3-isopropylurea

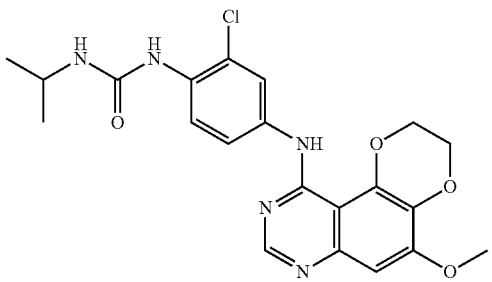 [SMILES: COc1cc2ncnc(Nc3ccc(NC(=O)NC(C)C)c(Cl)c3)c2c2c1OCCO2]

According to the same procedure in Example 1, a yellow solid was obtained from 10-chloro-5-methoxy-2,3-dihydro-[1,4]dioxino[2,3-f]quinazoline and 1-(2-chloro-4-nitrophenyl)-3-isopropylurea, with a yield of 70%;

$^1$HNMR (DMSO-d$_6$, 400 MHz) δ ppm: 1.11 (6H, d, J=8.0 Hz), 3.73-3.79 (1H, m), 3.92 (3H, s), 4.39 (2H, br), 4.58 (2H, br), 6.87 (1H, d, J=8.0 Hz), 6.92 (1H, s), 7.56 (1H, d, J=8.0 Hz), 7.87 (1H, s), 8.11 (2H, d, J=8.0 Hz), 8.41 (1H, s), 9.56 (1H, s); MS: 444[M+H]$^+$.

Example 10. Preparation of 1-(2-chloro-4-((5-methoxy-2,3-dihydro-[1,4]dioxino[2,3-f]quinazolin-10-yl)amino)phenyl)-3-(2-methoxypyridin-4-yl)urea

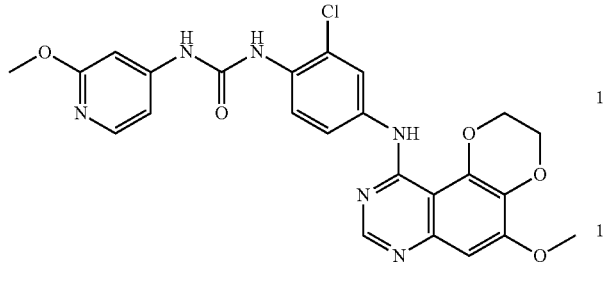

According to the same procedure in Example 1, a yellow solid was obtained from 10-chloro-5-methoxy-2,3-dihydro-[1,4]dioxino[2,3-f]quinazoline and 1-(2-chloro-4-nitrophenyl)-3-(2-methoxypyridin-4-yl)urea, with a yield of 72%;

$^1$HNMR (DMSO-$d_6$, 400 MHz) δ ppm: 3.17 (3H, s), 3.99 (3H, s), 4.45 (2H, br), 4.61 (2H, br), 7.04 (1H, s), 7.20 (1H, d, J=4.0 Hz) 7.39 (1H, s), 7.60 (1H, s), 7.87 (1H, s), 8.14 (2H, d, J=8.0 Hz), 8.18 (1H, s), 8.79 (1H, s), 9.11 (1H, s), 10.60 (1H, s); MS: 509[M+H]$^+$.

Example 11. Preparation of 1-(2-chloro-4-((5-methoxy-2,3-dihydro-[1,4]dioxino[2,3-f]quinazolin-10-yl)amino)phenyl)-3-(4-chloro-3-(trifluoromethyl)phenyl)urea

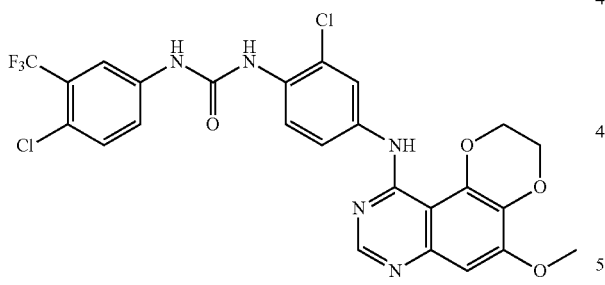

According to the same procedure in Example 1, a yellow solid was obtained from 10-chloro-5-methoxy-2,3-dihydro-[1,4]dioxino[2,3-f]quinazoline and 1-(2-chloro-4-aminophenyl)-3-(4-chloro-3-(trifluoromethyl)phenyl)urea, with a yield of 76%;

$^1$HNMR (DMSO-$d_6$, 400 MHz) δ ppm: 3.93 (3H, s), 4.40 (2H, s), 4.59 (2H, s), 6.90 (1H, s), 7.64 (2H, s), 7.68 (1H, d, J=8.0 Hz), 8.04 (1H, d, J=8.0 Hz), 8.13 (1H, d, J=8.0 Hz), 8.20 (1H, s), 8.41 (1H, s), 8.44 (1H, s) 9.62 (1H, s), 9.79 (1H, s); MS: 580[M+H]$^+$.

Example 12. Preparation of 1-(2-chloro-4-((5-methoxy-2,3-dihydro-[1,4]dioxino[2,3-f]quinazolin-10-yl)amino)phenyl)-3-(2-fluoro-4-(trifluoromethyl)phenyl)urea

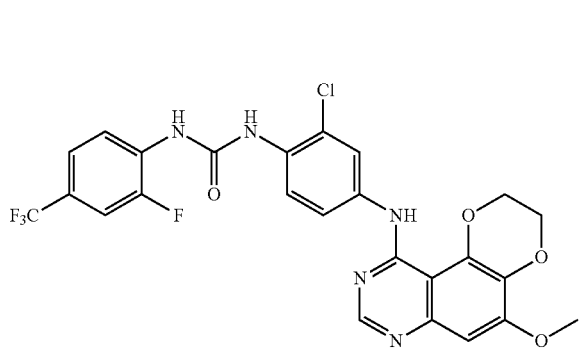 [SMILES: COc1cc2ncnc(Nc3ccc(NC(=O)Nc4ccc(C(F)(F)F)cc4F)c(Cl)c3)c2c2c1OCCO2]

According to the same procedure in Example 1, a yellow solid was obtained from 10-chloro-5-methoxy-2,3-dihydro-[1,4]dioxino[2,3-f]quinazoline and 1-(2-chloro-4-aminophenyl)-3-(2-fluoro-4-(trifluoromethyl)phenyl)urea, with a yield of 66%;

$^1$HNMR (DMSO-$d_6$, 400 MHz) δ ppm: 3.92 (3H, s), 4.40 (2H, s), 4.60 (2H, s), 6.91 (1H, s), 7.42 (1H, s), 7.52 (1H, t, J=8.0 Hz), 7.67 (1H, d, J=8.0 Hz), 8.08 (1H, d, J=8.0 Hz), 8.21 (1H, s), 8.44 (1H, s), 8.65 (1H, s) 8.91 (1H, s), 9.62 (2H, s); MS: 564[M+H]$^+$.

Example 13. Preparation of 1-(2-chloro-4-((5-methoxy-2,3-dihydro-[1,4]dioxino[2,3-f]quinazolin-10-yl)amino)phenyl)-3-(4-(phenoxy)phenyl)urea According to the same procedure in Example 1, a yellow solid was obtained from 10-chloro-5-methoxy-2,3-dihydro-[1,4]dioxino[2,3-f]quinazoline and 1-(2-chloro-4-aminophenyl)-3-(4-(phenoxy)phenyl)urea, with a yield of 78%;

$^1$H NMR (DMSO-$d_6$, 400 MHz) δ ppm: 3.93 (3H, s), 4.41 (2H, br), 4.59 (2H, br), 6.90 (1H, s), 6.96-7.02 (4H, m), 7.10 (1H, t, J=8.0 Hz), 7.37 (2H, t, J=8.0 Hz), 7.50 (2H, d, J=8.0 Hz), 7.62-7.65 (1H, m), 8.11-8.14 (2H, m), 8.29 (1H, s), 8.48 (1H, s), 9.38 (1H, s), 9.74 (1H, s); MS: 570[M+H]$^+$.

Example 14. Preparation of 1-(2-chloro-4-((5-methoxy-2,3-dihydro-[1,4]dioxino[2,3-f]quinazolin-10-yl)oxy)phenyl)-3-phenylurea

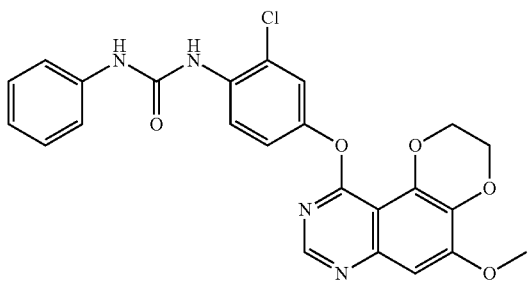 [SMILES: COc1cc2ncnc(Oc3ccc(NC(=O)Nc4ccccc4)c(Cl)c3)c2c2c1OCCO2]

Step a) Preparation of 10-(3-chloro-4-nitrophenoxy)-5-methoxy-2,3-dihydro-[1,4]dioxino[2,3-f]quinazoline

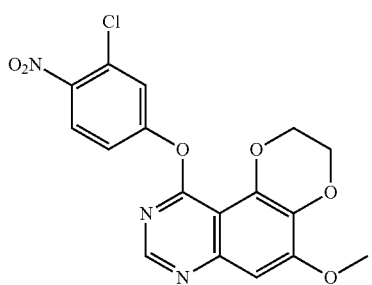 [SMILES: COc1cc2ncnc(Oc3ccc([N+](=O)[O-])c(Cl)c3)c2c2c1OCCO2]

10-chloro-5-methoxy-2,3-dihydro-[1,4]dioxino[2,3-f]quinazoline (25 mg, 0.1 mmol), 3-chloro-4-nitrophenol, potassium carbonate $K_2CO_3$ (20 mg, 0.15 mmol) were reacted in isopropanol (10 ml) at 80° C. for 3 h. After cooling, the reaction mixture was added with water and suction filtered to give 31 mg of a yellow solid, with a yield of 80%; MS: 390[M+H]$^+$.

Step b) Preparation of 2-chloro-4-((5-methoxy-2,3-dihydro-[1,4]dioxino[2,3-f]quinazolin-10-yl)oxy)aniline

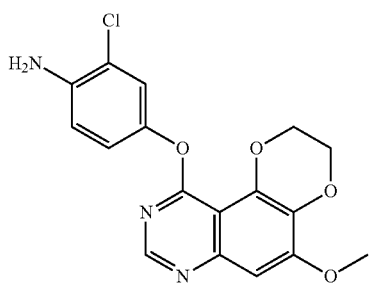

10-(3-chloro-4-nitrophenoxy)-5-methoxy-2,3-dihydro-[1,4]dioxino[2,3-f]quinazoline (31 mg, 0.08 mmol) was dissolved in 5 mL methanol, 50 mg Raney nickel was added thereto, and the mixture was stirred for 2 hrs under hydrogen atmosphere. The reaction mixture was suction filtered and the filtrate was concentrated to give 28 mg product, with a yield of 99%. MS: 360[M+H]$^+$.

Step c) Preparation of 1-(2-chloro-4-((5-methoxy-2,3-dihydro-[1,4]dioxino[2,3-f]quinazolin-10-yl)oxy)phenyl)-3-phenylurea 2-chloro-4-((5-methoxy-2,3-dihydro-[1,4]dioxino[2,3-f]quinazolin-10-yl)oxy)aniline (28 mg, 0.08 mmol) was dissolved in 5 mL dichloromethane. 0.2 mL triethylamine and triphosgene (29 mg, 0.1 mmol) were added and the mixture was stirred for 0.5 hr. Aniline (9 mg, 0.1 mmol) was added and the mixture was continuously stirred until the reaction was complete. The reaction mixture was concentrated and subjected to column chromatography to give 30 mg product, with a yield of 80%.

$^1$H NMR (DMSO-d$_6$, 400 MHz) δ ppm: 3.97 (3H, s), 4.40 (2H, br), 4.45 (2H, br), 7.00 (1H, t, J=8.0 Hz), 7.07 (1H, s), 7.20-7.23 (1H, m), 7.29-7.33 (2H, m), 7.46-7.50 (3H, m), 8.19 (1H, d, J=8.0 Hz), 8.40 (1H, s), 8.49 (1H, s), 9.48 (1H, s); MS: 479[M+H]$^+$.

Example 15. Preparation of 1-(2-chloro-4-((5-methoxy-2,3-dihydro-[1,4]dioxino[2,3-f]quinazolin-10-yl)oxy)phenyl)-3-isopropylurea

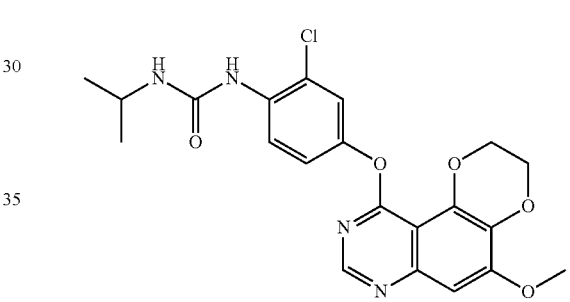

According to the same operation in Example 14, but aniline was replaced by isopropylamine, 35 mg of a yellow solid was obtained, with a yield of 80%;

$^1$H NMR (DMSO-d$_6$, 400 MHz) δ ppm: 1.12 (6H, d, J=8.0 Hz), 3.77 (1H, p, J=8.0 Hz), 3.97 (3H, s), 4.39 (2H, br), 4.45 (2H, br), 6.93 (1H, t, J=8.0 Hz), 7.05 (1H, s), 7.13 (1H, d, J=12.0 Hz), 7.38 (1H, s), 7.94 (1H, s), 8.20 (1H, d, J=8.0 Hz), 8.45 (1H, s); MS: 445[M+H]$^+$.

Example 16. Preparation of 1-(2-chloro-4-((5-methoxy-2,3-dihydro-[1,4]dioxino[2,3-f]quinazolin-10-yl)oxy)phenyl)-3-(4-fluorophenyl)urea

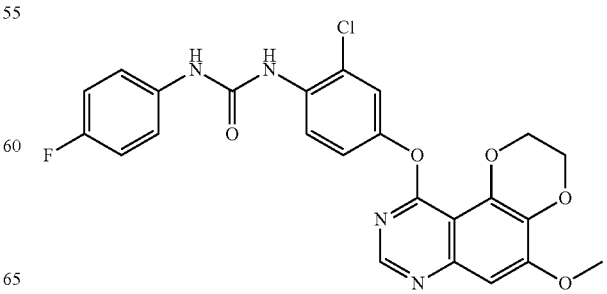

According to the same operation in Example 14, but aniline was replaced by p-fluoroaniline, 25 mg of a yellow solid was obtained, with a yield of 65%;

¹H NMR (DMSO-d₆, 400 MHz) δ ppm: 3.97 (3H, s), 4.39 (2H, br), 4.45 (2H, br), 7.06 (1H, s), 7.15 (2H, t, J=8.0 Hz), 7.21 (1H, d, J=8.0 Hz), 7.46-7.51 (3H, m), 8.17 (1H, d, J=8.0 Hz), 8.33 (1H, s), 8.46 (1H, s), 9.42 (1H, s) MS: 497[M+H]⁺.

Example 17. Preparation of 1-(2-chloro-4-((5-methoxy-2,3-dihydro-[1,4]dioxino[2,3-f]quinazolin-10-yl)amino)phenyl)-3-(3-methylsulfonylphenyl)urea

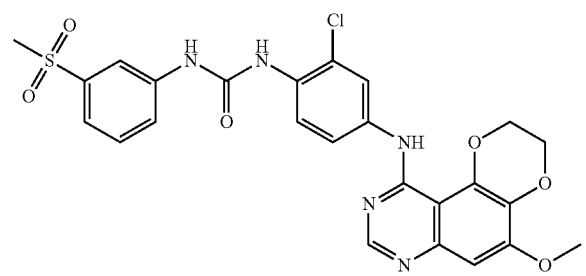

According to the same procedure in Example 1, a yellow solid was obtained from 10-chloro-5-methoxy-2,3-dihydro-[1,4]dioxino[2,3-f]quinazoline and 1-(4-amino-2-chlorophenyl)-3-(3-(methylsulfonyl)phenyl)urea;

¹H NMR (DMSO-d₆, 400 MHz) δ ppm: 3.21 (3H, s), 3.97 (3H, s), 4.31-4.70 (4H, m), 6.97 (1H, s), 7.49-7.64 (3H, m), 7.68 (1H, d, J=5.7 Hz), 7.94 (1H, s), 8.20 (2H, d, J=8.2 Hz), 8.66 (2H, d, J=25.9 Hz), 10.19 (1H, s), 10.31 (1H, s); MS: 556[M+H]⁺.

Example 18. Preparation of 1-(4-chloro-3-(trifluoromethyl)phenyl)-3-(4-((5-methoxy-2,3-dihydro-[1,4]dioxino[2,3-f]quinazolin-10-yl)oxy)phenyl)urea

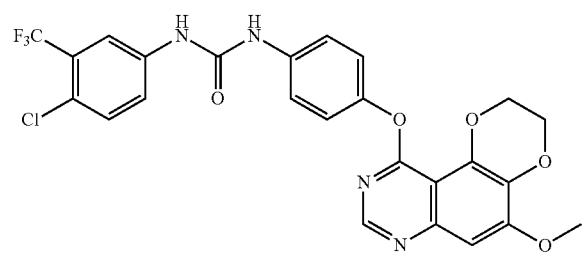 [SMILES: COc1cc2ncnc(Oc3ccc(NC(=O)Nc4ccc(Cl)c(C(F)(F)F)c4)cc3)c2c2c1OCCO2]

1-(4-chloro-3-(trifluoromethyl)phenyl)-3-(4-hydroxyphenyl)urea, 10-chloro-5-methoxy-2,3-dihydro-[1,4]dioxino[2,3-f]quinazoline and K₂CO₃ (20 mg, 0.15 mmol) was reacted in isopropanol (10 ml) at 80° C. for 3 h. After cooling, the mixture was extracted with ethyl acetate and saturated brine. The organic phase was dried with anhydrous sodium sulfate, and concentrated to give a yellow solid. The resulting solid was purified by column chromatography (Silica gel 200-300 mesh, the volume ratio of petroleum ether and ethyl acetate is 1:1), to give 30 mg of a yellow solid, with a yield of 53%;

¹HNMR (DMSO-d₆, 400 MHz) δ ppm: 3.97 (3H, s), 4.28-4.58 (4H, m), 7.05 (1H, s), 7.15 (2H, d, J=8.9 Hz), 7.53 (2H, d, J=9.0 Hz), 7.76-7.59 (2H, m), 8.13 (1H, d, J=2.4 Hz), 8.43 (1H, s), 8.93 (1H, s), 9.20 (1H, s); MS: 547[M+H]⁺.

Example 19. Preparation of 1-(4-chloro-3-(trifluoromethyl)phenyl)-3-(2-fluoro-4-((5-methoxy-2,3-dihydro-[1,4]dioxino[2,3-f]quinazolin-10-yl)oxy)phenyl)urea

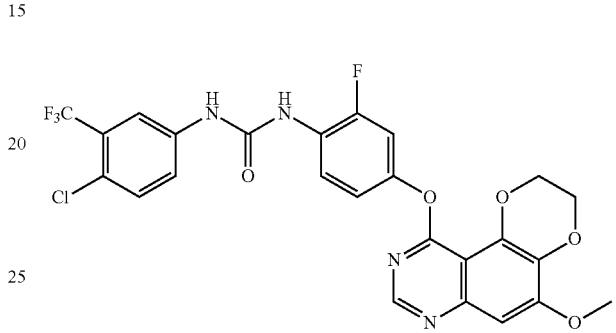

According to the same operation in Example 18, the target product as a grey solid was obtained from the reaction of 1-(4-chloro-3-(trifluoromethyl)phenyl)-3-(2-fluoro-4-hydroxyphenyl)urea and 10-chloro-5-methoxy-2,3-dihydro-[1,4]dioxino[2,3-f]quinazoline, with a yield of 74%; ¹HNMR (DMSO-d₆, 400 MHz) δ ppm: 3.97 (3H, s), 4.27-4.54 (4H, m), 7.06 (2H, s), 7.32 (1H, d, J=11.7), 7.63 (2H, s), 8.10 (2H, d, J=19.4), 8.46 (1H, s), 8.69 (1H, d, J=1.8 Hz), 9.51 (1H, s); MS: 565[M+H]⁺.

Example 20. Preparation of 1-(2-fluoro-5-(trifluoromethyl)phenyl)-3-(4-((5-methoxy-2,3-dihydro-[1,4]dioxino[2,3-f]quinazolin-10-yl)oxy)phenyl)urea

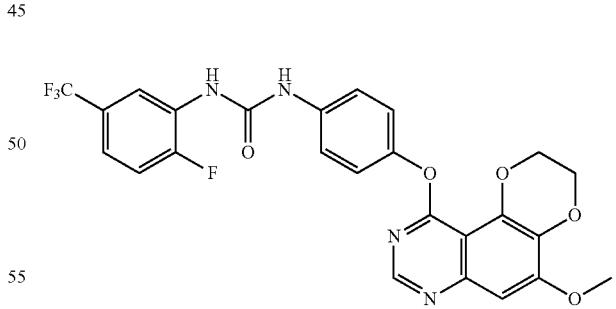

According to the same operation in Example 18, the target product as a white solid was obtained from the reaction of 1-(2-fluoro-5-(trifluoromethyl)phenyl)-3-(4-hydroxyphenyl)urea and 10-chloro-5-methoxy-2,3-dihydro-[1,4]dioxino[2,3-f]quinazoline, with a yield of 55%; ¹H NMR (DMSO-d₆, 400 MHz) δ ppm: 3.97 (3H, s), 4.42 (4H, d, J=25.9), 7.05 (1H, s), 7.17 (2H, d, J=8.9 Hz), 7.53 (4H, d, J=8.9 Hz), 8.43 (1H, s), 8.64 (1H, dd, J=7.3, 2.1 Hz), 8.91 (1H, d, J=2.8 Hz), 9.25 (1H, s); MS: 531[M+H]⁺.

Example 21. Preparation of 1-(2,4-difluorophenyl)-3-(2-fluoro-4-((5-methoxy-2,3-dihydro-[1,4]dioxino[2,3-f]quinazolin-10-yl)oxy)phenyl)urea

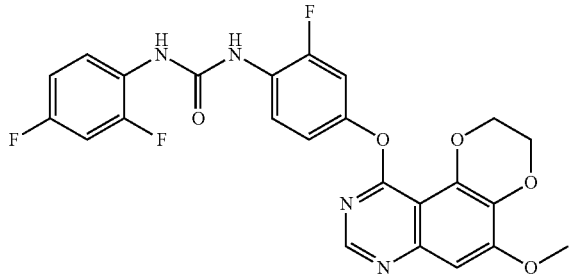 [SMILES: COc1cc2ncnc(Oc3ccc(NC(=O)Nc4ccc(F)cc4F)c(F)c3)c2c2c1OCCO2]

According to the same operation in Example 18, the target product as a purple solid was obtained from the reaction of 1-(2,4-difluorophenyl)-3-(2-fluoro-4-hydroxyphenyl)urea and 10-chloro-5-methoxy-2,3-dihydro-[1,4]dioxino[2,3-f]quinazoline, with a yield of 55%; $^1$HNMR (DMSO-$d_6$, 400 MHz) δ ppm: 3.97 (3H, s), 4.42 (4H, d, J=25.9), 7.05-7.07 (3H, m), 7.29-7.33 (2H, m), 8.13-8.16 (2H, m), 8.44 (1H, s), 8.98 (1H, s), 9.00 (1H, s); MS: 499[M+H]$^+$.

Example 22. Preparation of 1-(2-chloro-4-((5-methoxy-2,3-dihydro-[1,4]dioxino[2,3-f]quinazolin-10-yl)oxy)phenyl)-3-cyclopropylurea

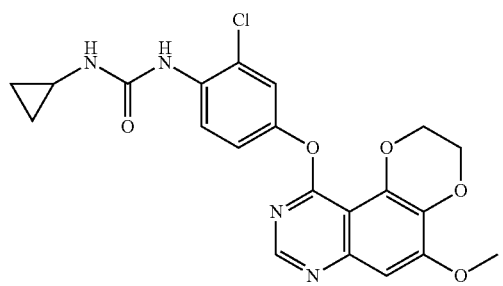 [SMILES: COc1cc2ncnc(Oc3ccc(NC(=O)NC4CC4)c(Cl)c3)c2c2c1OCCO2]

According to the same operation in Example 18, a pale purple solid was obtained from the compound 10-chloro-5-methoxy-2,3-dihydro-[1,4]dioxino[2,3-f]quinazoline and 1-(2-chloro-4 hydroxyphenyl)-3-cyclopropylurea, with a yield of 48%;

$^1$HNMR (DMSO-$d_6$, 400 MHz) δ ppm: 0.36-0.47 (2H, m), 0.67 (2H, br), 2.58 (1H, dd, J=6.8, 3.7 Hz), 3.96 (3H, s), 4.32-4.49 (4H, m), 7.05 (1H, s), 7.09-7.24 (2H, m), 7.39 (1H, d. J=2.7 Hz), 7.92 (1H, s), 8.17 (1H, d, J=9.0 Hz), 8.45 (1H, s); MS: 443[M+H]$^+$.

Example 23. Preparation of 1-(4-((5-methoxy-2,3-dihydro-[1,4]dioxino[2,3-f]quinazolin-10-yl)oxy)phenyl)-3-(3-methoxyphenyl)urea

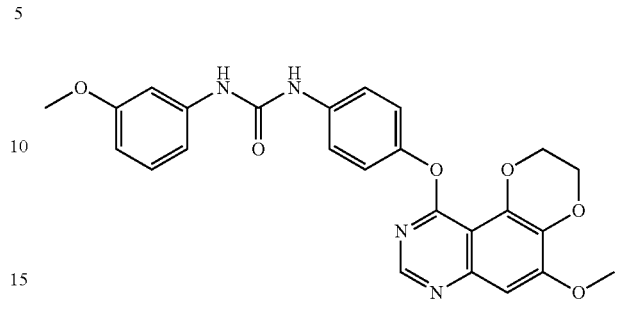

According to the same operation in Example 18, the target product as a pale yellow solid was obtained from the reaction of 10-chloro-5-methoxy-2,3-dihydro-[1,4]dioxino[2,3-f]quinazoline and 1-(4-hydroxyphenyl)-3-(3-methoxyphenyl)urea, with a yield of 52%; $^1$HNMR (DMSO-$d_6$, 400 MHz) δ ppm: 3.74 (3H, s), 3.97 (3H, s), 4.39 (2H, br), 4.46 (2H, br), 6.55 (1H, d, J=8.0 Hz), 6.96 (1H, d, J=8.0 Hz), 7.05 (1H, s), 7.12-7.22 (3H, m), 7.52 (2H, d, J=8.0 Hz), 7.84 (1H, s), 8.43 (1H, s), 8.88 (1H, s), 8.91 (1H, s); MS: 475[M+H]$^+$.

Example 24. Preparation of 1-(3-chloro-4-((5-methoxy-2,3-dihydro-[1,4]dioxino[2,3-f]quinazolin-10-yl)oxy)phenyl)-3-(3-methoxyphenyl)urea

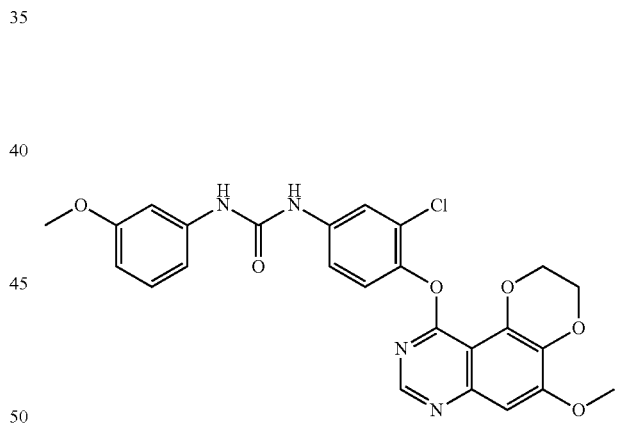

According to the same operation in Example 18, the target product as a white solid was obtained from the reaction of 10-chloro-5-methoxy-2,3-dihydro-[1,4]dioxino[2,3-f]quinazoline and 1-(3-chloro-4-hydroxyphenyl)-3-(3-methoxyphenyl)urea, with a yield of 58%; $^1$HNMR (DMSO-$d_6$, 400 MHz) δ ppm: 3.74 (3H, s), 3.98 (3H, s), 4.40 (2H, br), 4.47 (2H, br), 6.58 (1H, d, J=8.0 Hz), 6.96 (1H, d, J=8.0 Hz), 7.08 (1H, s), 7.17-7.21 (2H, m), 7.30-7.38 (2H, m), 7.84 (1H, s), 8.44 (1H, s), 8.89 (1H, s), 9.02 (1H, s); MS: 509[M+H]$^+$.

Example 25. Preparation of 1-(4-((5-methoxy-2,3-dihydro-[1,4]dioxino[2,3-f]quinazolin-10-yl)oxy)phenyl)-3-(2-methoxy pyridin-4-yl)urea

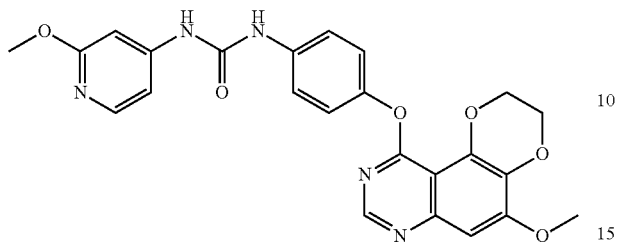

According to the same operation in Example 18, the target product as pale yellow solid was obtained from the reaction of 10-chloro-5-methoxy-2,3-dihydro-[1,4]dioxino[2,3-f]quinazoline and 1-(4-hydroxyphenyl)-3-(2-methoxypyridin-4-yl)urea, with a yield of 56%; $^1$HNMR (DMSO-d$_6$, 400 MHz) δ ppm: 3.82 (3H, s), 3.97 (3H, s), 4.40 (2H, br), 4.47 (2H, br), 6.97-7.00 (2H, m), 7.05 (1H, s), 7.16 (2H, d, J=8.0 Hz), 7.52 (2H, d, J=8.0 Hz), 7.97 (1H, d, J=4.0 Hz), 8.43 (1H, s), 9.21 (1H, s), 9.43 (1H, s); MS: 476[M+H]$^+$.

Example 26. Preparation of 1-(3-chloro-4-((5-methoxy-2,3-dihydro-[1,4]dioxino[2,3-f]quinazolin-10-yl)oxy)phenyl)-3-(2-methoxypyridin-4-yl)urea

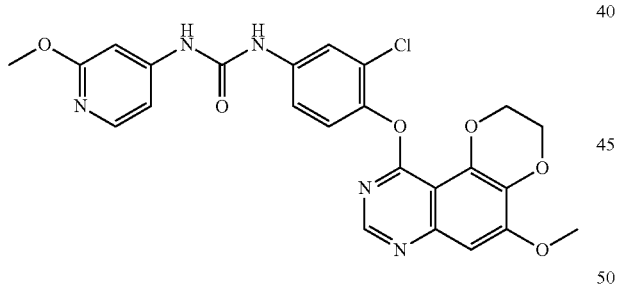

According to the same operation in Example 18, the target product as a pale yellow solid was obtained from the reaction of 10-chloro-5-methoxy-2,3-dihydro-[1,4]dioxino[2,3-f]quinazoline and 1-(3-chloro-4-hydroxyphenyl)-3-(2-methoxypyridin-4-yl)urea, with a yield of 52%; 1H NMR (DMSO-d$_6$, 400 MHz) δ ppm: 3.81 (3H, s), 3.97 (3H, s), 4.39 (2H, br), 4.46 (2H, br), 6.98-7.00 (2H, m), 7.08 (1H, s), 7.34 (1H, d, J=8.0 Hz), 7.40 (1H, d, J=12.0 Hz), 7.83 (1H, s), 7.99 (1H, d, J=4.0 Hz), 8.45 (1H, s), 9.12 (1H, s), 9.29 (1H, s); MS: 510[M+H]$^+$.

Example 27. 1-(2-chloro-4-((5-methoxy-2,3-dihydro-[1,4]dioxino[2,3-f]quinazolin-10-yl)amino)phenyl)-3-cyclobutylurea

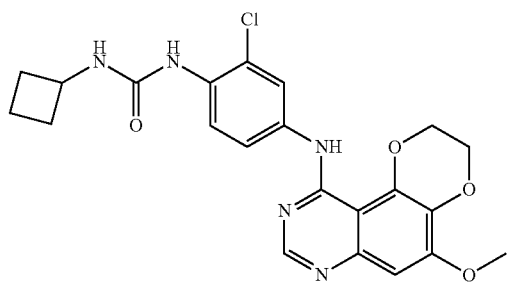 [SMILES: COc1cc2ncnc(Nc3ccc(NC(=O)NC4CCC4)c(Cl)c3)c2c2c1OCCO2]

According to the same procedure in Example 1, the target product as a yellow solid was obtained from the reaction of 10-chloro-5-methoxy-2,3-dihydro-[1,4]dioxino[2,3-f]quinazoline and 1-(4-amino-2-chlorophenyl)-3-cyclobutylurea, with a yield of 55%, $^1$HNMR (CD$_3$OD+DMSO-d$_6$(1:1), 400 MHz) δ ppm: 1.61-1.64 (2H, m), 1.80-1.86 (2H, m), 2.20-2.22 (2H, m), 3.94 (3H, s), 4.10-4.15 (1H, m), 4.38-4.40 (2H, m), 4.55-4.57 (2H, br), 6.84 (1H, s), 7.43 (1H, d, J=8.0 Hz), 7.80 (1H, s), 8.10 (1H, d, J=8.0 Hz), 8.55 (1H, s); MS: 456[M+H]$^+$.

Example 28. 1-(2-chloro-4-((5-methoxy-2,3-dihydro-[1,4]dioxino[2,3-f]quinazolin-10-yl)amino)phenyl)-3-cyclopentylurea

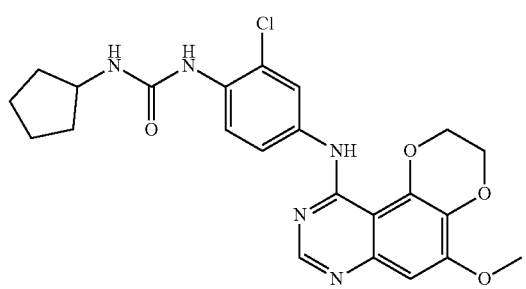 [SMILES: COc1cc2ncnc(Nc3ccc(NC(=O)NC4CCCC4)c(Cl)c3)c2c2c1OCCO2]

According to the same procedure in Example 1, the target product as a yellow solid was obtained from the reaction of 10-chloro-5-methoxy-2,3-dihydro-[1,4]dioxino[2,3-f]quinazoline and 1-(4-amino-2-chlorophenyl)-3-cyclopentylurea, with a yield of 58%;

$^1$HNMR (DMSO-d$_6$, 400 MHz) δ ppm: 1.38-1.42 (2H, m), 1.54-1.57 (4H, m), 1.82-1.85 (2H, m), 3.76-3.77 (1H, m), 3.98 (3H, s), 4.41-4.43 (2H, m), 4.59-4.61 (2H, m), 7.00 (1H, s), 7.20 (1H, d, J=8.0 Hz), 7.48 (1H, d, J=8.0 Hz), 7.83 (1H, s), 8.05 (1H, s), 8.23 (1H, d, J=8.0 Hz), 8.67 (1H, s), 10.30 (1H, s), MS: 470[M+H]$^+$.

Example 29. 1-(2-chloro-4-((5-methoxy-2,3-dihydro-[1,4]dioxino[2,3-f]quinazolin-10-yl)amino)phenyl)-3-cyclohexylurea

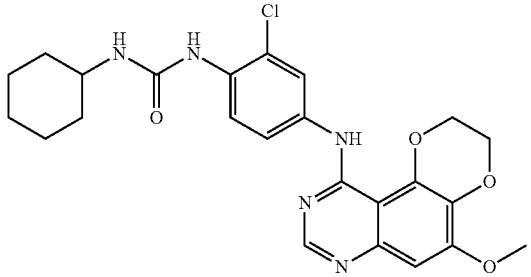 [SMILES: COc1cc2ncnc(Nc3ccc(NC(=O)NC4CCCCC4)c(Cl)c3)c2c2c1OCCO2]

According to the same procedure in Example 1, the target product as a yellow solid was obtained from the reaction of 10-chloro-5-methoxy-2,3-dihydro-[1,4]dioxino[2,3-f]quinazoline and 1-(4-amino-2-chlorophenyl)-3-cyclohexylurea, with a yield of 52%;

$^1$HNMR (DMSO-$d_6$, 400 MHz) δ ppm: 1.17-1.34 (6H, m), 1.66-1.70 (2H, m), 1.81-1.84 (2H, m), 3.76-3.77 (1H, m), 3.97 (3H, s), 4.42-4.44 (2H, m), 4.59-4.61 (2H, m), 7.05 (1H, s), 7.16 (1H, d, J=8.0 Hz), 7.47 (1H, d, J=8.0 Hz), 7.77 (1H, s), 8.12 (1H, d, J=8.0 Hz), 8.24 (1H, d, J=12.0 Hz), 8.74 (1H, s), 10.47 (1H, s) MS: 484[M+H]$^+$.

Example 30. 1-(2-chloro-4-((5-methoxy-2,3-dihydro-[1,4]dioxino[2,3-f]quinazolin-10-yl)amino)phenyl)-3-isopentylurea

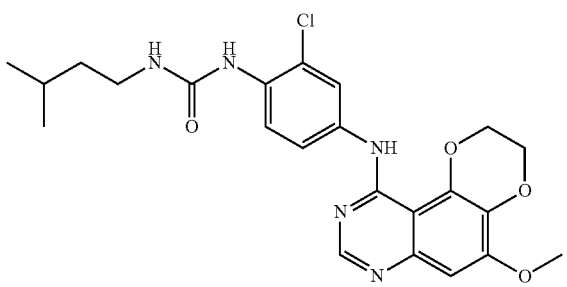 [SMILES: COc1cc2ncnc(Nc3ccc(NC(=O)NCCC(C)C)c(Cl)c3)c2c2c1OCCO2]

According to the same procedure in Example 1, the target product as a yellow solid was obtained from the reaction of 10-chloro-5-methoxy-2,3-dihydro-[1,4]dioxino[2,3-f]quinazoline and 1-(4-amino-2-chlorophenyl)-3-isopentylurea, with a yield of 46%;

$^1$HNMR (DMSO-$d_6$, 400 MHz) δ ppm: 0.91 (6H, d, J=6.8 Hz), 1.32-1.37 (2H, m), 1.62-1.65 (1H, m), 3.12-3.14 (2H, m), 3.98 (3H, s), 4.43-4.44 (2H, m), 4.59-4.60 (2H, m), 7.02 (1H, s), 7.12 (1H, s), 7.47 (1H, d, J=12.0 Hz), 7.77 (1H, s), 8.15 (1H, s), 8.23 (1H, d, J=12.0 Hz), 8.74 (1H, s), 10.47 (1H, s); MS: 472[M+H]$^+$.

Example 31. 1-(4-((5-(3-morpholinopropoxy)-2,3-dihydro-[1,4]dioxino[2,3-f]quinazolin-10-yl)oxy)phenyl)-3-(naphthalen-1-yl)urea

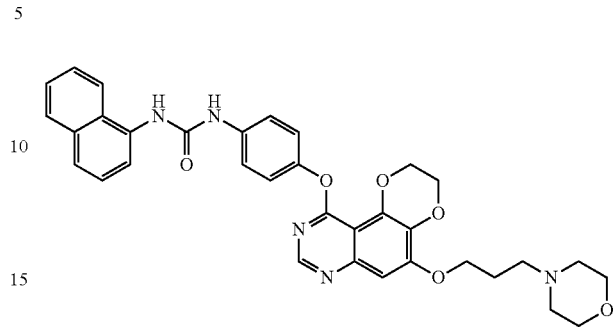

According to the same operation in Example 18, the target product as a yellow solid was obtained from the reaction of 10-chloro-5-(3-morpholinopropoxy)-2,3-dihydro-[1,4]dioxino[2,3-f]quinazoline and 1-(4-hydroxyphenyl)-3-(naphthalen-1-yl)urea, with a yield of 58%;

$^1$H NMR (DMSO-$d_6$, 300 MHz) δ 1.85-2.09 (2H, m), 2.23-2.47 (6H, m), 3.52-3.74 (4H, m), 4.21 (2H, d, J=6.8 Hz), 4.43 (4H, d, J=15.9 Hz), 7.04 (1H, s), 7.16 (2H, d, J=8.3 Hz), 7.43-7.70 (6H, m), 7.95 (1H, d, J=7.8 Hz), 8.04 (1H, d, J=7.4 Hz), 8.16 (1H, d, J=8.2 Hz), 8.43 (1H, d, J=3.3 Hz), 8.84 (1H, s), 9.20 (1H, s); MS: 608[M+H]$^+$.

Example 32. 1-(2-chloro-4-((5-methoxy-2,3-dihydro-[1,4]dioxino[2,3-f]quinazolin-10-yl)oxy)phenyl)-3-cyclopentylurea

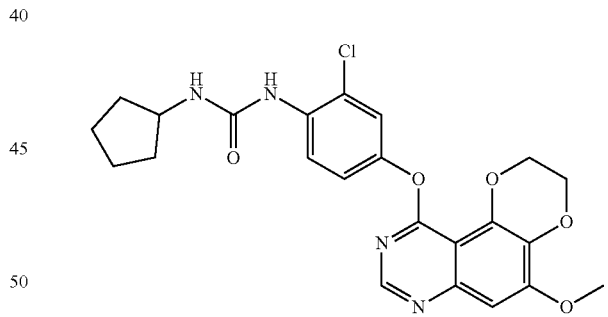

According to the same operation in Example 18, the target product as a yellow solid was obtained from the reaction of 10-chloro-5-methoxy-2,3-dihydro-[1,4]dioxino[2,3-f]quinazoline and 1-(2-chloro-4-hydroxyphenyl)-3-cyclopentylurea, with a yield of 58%;

$^1$H NMR (DMSO-$d_6$, 400 MHz) δ 1.34-1.46 (2H, m), 1.50-1.60 (2H, m), 1.61-1.72 (2H, m), 1.78-1.91 (2H, m), 1.95-2.04 (1H, m), 3.96 (3H, s), 4.34-4.41 (2H, m), 4.42-4.46 (2H, m), 7.02-7.08 (2H, m), 7.10-7.16 (1H, m), 7.39 (1H, d, J=2.7 Hz), 7.95 (1H, s), 8.20 (1H, d, J=9.0 Hz), 8.45 (1H, s); MS: 471[M+H]$^+$.

Example 33. 1-(2-chloro-4-((5-methoxy-2,3-di-hydro-[1,4]dioxino[2,3-f]quinazolin-10-yl)oxy)phenyl)-3-cyclohexylurea

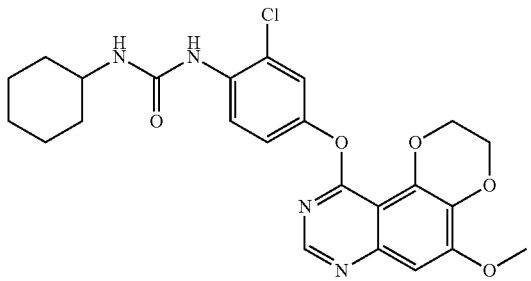 [SMILES: COc1cc2ncnc(Oc3ccc(NC(=O)NC4CCCCC4)c(Cl)c3)c2c2c1OCCO2]

According to the same operation in Example 18, the target product as a yellow solid was obtained from the reaction of 10-chloro-5-methoxy-2,3-dihydro-[1,4]dioxino[2,3-f]quinazoline and 1-(2-chloro-4-hydroxyphenyl)-3-cyclohexylurea, with a yield of 58%;

$^1$H NMR (DMSO-$d_6$, 400 MHz) δ 1.14-1.36 (6H, m), 1.61-1.74 (2H, m), 1.78-1.91 (2H, m), 3.44-3.58 (1H, m), 3.96 (3H, s), 4.32-4.56 (4H, m), 6.98 (1H, d, J=7.6 Hz), 7.05 (1H, s), 7.09-7.19 (1H, m), 7.38 (1H, d, J=2.7 Hz), 7.99 (1H, s), 8.19 (1H, d, J=9.0 Hz), 8.45 (1H, s); MS: 485[M+H]$^+$.

Example 34. Preparation of 1-(2-chloro-4-((5-(2-methoxyethoxy)-2,3-dihydro-[1,4]dioxino[2,3-f]quinazolin-10-yl)amino)phenyl)-3-cyclopropylurea

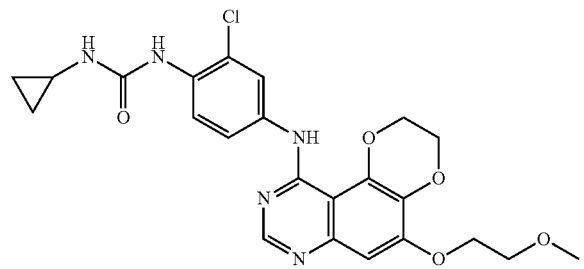 [SMILES: COCCOc1cc2ncnc(Nc3ccc(NC(=O)NC4CC4)c(Cl)c3)c2c2c1OCCO2]

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-cyclopropylurea, with a yield of 53%; $^1$HNMR (DMSO-$d_6$, 400 MHz) δ ppm: 0.42 (2H, br), 0.65 (2H, br), 2.52 (1H, br), 3.33 (3H, s), 3.72 (2H, br), 4.24 (2H, br), 4.41 (2H, br), 4.59 (2H, br), 6.91 (1H, s), 7.09 (1H, s), 7.40-7.46 (1H, m), 7.59 (1H, d, J=8.0 Hz), 7.85 (1H, s), 8.06-8.11 (1H, m), 8.40 (1H, s), 9.56 (1H, s); MS: 486[M+H]$^+$.

Example 35. Preparation of 1-(2-chloro-4-((5-(2-methoxyethoxy)-2,3-dihydro-[1,4]dioxino[2,3-f]quinazolin-10-yl)amino)phenyl)-3-(3-methoxyphenyl)urea

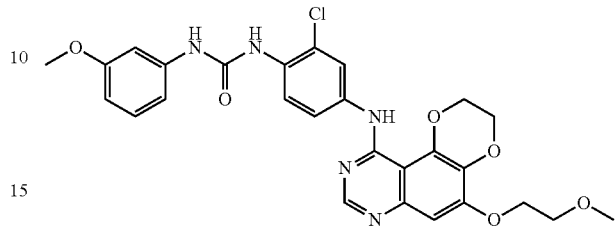

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(3-methoxyphenyl)urea, with a yield of 56%; $^1$H NMR (DMSO-$d_6$, 400 MHz) δ ppm: 3.34 (3H, s), 3.75 (3H, s), 3.76 (2H, br), 4.30 (2H, br), 4.45 (2H, br), 4.61 (2H, br), 6.59 (1H, d, J=12.0 Hz), 6.97-6.99 (2H, m), 7.18-7.21 (2H, m), 7.56 (1H, d, J=12.0 Hz), 7.87 (1H, s), 8.22 (1H, d, J=8.0 Hz), 8.51 (1H, s), 8.72 (1H, s), 9.68 (1H, s), 10.48 (1H, s); MS: 552[M+H]$^+$.

Example 36. Preparation of 1-(2-chloro-4-((5-(2-methoxyethoxy)-2,3-dihydro-[1,4]dioxino[2,3-f]quinazolin-10-yl)amino)phenyl)-3-(pyridin-2-yl)urea

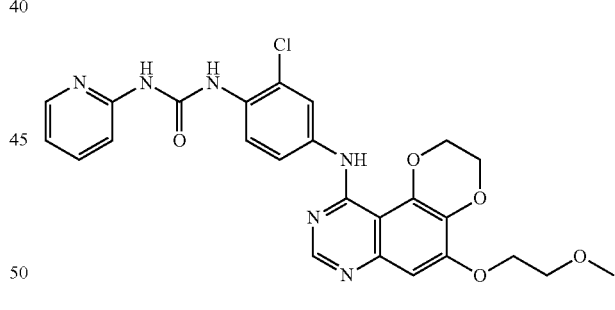

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(pyridin-2-yl)urea, with a yield of 52%; 1H NMR (DMSO-$d_6$, 400 MHz) δ ppm: 3.35 (3H, s), 3.76 (2H, br), 4.29 (2H, br), 4.46 (2H, br), 4.62 (2H, br), 7.01 (2H, s), 7.06 (1H, t, J=8.0 Hz), 7.26 (1H, d, J=8.0 Hz), 7.59 (1H, d, J=8.0 Hz), 7.80 (1H, t, J=8.0 Hz), 7.92 (1H, s), 8.33 (1H, s), 8.41 (1H, d, J=8.0 Hz), 8.73 (1H, s), 10.07 (1H, s), 10.46 (1H, s); MS: 523[M+H]$^+$.

Example 37. Preparation of 1-(2-chloro-4-((5-(2-methoxyethoxy)-2,3-dihydro-[1,4]dioxino[2,3-f]quinazolin-10-yl)amino)phenyl)-3-phenylurea

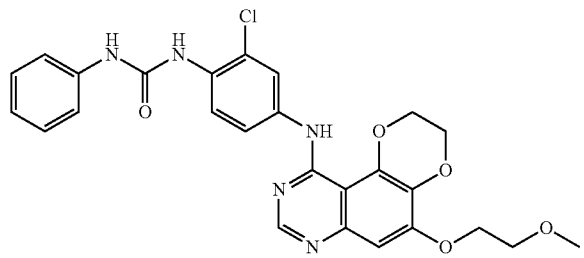 [SMILES: COCCOc1cc2ncnc(Nc3ccc(NC(=O)Nc4ccccc4)c(Cl)c3)c2c2c1OCCO2]

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-phenylurea, with a yield of 62%; 1H NMR (DMSO-$d_6$, 400 MHz) δ ppm: 3.34 (3H, s), 3.76 (2H, br), 4.29 (2H, br), 4.46 (2H, br), 4.62 (2H, br), 6.98-7.04 (2H, m), 7.29-7.32 (2H, m), 7.49-7.51 (3H, m), 7.85 (1H, s), 8.23 (1H, d, J=8.0 Hz), 8.58 (1H, s), 8.73 (1H, s), 9.79 (1H, s), 10.47 (1H, s); MS: 522[M+H]$^+$.

Example 38. Preparation of 1-(2-chloro-4-((5-(2-methoxyethoxy)-2,3-dihydro-[1,4]dioxino[2,3-f]quinazolin-10-yl)amino)phenyl)-3-(4-fluorophenyl)urea

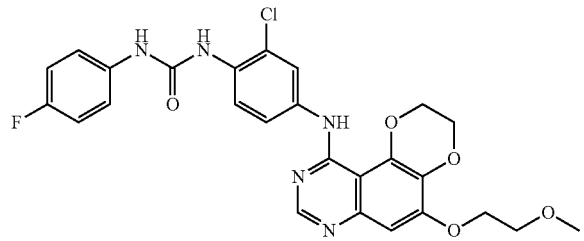 [SMILES: COCCOc1cc2ncnc(Nc3ccc(NC(=O)Nc4ccc(F)cc4)c(Cl)c3)c2c2c1OCCO2]

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(4-fluorophenyl)urea, with a yield of 55%; 1HNMR (DMSO-$d_6$, 400 MHz) δ ppm: 3.32 (3H, s), 3.73 (2H, br), 4.25 (2H, br), 4.40 (2H, br), 4.59 (2H, br), 6.90 (1H, s), 7.12-7.16 (2H, m), 7.49 (2H, br), 7.64-7.68 (1H, m), 8.07-8.09 (1H, m), 8.18 (1H, s), 8.26 (1H, s), 8.42 (1H, s), 9.36 (1H, s), 9.59 (1H, s); MS: 540[M+H]$^+$.

Example 39. Preparation of 1-(2-chloro-4-((5-(2-methoxyethoxy)-2,3-dihydro-[1,4]dioxino[2,3-f]quinazolin-10-yl)amino)phenyl)-3-(3-methylisoxazol-5-yl)urea

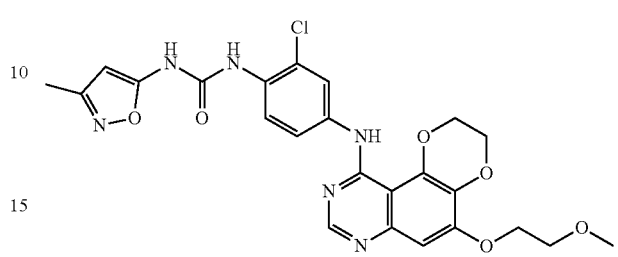

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(3-methylisoxazol-5-yl)urea, with a yield of 65%; 1H NMR (DMSO-$d_6$, 400 MHz) δ ppm: 2.38 (3H, s), 3.34 (3H, s), 3.76 (2H, s), 4.29 (2H, s), 4.46 (2H, s), 4.62 (2H, s), 6.51 (1H, s), 7.03 (1H, s), 7.58 (1H, d, J=12.0 Hz), 7.88 (1H, s), 8.20 (1H, d, J=12.0 Hz), 8.74 (1H, s), 8.90 (1H, s), 10.31 (1H, s), 10.48 (1H, s); MS: 527[M+H]$^+$.

Example 40. Preparation of 1-(2-chloro-4-((5-(2-methoxyethoxy)-2,3-dihydro-[1,4]dioxino[2,3-f]quinazolin-10-yl)amino)phenyl)-3-isopropylurea

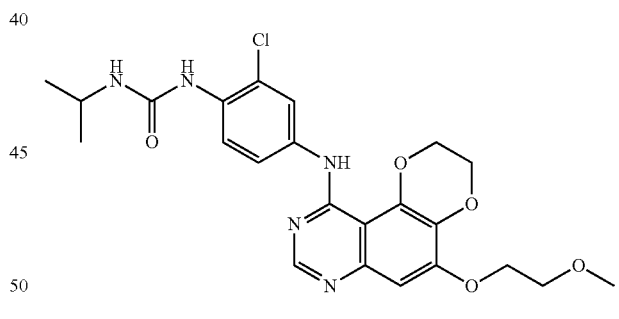

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-isopropylurea, with a yield of 58%; $^1$H NMR (DMSO-$d_6$, 400 MHz) δ ppm: 1.12 (6H, d, J=6.0 Hz), 3.34 (3H, s), 3.74 (2H, br), 3.77 (1H, p, J=6.0 Hz), 4.27 (2H, br), 4.43 (2H, br), 4.59 (2H, br), 6.90 (1H, s), 6.94 (1H, d, J=8.0 Hz), 7.51 (1H, d, J=12 Hz), 7.94 (2H, d, J=8.0 Hz), 8.19 (1H, d, J=12 Hz), 8.58 (1H, s), 10.04 (1H, s); MS: 488[M+H]$^+$.

Example 41. Preparation of 1-(2-chloro-4-((5-(2-methoxyethoxy)-2,3-dihydro-[1,4]dioxino[2,3-f]quinazolin-10-yl)amino)phenyl)-3-(2-methoxypyridin-4-yl)urea

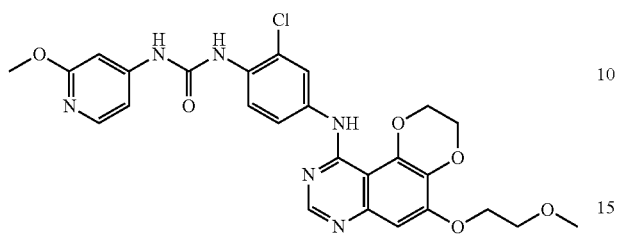

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(2-methoxypyridin-4-yl)urea, with a yield of 62%; 1H NMR (DMSO-d$_6$, 400 MHz) δ ppm: 3.34 (3H, s), 3.77 (2H, br), 3.84 (3H, s), 4.31 (2H, br), 4.46 (2H, br), 4.62 (2H, br), 6.95-6.98 (2H, m), 7.06 (1H, t, J=8.0 Hz), 7.58 (1H, d, J=8.0 Hz), 7.88 (1H, s), 8.02 (1H, d, J=4.0 Hz), 8.18 (1H, t, J=12.0 Hz), 8.69 (1H, s), 8.74 (1H, s), 10.08 (1H, s), 10.49 (1H, s); MS: 553[M+H]$^+$.

Example 42. Preparation of 1-(2-chloro-4-((5-(2-methoxyethoxy)-2,3-dihydro-[1,4]dioxino[2,3-f]quinazolin-10-yl)amino)phenyl)-3-(4-chloro-3-(trifluoromethyl)phenyl)urea

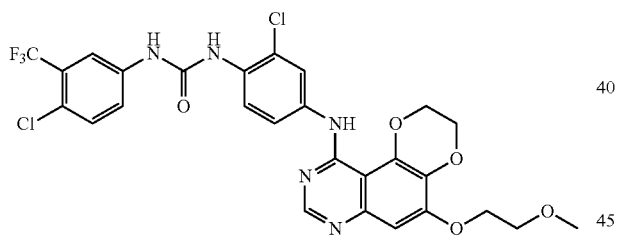

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(4-chloro-3-(trifluoromethyl) phenyl)urea, with a yield of 47%; 1H NMR (DMSO-d$_6$, 400 MHz) δ ppm: 3.34 (3H, s), 3.74 (2H, br), 4.26 (2H, br), 4.43 (2H, br), 4.61 (2H, br), 6.93 (1H, s), 7.62-7.65 (3H, m), 8.07-8.14 (3H, m), 8.55-8.57 (2H, m), 9.96 (1H, s), 10.05 (1H, s); MS: 624[M+H]$^+$.

Example 43. Preparation of 1-(2-chloro-4-((5-(2-methoxyethoxy)-2,3-dihydro-[1,4]dioxino[2,3-f]quinazolin-10-yl)amino)phenyl)-3-(2-fluoro-4-(trifluoromethyl)phenyl)urea

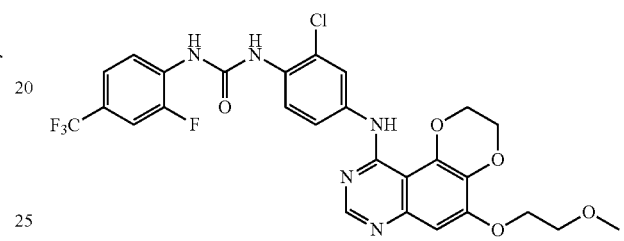

According to the same procedure in Example 1, the target product as a yellow solid was obtained from the reaction of 10-chloro-5-(2-methoxyethoxy)-2,3-dihydro-[1,4]dioxino[2,3-f]quinazoline and 1-(4-amino-2-chlorophenyl)-3-(2-fluoro-4-(trifluoromethyl) phenyl)urea, with a yield of 41%; 1H NMR (DMSO-d$_6$, 400 MHz) δ ppm: 3.33 (3H, s), 3.73 (2H, br), 4.26 (2H, br), 4.42 (2H, br), 4.60 (2H, br), 6.92 (1H, s), 7.42 (1H, s), 7.50-7.52 (1H, m), 7.67 (1H, d, J=8.0 Hz), 8.08 (1H, d, J=8.0 Hz), 8.21 (1H, s), 8.43 (1H, s), 8.65-8.66 (1H, m), 8.90 (1H, s), 9.62 (2H, s); MS: 608[M+H]$^+$.

Example 44. Preparation of 1-(2-chloro-4-((5-(2-methoxyethoxy)-2,3-dihydro-[1,4]dioxino[2,3-f]quinazolin-10-yl)amino)phenyl)-3-(4-(phenoxy)phenyl)urea

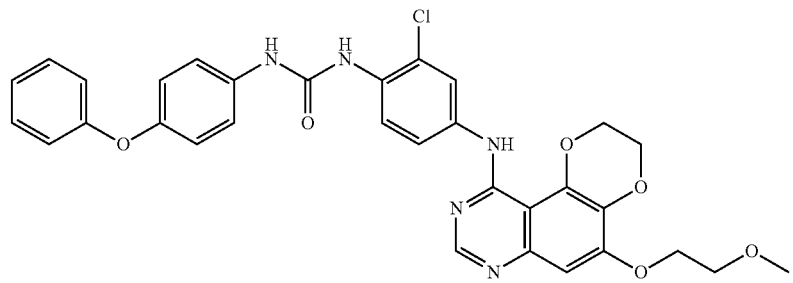 [SMILES: COCCOc1cc2ncnc(Nc3ccc(NC(=O)Nc4ccc(Oc5ccccc5)cc4)c(Cl)c3)c2c2c1OCCO2]

According to the same procedure in Example 1, a yellow solid was obtained from 10-chloro-5-(2-methoxyethoxy)-2,3-dihydro-[1,4]dioxino[2,3-f]quinazoline and 1-(2-chloro-4-aminophenyl)-3-(4-(phenoxy)phenyl)urea, with a yield of 62%; ¹HNMR (DMSO-d₆, 400 MHz) δ ppm: 3.33 (3H, s), 3.73 (2H, br), 4.25 (2H, br), 4.42 (2H, br), 4.60 (2H, br), 6.91 (1H, s), 6.96-7.02 (4H, m), 7.10-7.12 (1H, m), 7.37 (2H, t, J=8.0 Hz), 7.49-7.51 (2H, m), 7.63-7.66 (1H, m), 8.10-8.16 (2H, m), 8.28 (1H, s), 8.45 (1H, s), 9.38 (1H, s), 9.67 (1H, s); MS: 614[M+H]⁺.

Example 45. Preparation of 1-(2-chloro-4-((5-(2-methoxyethoxy)-2,3-dihydro-[1,4]dioxino[2,3-f]quinazolin-10-yl)oxy)phenyl)-3-cyclopropylurea

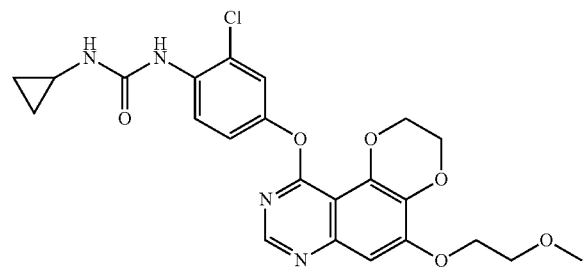 [SMILES: COCCOc1cc2ncnc(Oc3ccc(NC(=O)NC4CC4)c(Cl)c3)c2c2c1OCCO2]

According to the same operation in Example 18, a white solid was obtained from the reaction of the compound 10-chloro-5-(2-methoxyethoxy)-2,3-dihydro-[1,4]dioxino[2,3-f]quinazoline and 1-(2-chloro-4-hydroxyphenyl)-3-cyclopropylurea, with a yield of 48%; 1H NMR (DMSO-d₆, 400 MHz) δ 0.43 (2H, d, J=5.1 Hz), 0.67 (2H, d, J=5.1 Hz), 2.57 (1H, dd, J=6.9, 3.4 Hz), 3.39 (3H, s), 3.68-3.81 (2H, m), 4.22-4.33 (2H, m), 4.36-4.50 (4H, m), 7.06 (1H, s), 7.12-7.22 (2H, m), 7.39 (1H, d, J=2.6 Hz), 7.92 (1H, s), 8.17 (1H, d, J=9.1 Hz), 8.44 (1H, s); MS: 487[M+H]⁺.

Example 46. Preparation of 1-(4-chloro-3-(trifluoromethyl)phenyl)-3-(4-((5-(2-methoxyethoxy)-2,3-dihydro-[1,4]dioxino[2,3-f]quinazolin-10-yl)oxy)phenyl)urea

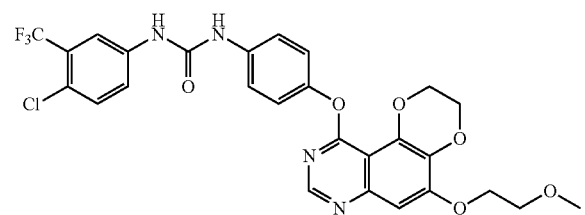 [SMILES: COCCOc1cc2ncnc(Oc3ccc(NC(=O)Nc4ccc(Cl)c(C(F)(F)F)c4)cc3)c2c2c1OCCO2]

According to the same operation in Example 18, a pale yellow solid was obtained from the reaction of 1-(4-chloro-3-(trifluoromethyl)phenyl)-3-(4-hydroxyphenyl)urea and 10-chloro-5-(2-methoxyethoxy)-2,3-dihydro-[1,4]dioxino[2,3-f]quinazoline, with a yield of 62%; 1H NMR (DMSO-d₆, 400 MHz) δ 3.37 (3H, s), 3.71-3.80 (2H, m), 4.25-4.36 (2H, m), 4.43 (4H, dd, J=18.9, 4.5 Hz), 7.05 (1H, s), 7.16 (2H, d, J=8.9 Hz), 7.53 (2H, d, J=8.9 Hz), 7.65 (2H, d, J=15.8 Hz), 8.13 (1H, d, J=2.2 Hz), 8.42 (1H, s), 8.92 (1H, s), 9.19 (1H, s); MS: 591[M+H]⁺.

Example 47. Preparation of 1-(2-fluoro-5-(trifluoromethyl)phenyl)-3-(4-((5-(2-methoxyethoxy)-2,3-dihydro-[1,4]dioxino[2,3-f]quinazolin-10-yl)oxy)phenyl)urea

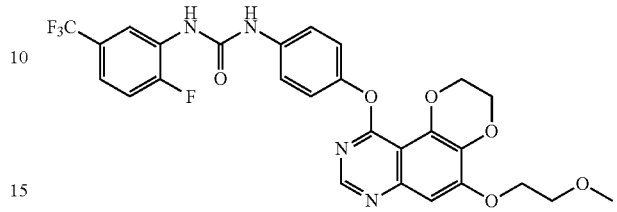

According to the same operation in Example 18, the target product as a white solid was obtained from the reaction of 1-(2-fluoro-5-(trifluoromethyl)phenyl)-3-(4-hydroxyphenyl)urea and 10-chloro-5-(2-methoxyethoxy)phenyl)-2,3-dihydro-[1,4]dioxino[2,3-f]quinazoline, with a yield of 59%; 1H NMR (DMSO-d₆, 400 MHz) δ3.40 (3H, s), 3.71-3.77 (2H, m), 4.26-4.34 (2H, m), 4.43 (4H, d, J=7.1 Hz), 7.06 (1H, s), 7.17 (2H, d, J=8.9), 7.40 (1H, d, J=2.5 Hz), 7.53 (3H, dd, J=9.7, 2.8 Hz), 8.42 (1H, s), 8.63 (1H, dd, J=7.4, 2.1 Hz), 8.91 (1H, d, J=2.8 Hz), 9.25 (1H, s); MS: 575[M+H]⁺.

Example 48. Preparation of 1-(4-chloro-3-(trifluoromethyl)phenyl)-3-(2-fluoro-4-((5-(2-methoxyethoxy)-2,3-dihydro-[1,4]dioxino[2,3-f]quinazolin-10-yl)oxy)phenyl)urea

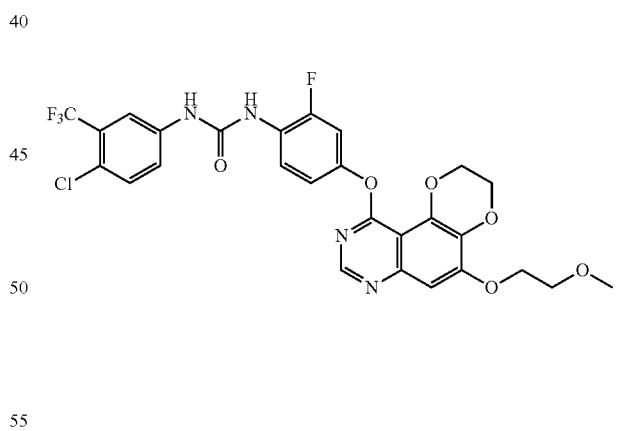

According to the same operation in Example 18, the target product as a grey solid was obtained from the reaction of 1-(4-chloro-3-(trifluoromethyl)phenyl)-3-(2-fluoro-4-hydroxyphenyl)urea and 10-chloro-5-(2-methoxyethoxy)-2,3-dihydro-[1,4]dioxino[2,3-f]quinazoline, with a yield of 67%; 1H NMR (DMSO-d₆, 400 MHz) δ3.40 (3H, s), 3.71-3.78 (2H, m), 4.23-4.34 (2H, m), 4.43 (4H, d, J=19.0 Hz), 7.07 (2H, s), 7.23 (1H, d, J=11.7 Hz), 7.63 (2H, s), 8.09 (2H, d, J=20.2 Hz), 8.45 (1H, s), 8.69 (1H, s), 9.50 (1H, s); MS: 609[M+H]⁺.

Example 49. Preparation of 1-(2,4-difluorophenyl)-3-(2-fluoro-4-((5-(2-methoxyethoxy)-2,3-dihydro-[1,4]dioxino[2,3-f]quinazolin-10-yl)oxy)phenyl)urea

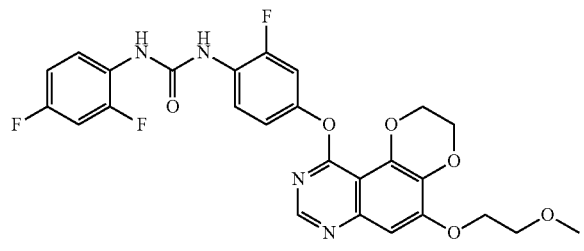 [SMILES: COCCOc1cc2ncnc(Oc3ccc(NC(=O)Nc4ccc(F)cc4F)c(F)c3)c2c2c1OCCO2]

According to the same operation in Example 18, the target product as a pale purple solid was obtained from the reaction of 1-(2,4-difluorophenyl)-3-(2-fluoro-4-hydroxyphenyl)urea and 10-chloro-5-(2-methoxyethoxy)-2,3-dihydro-[1,4]dioxino[2,3-f]quinazoline, with a yield of 63%; 1H NMR (DMSO-$d_6$, 400 MHz) δ 3.37 (3H, s), 3.69-3.80 (2H, m), 4.25-4.36 (2H, m), 4.25-4.51 (4H, m), 7.02-7.08 (3H, m), 7.26-7.38 (2H, m), 8.15 (2H, d, J=16.6 Hz), 8.45 (1H, s), 8.99 (2H, d, J=9.5 Hz); MS: 543[M+H]$^+$.

Example 50. Preparation of 1-(4-((5-(2-methoxyethoxy)-2,3-dihydro-[1,4]dioxino[2,3-f]quinazolin-10-yl)oxy)phenyl)-3-(3-methoxyphenyl)urea

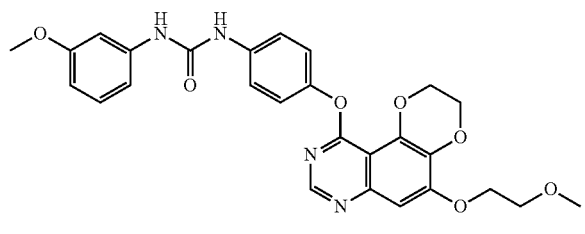

According to the same operation in Example 18, the target product as a pale yellow solid was obtained from the reaction of 10-chloro-5-(2-methoxyethoxy)-2,3-dihydro-[1,4]dioxino[2,3-f]quinazoline and 1-(4-hydroxyphenyl)-3-(3-methoxyphenyl)urea, with a yield of 61%; $^1$HNMR (DMSO-$d_6$, 400 MHz) δ ppm: 3.35 (3H, s), 3.74 (3H, s), 3.75 (2H, s), 4.30 (2H, s), 4.40 (2H, s), 4.45 (2H, s), 6.56 (1H, d, J=8.0 Hz), 6.95 (1H, d, J=8.0 Hz), 7.06 (1H, s), 7.13-7.16 (2H, m), 7.18-7.21 (2H, m), 7.51 (2H, d, J=8.0 Hz), 8.42 (1H, s), 8.73 (1H, s), 8.76 (1H, s); MS: 519[M+H]$^+$.

Example 51. Preparation of 1-(3-chloro-4-((5-(2-methoxyethoxy)-2,3-dihydro-[1,4]dioxino[2,3-f]quinazolin-10-yl)oxy)phenyl)-3-(3-methoxyphenyl)urea

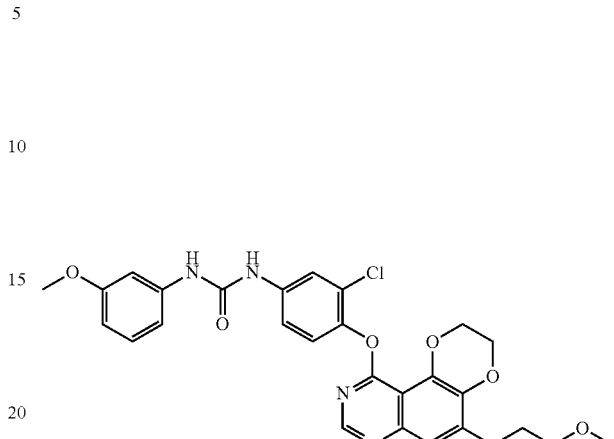

According to the same operation in Example 18, the target product as a pale yellow solid was obtained from the reaction of 10-chloro-5-(2-methoxyethoxy)-2,3-dihydro-[1,4]dioxino[2,3-f]quinazoline and 1-(3-chloro-4-hydroxyphenyl)-3-(3-methoxyphenyl)urea, with a yield of 49%; $^1$HNMR (DMSO-$d_6$, 400 MHz) δ ppm: 3.34 (3H, s), 3.74 (3H, s), 3.76 (2H, s), 4.31 (2H, s), 4.42 (2H, s), 4.47 (2H, s), 6.58 (1H, d, J=8.0 Hz), 6.95 (1H, d, J=8.0 Hz), 7.09 (1H, s), 7.17-7.21 (2H, m), 7.30-7.35 (2H, m), 7.84 (1H, s), 8.44 (1H, s), 8.86 (1H, s), 8.99 (1H, s); MS: 553[M+H]$^+$.

Example 52. Preparation of 1-(4-((5-(2-methoxyethoxy)-2,3-dihydro-[1,4]dioxino[2,3-f]quinazolin-10-yl)oxy)phenyl)-3-(2-methoxypyridin-4-yl)urea

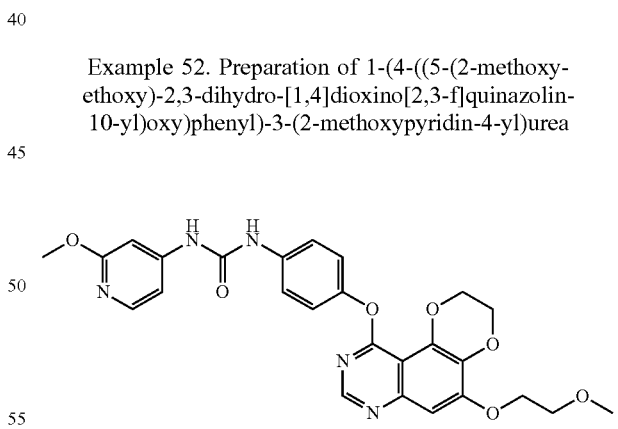

According to the same operation in Example 18, the target product as a pale yellow solid was obtained from the reaction of 10-chloro-5-(2-methoxyethoxy)-2,3-dihydro-[1,4]dioxino[2,3-f]quinazoline and 1-(4-hydroxyphenyl)-3-(2-methoxypyridin-4-yl)urea, with a yield of 51%; 1H NMR (DMSO-$d_6$, 400 MHz) δ ppm: 3.34 (3H, s), 3.75 (2H, s), 3.82 (3H, s), 4.30 (2H, s), 4.41 (2H, s), 4.46 (2H, s), 6.97 (1H, d, J=4.0 Hz), 6.98 (1H, s), 7.06 (1H, s), 7.16 (2H, d, J=8.0 Hz), 7.52 (2H, d, J=8.0 Hz), 7.97 (1H, d, J=8.0 Hz), 8.42 (1H, s), 9.11 (1H, s), 9.31 (1H, s); MS: 520[M+H]$^+$

Example 53. Preparation of 1-(3-chloro-4-((5-(2-methoxyethoxy)-2,3-dihydro-[1,4]dioxino[2,3-f]quinazolin-10-yl)oxy)phenyl)-3-(2-methoxypyridin-4-yl)urea

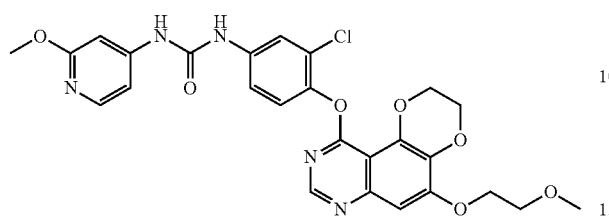

According to the same operation in Example 18, the target product as a pale yellow solid was obtained from the reaction of 10-chloro-5-(2-methoxyethoxy)-2,3-dihydro-[1,4]dioxino[2,3-f]quinazoline and 1-(3-chloro-4-hydroxyphenyl)-3-(2-methoxypyridin-4-yl) urea, with a yield of 54%; 1H NMR (DMSO-$d_6$, 400 MHz) δ ppm: 3.34 (3H, s), 3.75 (2H, s), 3.82 (3H, s), 4.31 (2H, s), 4.42 (2H, s), 4.47 (2H, s), 6.98 (1H, d, J=4.0 Hz), 6.99 (1H, s), 7.08 (1H, s), 7.33-7.38 (2H, m), 7.82 (1H, s), 7.98 (1H, d, J=8.0 Hz), 8.44 (1H, s), 9.21 (1H, s), 9.32 (1H, s); MS: 554[M+H]$^+$.

Example 54. Preparation of 1-(2-chloro-4-((5-(2-methoxyethoxy)-2,3-dihydro-[1,4]dioxino[2,3-f]quinazolin-10-yl)oxy)phenyl)-3-cyclobutylurea

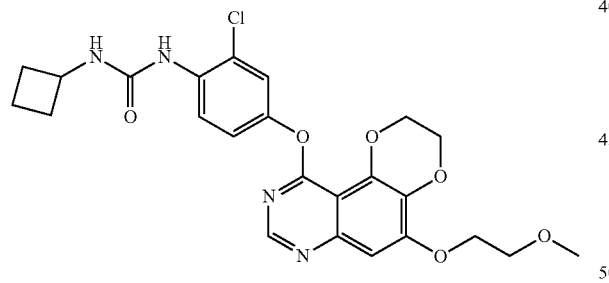

According to the same operation in Example 18, the target product as white solid was obtained from the reaction of 10-chloro-5-(2-methoxyethoxy)-2,3-dihydro-[1,4]dioxino[2,3-f]quinazoline and 1-(4-hydroxy-2-chlorophenyl)-3-cyclobutylurea, with a yield of 58%; 1H NMR (DMSO-$d_6$, 400 MHz) δ 1.56-1.72 (2H, m), 1.77-1.91 (2H, m), 2.15-2.30 (2H, m), 3.38 (3H, s), 3.74 (2H, s), 4.05-4.20 (1H, m), 4.23-4.33 (2H, m), 4.34-4.52 (4H, m), 7.05 (1H, s), 7.11-7.18 (1H, m), 7.27 (1H, d, J=7.8 Hz), 7.39 (1H, d, J=2.6 Hz), 7.95 (1H, s), 8.15 (1H, d, J=9.0 Hz), 8.44 (1H, s); MS: 501[M+H]$^+$.

Example 55. Preparation of 1-(2-chloro-4-((5-(2-methoxyethoxy)-2,3-dihydro-[1,4]dioxino[2,3-f]quinazolin-10-yl)oxy)phenyl)-3-cyclopentylurea

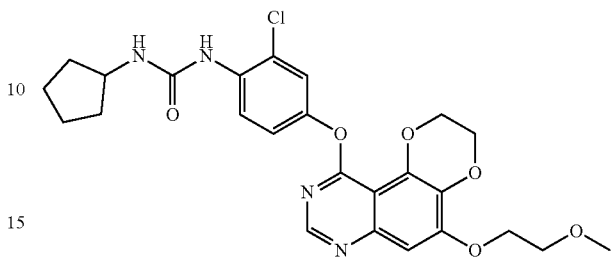

According to the same operation in Example 18, the target product as white solid was obtained from the reaction of 10-chloro-5-(2-methoxyethoxy)-2,3-dihydro-[1,4]dioxino[2,3-f]quinazoline and 1-(4-hydroxy-2-chlorophenyl)-3-cyclopentylurea, with a yield of 65%; $^1$H NMR (DMSO-$d_6$, 400 MHz) δ 1.33-1.46 (2H, m), 1.50-1.61 (2H, m), 1.62-1.72 (2H, m), 1.79-1.91 (2H, m), 3.34 (3H, s), 3.69-3.78 (2H, m), 3.88-4.04 (1H, m), 4.24-4.33 (2H, m), 4.36-4.56 (4H, m), 7.05 (2H, d, J=6.2 Hz), 7.10-7.22 (1H, m), 7.39 (1H, d, J=2.7 Hz), 7.94 (1H, s), 8.20 (1H, d, J=9.1 Hz), 8.44 (1H, s); MS: 515[M+H]$^+$.

Example 56. Preparation of 1-(2-chloro-4-((5-(2-methoxyethoxy)-2,3-dihydro-[1,4]dioxino[2,3-f]quinazolin-10-yl)oxy)phenyl)-3-cyclohexylurea

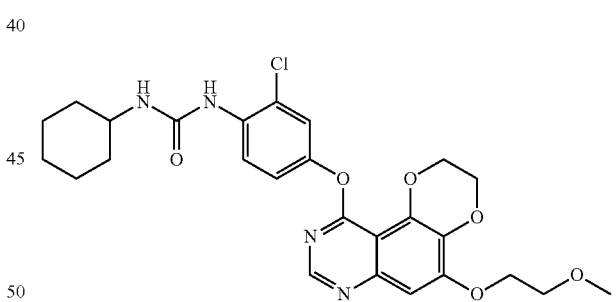

According to the same operation in Example 18, the target product as white solid was obtained from the reaction of 10-chloro-5-(2-methoxyethoxy)-2,3-dihydro-[1,4]dioxino[2,3-f]quinazoline and 1-(4-hydroxy-2-chlorophenyl)-3-cyclohexylurea, with a yield of 68%; 1H NMR (DMSO-$d_6$, 400 MHz) δ 1.13-1.35 (6H, m), 1.61-1.73 (2H, m), 1.75-1.90 (2H, m), 3.38 (3H, s), 3.50 (1H, d, J=9.8 Hz), 3.69-3.80 (2H, m), 4.22-4.33 (2H, m), 4.35-4.53 (4H, m), 6.99 (1H, d, J=7.6 Hz), 7.06 (1H, s), 7.10-7.18 (1H, m), 7.39 (1H, d, J=2.7 Hz), 7.99 (1H, s), 8.19 (1H, d, J=9.1 Hz), 8.44 (1H, s): MS: 529[M+H]$^+$.

Example 57. Preparation of 1-(2-fluoro-4-((5-(2-methoxyethoxy)-2,3-dihydro-[1,4]dioxino[2,3-f]quinazolin-10-yl)oxy)phenyl)-3-(2-fluoro-5-(trifluoromethyl)phenyl)urea

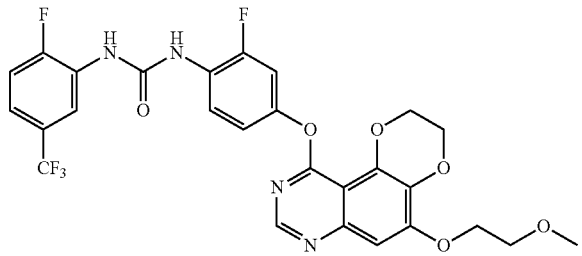 [SMILES: COCCOc1cc2ncnc(Oc3ccc(NC(=O)Nc4cc(C(F)(F)F)ccc4F)c(F)c3)c2c2c1OCCO2]

According to the same operation in Example 18, the target product as a white solid was obtained from the reaction of 10-chloro-5-(2-methoxyethoxy)-2,3-dihydro-[1,4]dioxino[2,3-f]quinazoline and 1-(2-fluoro-4-hydroxyphenyl)-3-(2-fluoro-5-(trifluoromethyl) phenyl)urea, with a yield of 42%; 1H NMR (DMSO-$d_6$, 400 MHz) δ 3.34 (3H, s), 3.67-3.79 (2H, m), 4.24-4.35 (2H, m), 4.36-4.52 (4H, m), 7.03-7.11 (2H, m), 7.31-7.38 (1H, m), 7.39-7.46 (1H, m), 7.48-7.60 (1H, m), 8.15-8.26 (1H, m), 8.46 (1H, s), 8.60-8.72 (1H, m), 9.24 (1H, d, J=2.3 Hz), 9.42 (1H, d, J=2.9 Hz); MS: 593[M+H]$^+$.

Example 58. Preparation of 1-(3-fluoro-4-((5-(2-methoxyethoxy)-2,3-dihydro-[1,4]dioxino[2,3-f]quinazolin-10-yl)oxy)phenyl)-3-(2-fluoro-5-(trifluoromethyl)phenyl)urea

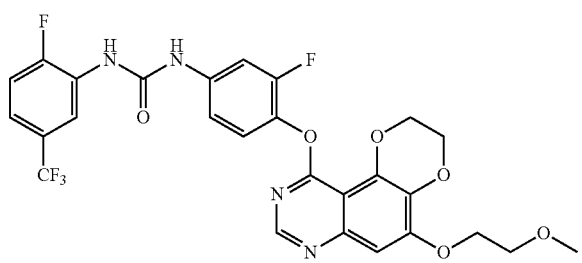 [SMILES: COCCOc1cc2ncnc(Oc3ccc(NC(=O)Nc4cc(C(F)(F)F)ccc4F)cc3F)c2c2c1OCCO2]

According to the same operation in Example 18, the target product as a white solid was obtained from the reaction of 10-chloro-5-(2-methoxyethoxy)-2,3-dihydro-[1,4]dioxino[2,3-f]quinazoline and 1-(3-fluoro-4-hydroxyphenyl)-3-(2-fluoro-5-(trifluoromethyl) phenyl)urea, with a yield of 46%; 1H NMR (DMSO-$d_6$, 400 MHz) δ 3.34 (3H, s), 3.69-3.80 (2H, m), 4.24-4.35 (2H, m), 4.37-4.60 (4H, m), 7.09 (1H, s), 7.18-7.24 (1H, m), 7.30-7.38 (1H, m), 7.40-7.47 (1H, m), 7.49-7.58 (1H, m), 7.63-7.78 (1H, m), 8.46 (1H, s), 8.57-8.74 (1H, m), 9.11 (1H, d, J=2.8 Hz), 9.72 (1H, s); MS: 593[M+H]$^+$.

Example 59. Preparation of 1-(4-chloro-3-(trifluoromethyl)phenyl)-3-(3-fluoro-4-((5-(2-methoxyethoxy)-2,3-dihydro-[1,4]dioxino[2,3-f]quinazolin-10-yl)oxy)phenyl)urea

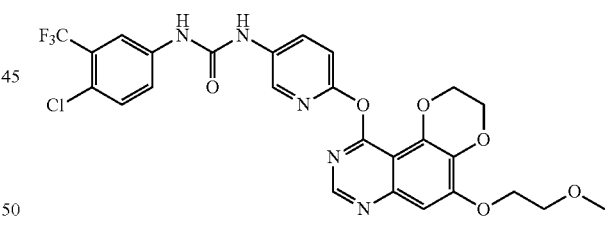

According to the same operation in Example 18, the target product as a white solid was obtained from the reaction of 10-chloro-5-(2-methoxyethoxy)-2,3-dihydro-[1,4]dioxino[2,3-f]quinazoline and 1-(4-chloro-3-(trifluoromethyl)phenyl)-3-(3-fluoro-4-hydroxy phenyl)urea, with a yield of 46%; 1H NMR (DMSO-$d_6$, 400 MHz) δ 3.34 (3H, s), 3.67-3.82 (2H, m), 4.26-4.36 (2H, m), 4.36-4.58 (4H, m), 7.09 (1H, s), 7.19-7.26 (1H, m), 7.29-7.40 (1H, m), 7.58-7.82 (3H, m), 8.12 (1H, d, J=2.4 Hz), 8.46 (1H, s), 9.44 (1H, s), 9.60 (1H, s); MS: 609[M+H]$^+$.

Example 60. Preparation of 1-(4-chloro-3-(trifluoromethyl)phenyl)-3-(6-((5-(2-methoxyethoxy)-2,3-dihydro-[1,4]dioxino[2,3-f]quinazolin-10-yl)oxy)pyridin-3-yl)urea According to the same operation in Example 18, the target product as a white solid was obtained from the reaction of 10-chloro-5-(2-methoxyethoxy)-2,3-dihydro-[1,4]dioxino[2,3-f]quinazoline and 1-(4-chloro-3-(trifluoromethyl)phenyl)-3-(6-hydroxylpyridin-3-yl)urea, with a yield of 44%; $^1$H NMR (DMSO-$d_6$, 300 MHz) δ 3.38 (3H, s), 3.67-3.81 (2H, m), 4.24-4.36 (2H, m), 4.36-4.57 (4H, m), 7.08 (1H, s), 7.25 (1H, d, J=8.9 Hz), 7.66 (2H, d, J=6.8 Hz), 8.09 (2H, d, J=20.4 Hz), 8.44 (2H, d, J=12.6 Hz), 9.35 (1H, s), 9.61 (1H, s); MS: 592[M+H]$^+$.

63

Example 61. Preparation of 1-(2-chloro-4-((5-(3-(pyrrolidin-1-yl)propoxy)-2,3-dihydro-[1,4]dioxino[2,3-f]quinazolin-10-yl)amino)phenyl)-3-cyclopropylurea

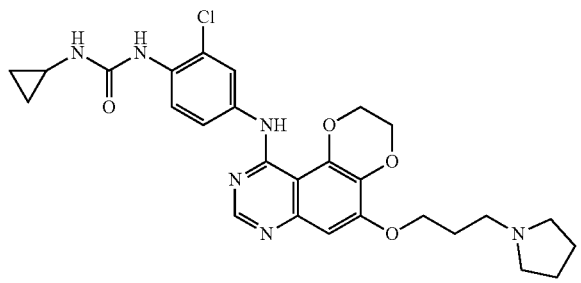 [SMILES: O=C(Nc1ccc(Oc2ncnc3cc(OCCCN4CCCC4)c4c(c23)OCCO4)cc1Cl)NC1CC1]

According to the same procedure in Example 1, the target product as a yellow solid was obtained from the reaction of 10-chloro-5-(3-(pyrrolidin-1-yl)propoxy)-2,3-dihydro-[1,4]dioxino[2,3-f]quinazoline and 1-(4-amino-2-chlorophenyl)-3-cyclopropylurea, with a yield of 48%; $^1$HNMR (DMSO-$d_6$, 400 MHz) δ ppm: 0.43 (2H, d, J=4.0 Hz), 0.66 (2H, d, J=4.0 Hz), 1.69 (4H, br), 1.95-2.01 (4H, m), 2.46 (4H, m), 2.56 (1H, m), 4.15-4.18 (2H, m), 4.41 (2H, br), 4.59 (2H, br), 6.86 (1H, s), 7.10 (1H, s), 7.59 (1H, d, J=8.0 Hz), 7.85 (1H, s), 8.08 (1H, d, J=8.0 Hz), 8.13 (1H, s), 8.40 (1H, s), 9.54 (1H, s); MS: 539[M+H]$^+$.

Example 62. Preparation of 1-(2-chloro-4-((5-(3-(pyrrolidin-1-yl)propoxy)-2,3-dihydro-[1,4]dioxino[2,3-f]quinazolin-10-yl)oxy)phenyl)-3-cyclopropylurea

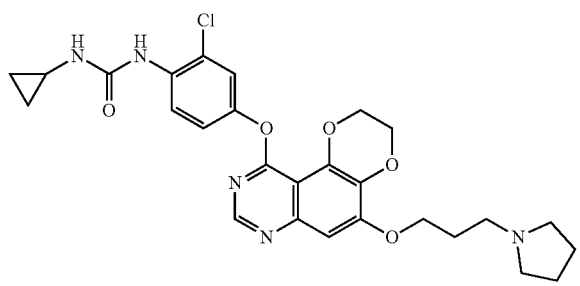

64

Step a) Preparation of 10-(3-chloro-4-nitrophenoxy)-5-(3-(pyrrolidin-1-yl)propoxy)-2,3-dihydro-[1,4]dioxino[2,3-f]quinazoline

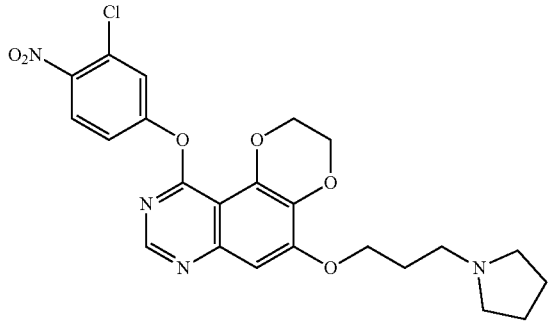 [SMILES: O=[N+]([O-])c1ccc(Oc2ncnc3cc(OCCCN4CCCC4)c4c(c23)OCCO4)cc1Cl]

10-chloro-5-(3-(pyrrolidin-1-yl)propoxy)-2,3-dihydro-[1,4]dioxino[2,3-f]quinazoline (35 mg, 0.1 mmol), 3-chloro-4-nitrophenol, potassium carbonate $K_2CO_3$ (20 mg, 0.15 mmol) were reacted in isopropanol (10 ml) at 80° C. for 3 h. After cooling, the reaction mixture was added with water and suction filtered to give 39 mg yellow solid, with a yield of 80%; MS: 487[M+H]$^+$.

Step b) Preparation of 2-chloro-4-((5-(3-(pyrrolidin-1-yl)propoxy)-2,3-dihydro-[1,4]dioxino[2,3-f]quinazolin-10-yl)oxy)aniline 10-(3-chloro-4-nitrophenoxy)-5-(3-(pyrrolidin-1-yl)propoxy)-2,3-dihydro-[1,4]dioxino[2,3-f]quinazoline (39 mg, 0.08 mmol) was dissolved in 5 mL methanol, 50 mg Raney nickel was added thereto, and the mixture was stirred for 2 h under hydrogen atmosphere. the reaction mixture was suction filtered and concentrated to give 36 mg product, with a yield of 99%. MS: 457[M+H]$^+$.

Step c) Preparation of 1-(2-chloro-4-((5-(3-(pyrrolidin-1-yl)propoxy)-2,3-dihydro-[1,4]dioxino[2,3-f]quinazolin-10-yl)oxy)phenyl)-3-cyclopropylurea 2-chloro-4-((5-(3-(pyrrolidin-1-yl)propoxy)-2,3-dihydro-[1,4]dioxino[2,3-f]quinazolin-10-yl)oxy)aniline (36 mg, 0.08 mmol) was dissolved in 5 mL dichloromethane, 0.2 mL triethylamine and triphosgene (29 mg, 0.1 mmol) were added and the mixture was stirred for 0.5 h. Cyclopropylamine (6 mg, 0.1 mmol) was added and the mixture was continuously stirred until the reaction was completed. After the reaction mixture was concentrated, and it was subjected to column chromatography, 34 mg product was obtained, with a yield of 80%. $^1$HNMR (DMSO-$d_6$, 400 MHz) δ ppm: 0.43 (2H, d, J=4.0 Hz), 0.67 (2H, d, J=4.0 Hz), 1.70 (4H, br), 1.95-1.99 (2H, m), 2.46 (4H, m), 2.57 (3H, m), 4.20-4.23 (2H, m), 4.42 (4H, d, J=10.0 Hz), 7.03 (1H, s), 7.13-7.16 (2H, m), 7.39 (1H, s), 7.92 (1H, s), 8.17 (1H, d, J=8.0 Hz), 8.44 (1H, s), MS: 540[M+H]$^+$.

Example 63. Preparation of 1-(2-chloro-4-((5-(3-(morpholinopropoxy)-2,3-dihydro-[1,4]dioxino[2,3-f]quinazolin-10-yl)amino)phenyl)-3-cyclopropylurea

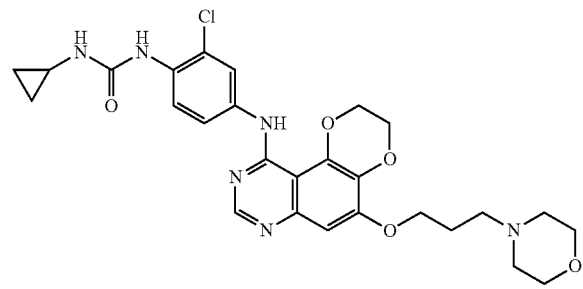 [SMILES: O=C(Nc1ccc(Nc2ncnc3cc(OCCCN4CCOCC4)c4c(c23)OCCO4)cc1Cl)NC1CC1]

According to the same procedure in Example 1, the target product as a yellow solid was obtained from the reaction of 10-chloro-5-(3-(morpholinopropoxy)-2,3-dihydro-[1,4]dioxino[2,3-f]quinazoline and 1-(4-amino-2-chlorophenyl)-3-cyclopropylurea, with a yield of 52%; 1H NMR (DMSO-$d_6$, 400 MHz) δ ppm: 0.42 (2H, d, J=8.0 Hz), 0.64 (2H, d, J=8.0 Hz), 1.95-2.01 (2H, m), 2.39-2.50 (4H, m), 2.55-2.57 (1H, m), 3.05-3.09 (4H, m), 3.60 (2H, br), 3.18 (2H, br), 4.40 (2H, br), 4.58 (2H, br), 6.87 (1H, s), 7.13 (1H, s), 7.59 (1H, d, J=8.0 Hz), 7.86 (1H, s), 8.07-8.12 (2H, m), 8.40 (1H, s), 9.55 (1H, s); MS: 555[M+H]$^+$.

Example 64. Preparation of 1-(2-chloro-4-((5-(3-(morpholinopropoxy)-2,3-dihydro-[1,4]dioxino[2,3-f]quinazolin-10-yl)oxy)phenyl)-3-cyclopropylurea

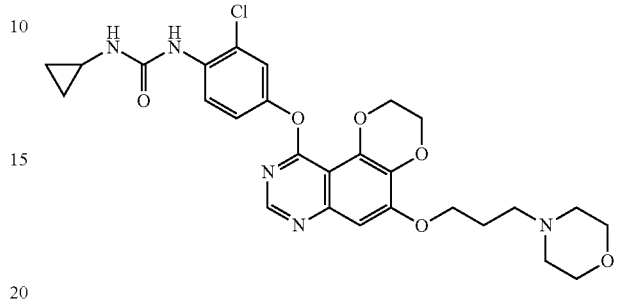

According to the same synthetic strategy in Example 62, but using 10-chloro-5-(3-(morpholinopropoxy)-2,3-dihydro-[1,4]dioxino[2,3-f]quinazoline as starting material, 25 mg target product was prepared, with a yield of 46%; $^1$HNMR (DMSO-$d_6$, 400 MHz) δ ppm: 0.43 (2H, d, J=8.0 Hz), 0.67 (2H, d, J=8.0 Hz), 1.95-1.98 (2H, m), 2.39 (4H, br), 2.47 (2H, t, J=8.0 Hz), 2.55-2.57 (1H, m), 3.59 (4H, t, J=4.0 Hz), 4.22 (2H, t, J=6.0 Hz), 4.42 (4H, d, J=20.0 Hz), 7.03 (1H, s), 7.13-7.16 (2H, m), 7.39 (1H, s), 7.92 (1H, s), 8.17 (1H, d, J=8.0 Hz), 8.44 (1H, s); MS: 556[M+H]$^+$.

Example 65. Preparation of 1-(2-fluoro-5-(trifluoromethyl)phenyl)-3-(4-((5-(3-morpholinopropoxy)-2,3-dihydro-[1,4]dioxino[2,3-f]quinazolin-10-yl)oxy)phenyl)urea

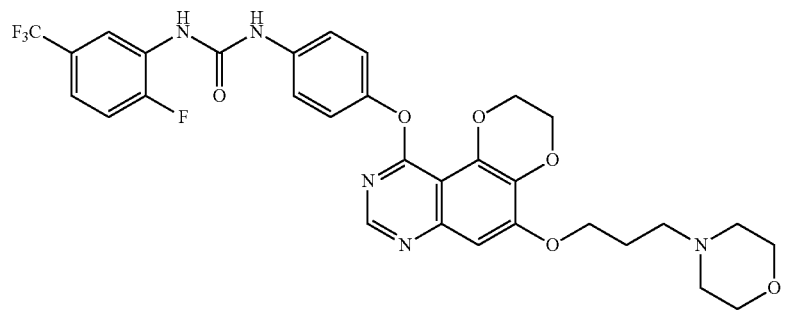 [SMILES: O=C(Nc1ccc(Oc2ncnc3cc(OCCCN4CCOCC4)c4c(c23)OCCO4)cc1)Nc1cc(C(F)(F)F)ccc1F]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(2-fluoro-5-(trifluoromethyl)phenyl)-3-(4-hydroxy phenyl)urea, with a yield of 45%; 1H NMR (DMSO-$d_6$, 400 MHz) δ1.91-2.09 (2H, m), 2.33-2.45 (4H, m), 3.05-3.10 (2H, m), 3.55-3.65 (4H, m), 4.16-4.32 (2H, m), 4.36-4.55 (4H, m), 7.05 (1H, s), 7.13-7.20 (2H, m), 7.35-7.44 (1H, m), 7.48-7.52 (1H, m), 7.52-7.58 (2H, m), 8.43 (1H, s), 8.64 (1H, dd, J=7.4, 2.4 Hz), 9.05 (1H, d, J=3.3 Hz), 9.52-9.56 (1H, m); MS: 644[M+H]$^+$.

Example 66. Preparation of 1-(4-chloro-3-(trifluoromethyl)phenyl)-3-(4-((5-(3-morpholinopropoxy)-2,3-dihydro-[1,4]dioxino[2,3-f]quinazolin-10-yl)oxy)phenyl)urea

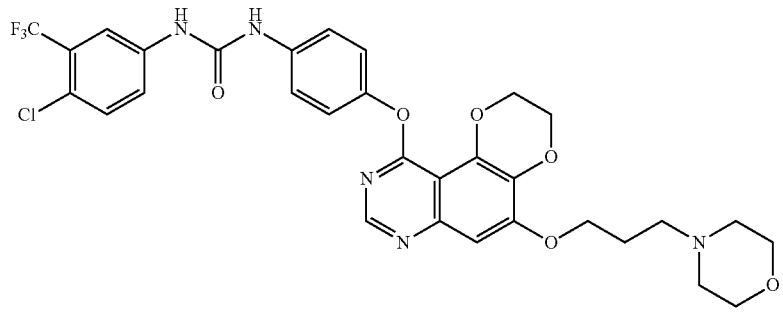 [SMILES: O=C(Nc1ccc(Oc2ncnc3cc(OCCCN4CCOCC4)c4c(c23)OCCO4)cc1)Nc1ccc(Cl)c(C(F)(F)F)c1]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(4-chloro-3-(trifluoromethyl)phenyl)-3-(4-hydroxy phenyl)urea, with a yield of 41%; $^1$H NMR (DMSO-$d_6$, 400 MHz) δ1.95-2.11 (2H, m), 2.33-2.50 (4H, m), 3.01-3.16 (2H, m), 3.64 (4H, br), 4.19-4.29 (2H, m), 4.36-4.57 (4H, m), 7.05 (1H, s), 7.11-7.21 (2H, m), 7.49-7.58 (2H, m), 7.61-7.69 (2H, m), 8.13 (1H, d, J=2.3 Hz), 8.43 (1H, s), 9.15 (1H, s), 9.46 (1H, s); MS: 660[M+H]$^+$.

Example 67. Preparation of 1-(3-fluoro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea

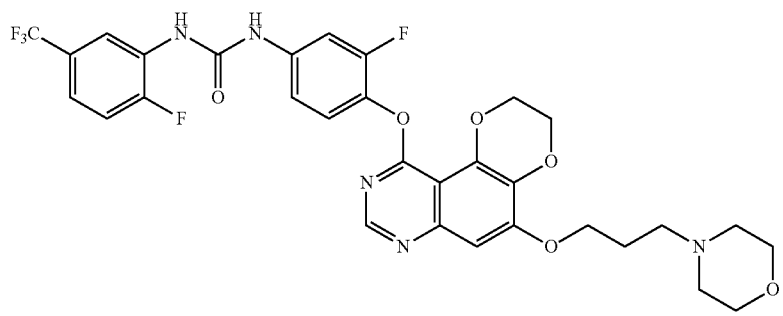 [SMILES: O=C(Nc1ccc(Oc2ncnc3cc(OCCCN4CCOCC4)c4c(c23)OCCO4)c(F)c1)Nc1cc(C(F)(F)F)ccc1F]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(2-fluoro-5-(trifluoromethyl)phenyl)-3-(3-fluoro-4-hydroxy phenyl)urea, with a yield of 47%; $^1$H NMR (DMSO-$d_6$, 400 MHz) δ 1.86-2.10 (2H, m), 2.35-2.46 (6H, m), 3.51-3.69 (4H, m), 4.16-4.28 (2H, m), 4.34-4.55 (4H, m), 7.07 (1H, s), 7.17-7.25 (1H, m), 7.31-7.37 (1H, m), 7.39-7.47 (1H, m), 7.49-7.58 (1H, m), 7.65-7.75 (1H, m), 8.46 (1H, s), 8.55-8.68 (1H, m), 9.09 (1H, d, J=3.2 Hz), 9.67 (1H, d, J=9.7 Hz); MS: 662[M+H]$^+$.

Example 68. Preparation of 1-(4-chloro-3-(trifluoromethyl)phenyl)-3-(3-fluoro-4-((5-(3-morpholinopropoxy)-2,3-dihydro-[1,4]dioxino[2,3-f]quinazolin-10-yl)oxy)phenyl)urea

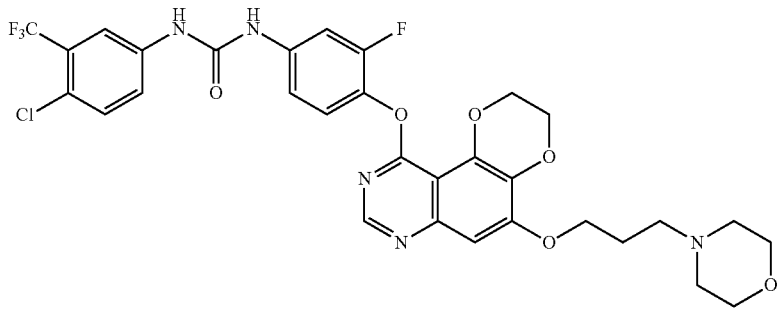 [SMILES: O=C(Nc1ccc(Oc2ncnc3cc(OCCCN4CCOCC4)c4c(c23)OCCO4)c(F)c1)Nc1ccc(Cl)c(C(F)(F)F)c1]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(4-chloro-3-(trifluoromethyl)phenyl)-3-(3-fluoro-4-hydroxy phenyl)urea, with a yield of 52%; 1H NMR (DMSO-$d_6$, 400 MHz) δ 1.92-2.02 (2H, m), 2.22-2.49 (6H, m), 3.51-3.71 (4H, m), 4.15-4.31 (2H, m), 4.31-4.57 (4H, m), 6.95-7.14 (2H, m), 7.22-7.44 (1H, m), 7.64 (2H, d, J=1.7 Hz), 8.03-8.23 (2H, m), 8.43 (1H, d, J=15.7 Hz), 8.79 (1H, d, J=2.2 Hz), 9.72 (1H, s); MS: 678[M+H]$^+$.

Example 69. Preparation of 1-(4-chloro-3-(trifluoromethyl)phenyl)-3-(2-fluoro-4-((5-(3-morpholinopropoxy)-2,3-dihydro-[1,4]dioxino[2,3-f]quinazolin-10-yl)oxy)phenyl)urea

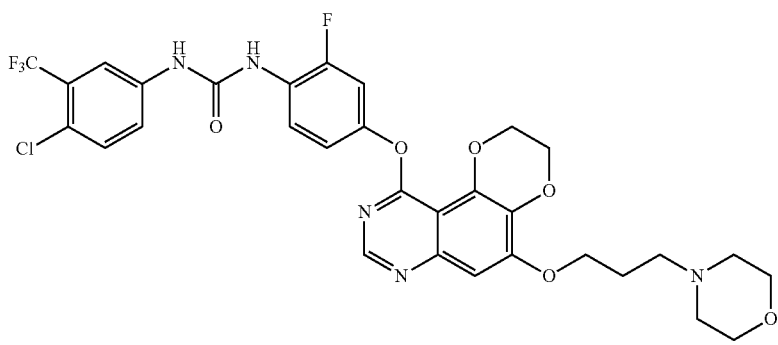 [SMILES: O=C(Nc1ccc(Cl)c(C(F)(F)F)c1)Nc1ccc(Oc2ncnc3cc(OCCCN4CCOCC4)c4c(c23)OCCO4)cc1F]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(4-chloro-3-(trifluoromethyl)phenyl)-3-(2-fluoro-4-hydroxy phenyl)urea, with a yield of 55%; 1H NMR (DMSO-$d_6$, 300 MHz) δ 1.85-2.07 (2H, m), 2.22-2.44 (6H, m), 3.50-3.73 (4H, m), 4.11-4.31 (2H, m), 4.31-4.57 (4H, m), 6.98-7.15 (2H, m), 7.32 (1H, d, J=11.7 Hz), 7.55-7.73 (2H, m), 8.02-8.20 (2H, m), 8.45 (1H, s), 8.79 (1H, s), 9.71 (1H, s); MS: 678[M+H]$^+$.

Example 70. Preparation of 1-(2-fluoro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea

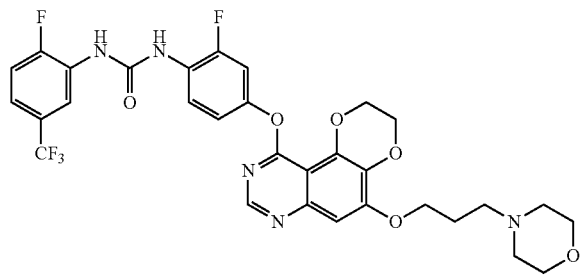 [SMILES: O=C(Nc1ccc(Oc2ncnc3cc(OCCCN4CCOCC4)c4c(c23)OCCO4)cc1F)Nc1cc(C(F)(F)F)ccc1F]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(2-fluoro-5-(trifluoromethyl)phenyl)-3-(2-fluoro-4-hydroxy phenyl)urea, with a yield of 45%, 1H NMR (400 MHz, DMSO-$d_6$) δ ppm 1.93-2.03 (2H, m), 2.39 (4H, s), 2.46 (2H, t, J=7.1 Hz), 3.59 (4H, t, J=4.7 Hz), 4.22 (2H, t, J=6.4 Hz), 4.37-4.48 (4H, m), 7.05 (1H, s), 7.02-7.10 (1H, m), 7.34 (1H, d, J=11.8 Hz), 7.43 (1H, s), 7.48-7.58 (1H, m), 8.19 (1H, t, J=9.1 Hz), 8.45 (1H, s), 8.66 (1H, d, J=7.4 Hz), 9.25 (1H, s), 9.43 (1H, d, J=2.8 Hz); MS: 662[M+H]$^+$.

Example 71. Preparation of 1-(2-chloro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea

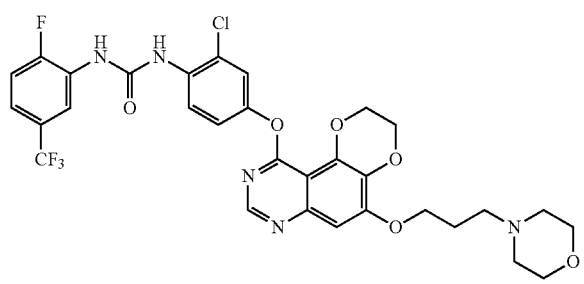 [SMILES: O=C(Nc1cc(C(F)(F)F)ccc1F)Nc1ccc(Oc2ncnc3cc(OCCCN4CCOCC4)c4c(c23)OCCO4)cc1Cl]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(2-chloro-4-hydroxyphenyl)-3-(2-fluoro-5-(trifluoromethyl) phenyl)urea, with a yield of 45%; $^1$H NMR (DMSO-$d_6$, 300 MHz) δ ppm 1.96-1.20 (2H, m), 2.35-2.42 (6H, m), 3.59 (4H, br), 4.19-2.45 (2H, m), 4.43 (4H, d, J=15.0 Hz), 7.05 (1H, s), 7.23 (1H, d, J=9.1 Hz), 7.43-7.53 (3H, m), 8.18 (1H, d, J=8.7 Hz), 8.46 (1H, s), 8.64-8.66 (1H, m), 9.03 (1H, s), 9.72 (1H, s); MS: 678[M+H]$^+$.

Example 72. Preparation of 1-(4-chloro-3-(trifluoromethyl)phenyl)-3-(4-((5-(2-morpholinoethoxy)-2,3-dihydro-[1,4]dioxino[2,3-f]quinazolin-10-yl)oxy)phenyl)urea

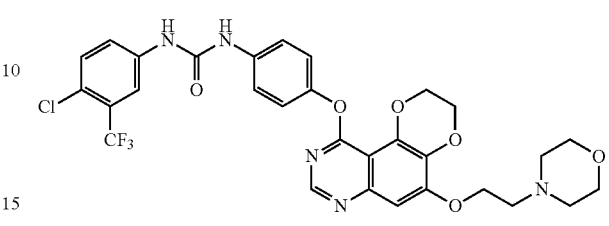

According to the same operation in Example 18, the target product as a white solid was obtained from the reaction of 10-chloro-5-(2-morpholinoethoxy)-2,3-dihydro-[1,4]dioxino[2,3-f]quinazoline and 1-(4-chloro-3-(trifluoromethyl)phenyl)-3-(4-hydroxyphenyl) urea, with a yield of 55%; $^1$H NMR (DMSO-$d_6$, 300 MHz) δ 3.43 (4H, br), 3.72 (4H, br), 4.23-4.57 (8H, m), 6.96 (3H, br), 7.37 (2H, br), 7.62 (2H, br), 8.11 (1H, s), 8.40 (1H, s), 8.76 (1H, s), 9.18 (1H, s); MS: 646[M+H]$^+$.

Example 73. Preparation of 1-(2-fluoro-5-(trifluoromethyl)phenyl)-3-(4-((5-(3-morpholinoethoxy)-2,3-dihydro-[1,4]dioxino[2,3-f]quinazolin-10-yl)oxy)phenyl)urea According to the same operation in Example 18, the target product as a white solid was obtained from the reaction of 10-chloro-5-(2-morpholinoethoxy)-2,3-dihydro-[1,4]dioxino[2,3-f]quinazoline and 1-(2-fluoro-5-(trifluoromethyl)phenyl)-3-(4-hydroxyphenyl) urea, with a yield of 54%; 1H NMR (DMSO-$d_6$, 300 MHz) δ 3.43 (4H, s), 3.73 (4H, s), 4.10-4.71 (8H, m), 6.96 (3H, br), 7.21-7.63 (4H, m), 8.40 (1H, s), 8.62 (1H, d, J=7.1 Hz), 8.85 (1H, s), 9.05 (1H, s); MS: 630[M+H]$^+$.

Example 74. Preparation of 1-(3-chloro-4-fluorophenyl)-3-(4-((5-(3-morpholinopropoxy)-2,3-dihydro-[1,4]dioxino[2,3-f]quinazolin-10-yl)oxy)phenyl)urea

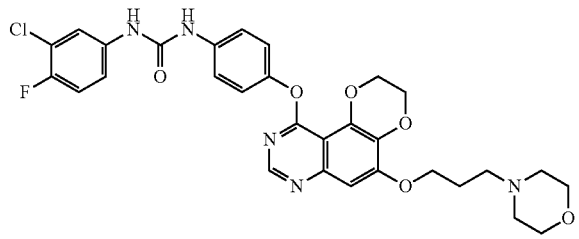 [SMILES: O=C(Nc1ccc(Oc2ncnc3cc(OCCCN4CCOCC4)c4c(c23)OCCO4)cc1)Nc1ccc(F)c(Cl)c1]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(3-chloro-4-fluorophenyl)-3-(4-hydroxyphenyl)urea, with a yield of 45%; 1H NMR (DMSO-$d_6$, 300 MHz) δ 1.89-2.05 (2H, m), 2.31-2.46 (6H, m), 3.59 (4H, s), 4.16-4.28 (2H, m), 4.32-4.55 (4H, m), 7.03 (1H, s), 7.14 (2H, d, J=8.4 Hz), 7.34 (2H, d, J=7.4 Hz), 7.51 (2H, d, J=8.5 Hz), 7.82 (1H, d, J=7.1 Hz), 8.41 (1H, d, J=2.8 Hz), 8.87-9.03 (2H, m); MS: 610[M+H]$^+$.

Example 75. Preparation of 1-(4-fluoro-3-(trifluoromethyl)phenyl)-3-(4-((5-(3-morpholinopropoxy)-2,3-dihydro-[1,4]dioxino[2,3-f]quinazolin-10-yl)oxy)phenyl)urea

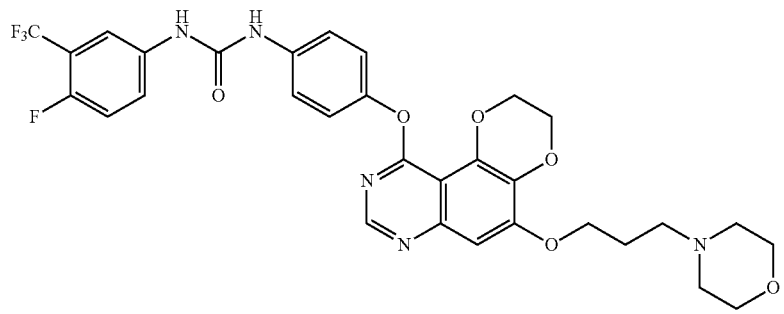 [SMILES: O=C(Nc1ccc(Oc2ncnc3cc(OCCCN4CCOCC4)c4c(c23)OCCO4)cc1)Nc1ccc(F)c(C(F)(F)F)c1]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(4-fluoro-3-(trifluoromethyl)phenyl)-3-(4-hydroxyphenyl) urea, with a yield of 41%; $^1$H NMR (DMSO-$d_6$, 300 MHz) δ 2.01 (2H, s), 3.24-3.55 (6H, m), 3.63 (4H, s), 4.23 (2H, s), 4.37-4.51 (4H, m), 7.04 (1H, s), 7.14 (2H, d, J=8.3 Hz), 7.45 (1H, s), 7.50-7.60 (2H, m), 7.67 (1H, s), 8.03 (1H, s), 8.42 (1H, s), 9.06 (1H, s), 9.24 (1H, s); MS: 644[M+H]$^+$.

Example 76. Preparation of 1-(2-fluoro-5-(trifluoromethyl)phenyl)-3-(4-((5-(2-(tetrahydro pyrrol-1-yl)ethoxy)-2,3-dihydro-[1,4]dioxino[2,3-f]quinazolin-10-yl)oxy)phenyl)urea

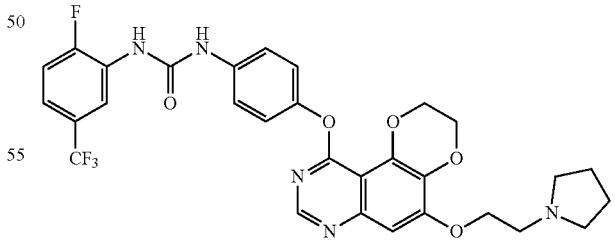

According to the same operation in Example 18, the target product as a white solid was obtained from the reaction of 10-chloro-5-(2-(tetrahydropyrrol-1-yl)ethoxy)-2,3-dihydro-[1,4]dioxino[2,3-f]quinazoline and 1-(2-fluoro-5-(trifluoromethyl)phenyl)-3-(4-hydroxyphenyl)urea, with a yield of 64%; $^1$H NMR (DMSO-$d_6$, 300 MHz) δ 1.81 (4H, s), 3.59 (4H, s), 4.16-4.56 (8H, m), 6.83 (1H, s), 6.97 (2H, d, J=8.3 Hz), 7.39 (4H, s), 8.19 (2H, s), 8.85 (1H, s), 9.05 (1H, s); MS: 614[M+H]$^+$.

Example 77. Preparation of 1-(4-((5-ethoxy-2,3-dihydro-[1,4]dioxino[2,3-f]quinazolin-10-yl)oxy)phenyl)-3-(2-fluoro-5-(trifluoromethyl)phenyl)urea

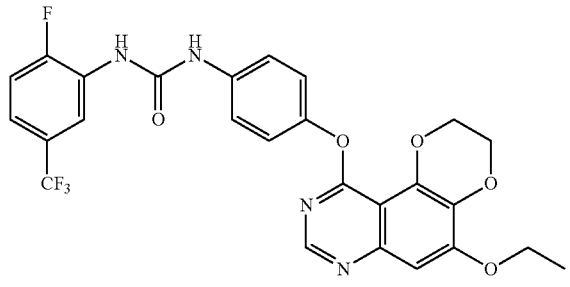 [SMILES: CCOc1cc2ncnc(Oc3ccc(NC(=O)Nc4cc(C(F)(F)F)ccc4F)cc3)c2c2c1OCCO2]

According to the same operation in Example 18, the target product as a white solid was obtained from the reaction of 10-chloro-5-ethoxy-2,3-dihydro-[1,4]dioxino[2,3-f]quinazoline and 1-(2-fluoro-5-(trifluoromethyl)phenyl)-3-(4-hydroxyphenyl)urea, with a yield of 55%; 1H NMR (DMSO-$d_6$, 300 MHz) δ 1.42 (3H, t, J=6.9 Hz), 4.18-4.27 (2H, m), 4.36-4.42 (2H, m), 4.42-4.49 (2H, m), 7.02 (1H, s), 7.17 (2H, d, J=8.4 Hz), 7.40 (1H, s), 7.49-7.58 (3H, m), 8.42 (1H, d, J=2.9 Hz), 8.59-8.68 (1H, m), 8.98 (1H, s), 9.35 (1H, s); MS: 545[M+H]$^+$.

Example 78. Preparation of 1-(4-((5-isopropoxy-2,3-dihydro-[1,4]dioxino[2,3-f]quinazolin-10-yl)oxy)phenyl)-3-(2-fluoro-5-(trifluoromethyl)phenyl)urea

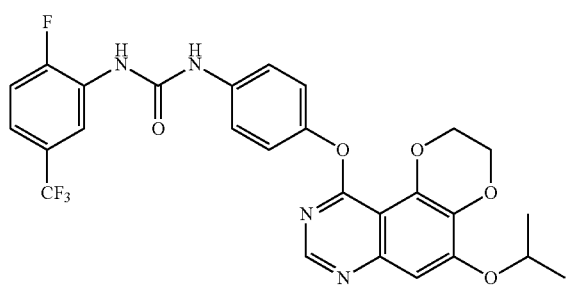 [SMILES: CC(C)Oc1cc2ncnc(Oc3ccc(NC(=O)Nc4cc(C(F)(F)F)ccc4F)cc3)c2c2c1OCCO2]

According to the same operation in Example 18, the target product as a white solid was obtained from the reaction of 10-chloro-5-isopropoxy-2,3-dihydro-[1,4]dioxino[2,3-f]quinazoline and 1-(2-fluoro-5-(trifluoromethyl)phenyl)-3-(4-hydroxyphenyl)urea, with a yield of 55%; 1H NMR (DMSO-$d_6$, 300 MHz) δ 1.37 (6H, d, J=5.8 Hz), 4.41 (4H, d, J=15.9 Hz), 4.83-4.98 (1H, m), 7.04 (1H, s), 7.16 (2H, d, J=8.4 Hz), 7.41 (1H, s), 7.49-7.57 (3H, m), 8.41 (1H, s), 8.64 (1H, d, J=7.1 Hz), 8.93 (1H, s), 9.27 (1H, s); MS: 559[M+H]$^+$.

Example 79. Preparation of 1-(2-fluoro-5-(trifluoromethyl)phenyl)-3-(4-((5-((tetrahydro-2H-pyran-4-yl)oxy)-2,3-dihydro-[1,4]dioxino[2,3-f]quinazolin-10-yl)oxy)phenyl)urea

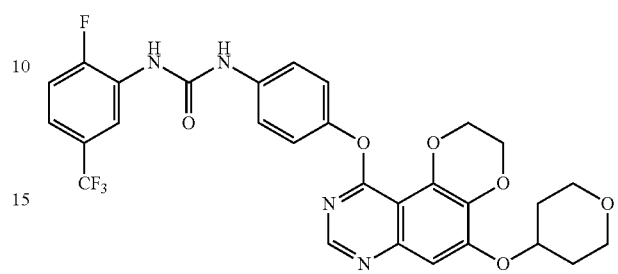

According to the same operation in Example 18, the target product as a white solid was obtained from the reaction of 10-chloro-5-((tetrahydro-2H-pyran-4-yl)oxy)-2,3-dihydro-[1,4]dioxino[2,3-f]quinazoline and 1-(2-fluoro-5-(trifluoromethyl)phenyl)-3-(4-hydroxyphenyl)urea, with a yield of 51%; 1H NMR (DMSO-$d_6$, 300 MHz) δ 2.22-2.49 (4H, m), 3.77-4.00 (4H, m), 4.42 (4H, d, J=15.8 Hz), 5.27 (1H, s), 7.01 (1H, s), 7.17 (2H, d, J=8.4 Hz), 7.40 (1H, s), 7.48-7.58 (3H, m), 8.42 (1H, d, J=2.9 Hz), 8.64 (1H, d, J=7.2 Hz), 8.93 (1H, s), 9.27 (1H, s); MS: 601[M+H]$^+$ Example 80. Preparation of 1-(2-fluoro-5-(trifluoromethyl)phenyl)-3-(4-((5-((tetrahydrofuran-3-yl)oxy)-2,3-dihydro-[1,4]dioxino[2,3-f]quinazolin-10-yl)oxy)phenyl)urea

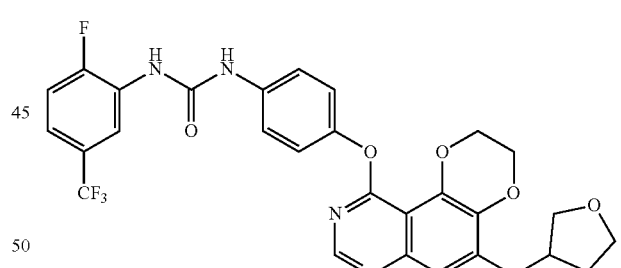

According to the same operation in Example 18, the target product as a white solid was obtained from the reaction of 10-chloro-5-((tetrahydrofuran-3-yl)oxy)-2,3-dihydro-[1,4]dioxino[2,3-f]quinazoline and 1-(2-fluoro-5-(trifluoromethyl)phenyl)-3-(4-hydroxy phenyl)urea, with a yield of 53%; 1H NMR (DMSO-$d_6$, 300 MHz) δ 1.91-2.03 (2H, m), 2.60-2.69 (2H, m), 2.73 (1H, br), 4.16-4.28 (2H, m), 4.42 (4H, d, J=15.5 Hz), 7.06 (1H, s), 7.17 (2H, d, J=8.4 Hz), 7.40 (1H, s), 7.47-7.59 (3H, m), 8.42 (1H, s), 8.59-8.68 (1H, m), 8.93 (1H, s), 9.27 (1H, s); MS: 587[M+H]$^+$.

Example 81. Preparation of 1-(4-((5-(3-(1,1-dioxidothiomorpholino)propoxy)-2,3-dihydro-[1,4]dioxino[2,3-f]quinazolin-10-yl)oxy)phenyl)-3-(2-fluoro-5-(trifluoromethyl)phenyl)urea

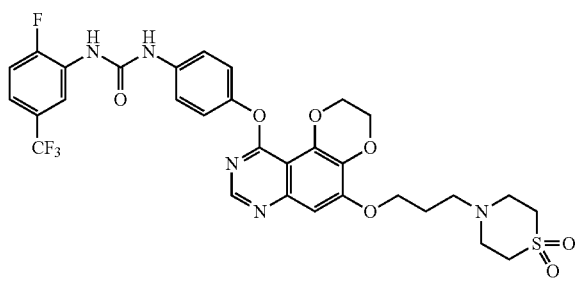 [SMILES: O=C(Nc1ccc(Oc2ncnc3cc(OCCCN4CCS(=O)(=O)CC4)c4c(c23)OCCO4)cc1)Nc1cc(C(F)(F)F)ccc1F]

According to the same operation in Example 18, the target product as a white solid was obtained from the reaction of 10-chloro-5-(3-(1,1-dioxidothiomorpholino)propoxy)-2,3-dihydro-[1,4]dioxino[2,3-f]quinazoline and 1-(2-fluoro-5-(trifluoromethyl)phenyl)-3-(4-hydroxyphenyl)urea, with a yield of 53%; 1H NMR (DMSO-d$_6$, 300 MHz) δ 1.58-1.75 (2H, m), 2.00-2.14 (2H, m), 3.33-3.38 (6H, m), 3.55 (2H, t, J=10.7 Hz), 3.83-3.95 (2H, m), 4.43 (4H, d, J=14.6 Hz), 7.10-7.23 (3H, m), 7.41 (1H, s), 7.46-7.59 (3H, m), 8.41 (1H, d, J=2.9 Hz), 8.64 (1H, d, J=7.2 Hz), 8.93 (1H, s), 9.27 (1H, s); MS: 692[M+H]$^+$ Example 82. 1-(2-chloro-4-((5-(3-(dimethylamino)propoxy)-2,3-dihydro-[1,4]dioxino[2,3-f]quinazolin-10-yl)amino)phenyl)-3-cyclopropylurea

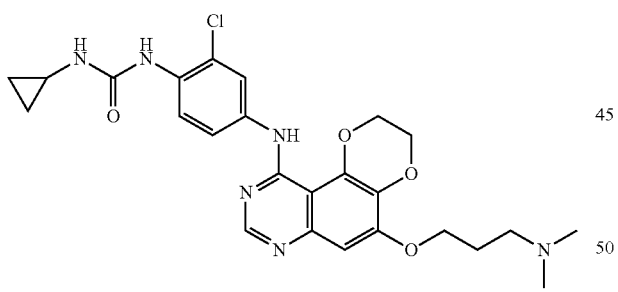

According to the same procedure in Example 1, a pale yellow solid was obtained from 10-chloro-5-(3-(dimethylamino)propoxy)-2,3-dihyd-[1,4]dioxino[2,3-f]quinazoline and 1-(4-amino-2-chlorophenyl)-3-cyclopropylurea, with a yield of 51%;

$^1$H NMR (400 MHz, DMSO-d$_6$) δ ppm: 0.45-0.39 (2H, m), 0.61-0.70 (2H, m), 1.97-2.01 (4H, m), 2.34 (6H, s), 2.53-2.56 (1H, m), 4.17 (2H, t, J=6.3 Hz), 4.37-4.44 (2H, m), 4.56-4.61 (2H, m), 6.87 (1H, s), 7.13 (1H, d, J=2.9 Hz), 7.59 (1H, d, J=9.0 Hz), 7.88 (1H, s), 8.05-8.15 (2H, m), 8.40 (1H, s), 9.55 (1H, s); MS: 513[M+H]$^+$.

Example 83. 1-(2-chloro-4-((5-(2-(1-methylpiperazin-4-yl)ethoxy)-2,3-dihydro-[1,4]dioxino[2,3-f]quinazolin-10-yl)amino)phenyl)-3-cyclopropylurea

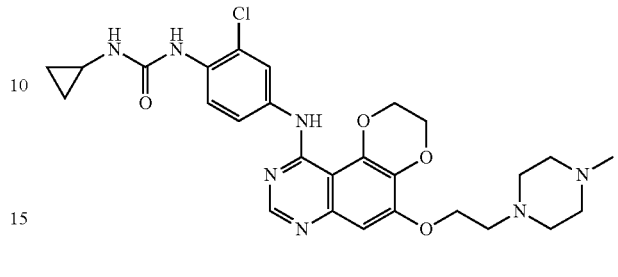

According to the same procedure in Example 1, a pale yellow solid was obtained from 10-chloro-5-(2-(1-methylpiperazin-4-yl)ethoxy)-2,3-dihydro-[1,4]dioxino[2,3-f]quinazoline and 1-(4-amino-2-chlorophenyl)-3-cyclopropylurea, with a yield of 56%; $^1$H NMR (400 MHz, DMSO-d$_6$) δ ppm: 0.42 (2H, d, J=7.1 Hz), 0.65 (2H, d, J=7.1 Hz), 2.15 (3H, s), 2.25-2.40 (8H, m), 2.53-2.58 (1H, m), 2.74 (2H, d, J=5.8 Hz), 4.22 (2H, t, J=5.8 Hz), 4.36-4.43 (2H, m), 4.55-4.62 (2H, m), 6.90 (1H, s), 7.16 (1H, d, J=2.9 Hz), 7.59 (1H, d, J=9.1 Hz), 7.89 (1H, s), 8.04-8.15 (2H, m), 8.40 (1H, s), 9.55 (1H, s); MS: 554[M+H]$^+$.

Example 84. Preparation of 1-(2-chloro-4-((5-(2-methylthioethoxy)-2,3-dihydro-[1,4]dioxino[2,3-f]quinazolin-10-yl)amino)phenyl)-3-cyclopropylurea

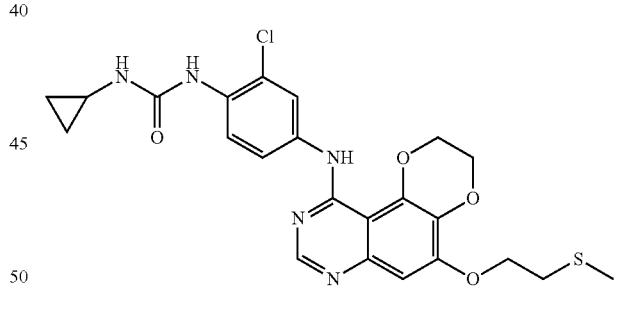

According to the same operation in Example 18, a pale yellow solid was obtained from 10-chloro-5-(2-methylthioethoxy)-2,3-dihydro-[1,4]dioxino[2,3-f]quinazoline and 1-(4-amino-2-chlorophenyl)-3-cyclopropylurea, with a yield of 71%; 1H NMR (400 MHz, DMSO-d$_6$) δ ppm: 0.38-0.46 (2H, m), 0.63-0.68 (2H, m), 2.20 (3H, s), 2.54-2.57 (1H, m), 2.91 (2H, t, J=6.5 Hz), 4.30 (2H, t, J=6.5 Hz), 4.39-4.41 (2H, br), 4.58-4.60 (2H, br), 6.90 (1H, s), 7.12 (1H, d, J=2.9 Hz), 7.59 (1H, d, J=9.0 Hz), 7.87 (1H, s), 8.08 (1H, d, J=9.0 Hz), 8.13 (1H, s), 8.41 (1H, s), 9.55 (1H, s); MS: 502[M+H]$^+$.

Example 85. Preparation of 1-(2-chloro-4-(((5-(2-methylthio)ethoxy)-2,3-dihydro-[1,4]dioxino[2,3-f]quinazolin-10-yl)oxy)phenyl)-3-cyclopropylurea

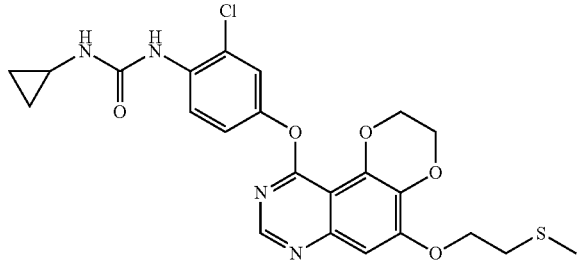 [SMILES: CSCCOc1cc2ncnc(Oc3ccc(NC(=O)NC4CC4)c(Cl)c3)c2c2c1OCCO2]

According to the same operation in Example 18, a pale yellow solid was obtained from 10-chloro-5-((2-methylthio)ethoxy)-2,3-dihydro-[1,4]dioxino[2,3-f]quinazoline and 1-(2-chloro-4-hydroxyphenyl)-3-cyclopropylurea, with a yield of 77%; 1H NMR (400 MHz, DMSO-$d_6$) δ ppm: 0.38-0.40 (2H, m), 0.61-0.63 (2H, m), 2.05 (3H, s), 2.52-2.57 (1H, m), 2.69-2.74 (2H, m), 4.30-4.47 (6H, m), 6.78-6.79 (1H, m), 6.85-6.86 (1H, m), 7.22 (1H, s), 7.59 (1H, s), 7.69-7.73 (2H, m), 8.75 (1H, s); MS: 503[M+H]$^+$.

Example 86. Preparation of 1-(2-chloro-4-(((5-(3-methoxy)propoxy)-2,3-dihydro-[1,4]dioxino[2,3-f]quinazolin-10-yl)oxy)phenyl)-3-cyclopropylurea

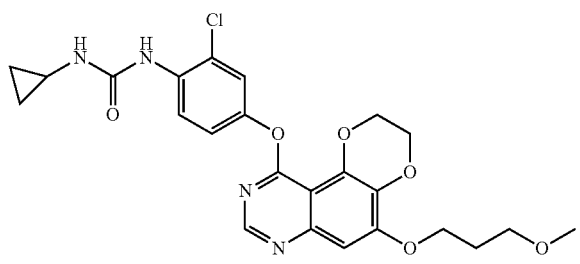 [SMILES: COCCCOc1cc2ncnc(Oc3ccc(NC(=O)NC4CC4)c(Cl)c3)c2c2c1OCCO2]

According to the same operation in Example 18, a pale yellow solid was obtained from 10-chloro-5-((3-methoxy)propoxy)-2,3-dihydro-[1,4]dioxino[2,3-f]quinazoline and 1-(2-chloro-4-hydroxyphenyl)-3-cyclopropylurea, with a yield of 74%;

$^1$H NMR (400 MHz, DMSO-$d_6$) δ ppm: 0.36-0.49 (2H, m), 0.67 (2H, d, J=7.0 Hz), 2.01-2.07 (2H, m), 2.53-2.56 (1H, m), 3.38 (3H, s), 3.51 (2H, t, J=6.2 Hz), 4.22 (2H, t, J=6.4 Hz), 4.43 (4H, d, J=18.0 Hz), 7.03 (1H, s), 7.13-7.16 (2H, m), 7.40 (1H, d, J=2.7 Hz), 7.94 (1H, d, J=9.0 Hz), 8.17 (1H, d, J=9.0 Hz), 8.44 (1H, s); MS: 501[M+H]$^+$.

Example 87. Preparation of 1-(2-chloro-4-((5-(2-dimethylamino)ethoxy)-2,3-dihydro-[1,4]dioxino[2,3-f]quinazolin-10-yl)amino)phenyl)-3-cyclopropylurea

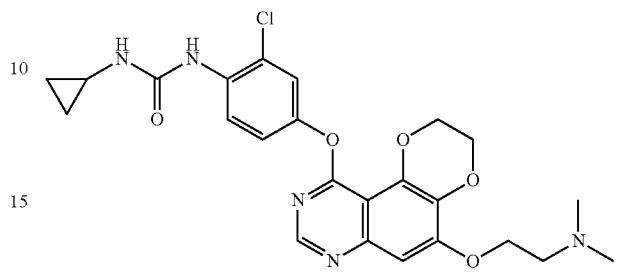

According to the same procedure in Example 1, a pale yellow solid was obtained from 10-chloro-5-((2-dimethylamino)ethoxy)-2,3-dihydro-[1,4]dioxino[2,3-f]quinazoline and 1-(2-chloro-4-aminophenyl)-3-cyclopropylurea, with a yield of 66%;

$^1$H NMR (400 MHz, DMSO-$d_6$) δ ppm 0.39-0.46 (2H, m), 0.66 (2H, d, J=6.9 Hz), 2.25 (6H, br), 2.53-2.56 (1H, m), 2.70 (2H, t, J=5.7 Hz), 4.20 (2H, br), 4.40 (2H, br), 4.60 (2H, br), 6.91 (1H, d, J=6.4 Hz), 7.11 (1H, d, J=2.9 Hz), 7.49 (1H, d, J=8.8 Hz), 7.60-7.64 (1H, m), 7.88-7.91 (1H, m), 8.03-8.17 (1H, m), 8.42 (1H, d, J=8.8 Hz), 9.59 (1H, s); MS: 499[M+H]$^+$.

Example 88. Preparation of 1-(2-chloro-4-((5-(6-methoxy)hexyloxy)-2,3-dihydro-[1,4]dioxino[2,3-f]quinazolin-10-yl)oxy)phenyl)-3-cyclopropylurea

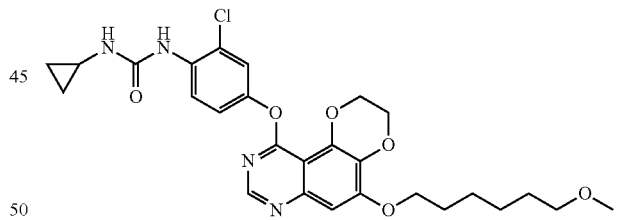

According to the same operation in Example 18, a pale yellow solid was obtained from 10-chloro-5-((6-methoxyhexyl)oxy)-2,3-dihydro-[1,4]dioxino[2,3-f]quinazoline and 1-(2-chloro-4-hydroxyphenyl)-3-cyclopropylurea, with a yield of 70%;

$^1$H NMR (300 MHz, DMSO-$d_6$) δ 0.43 (2H, s), 0.66 (2H, s), 1.41 (4H, s), 1.52 (2H, s), 1.79 (2H, t, J=7.2 Hz), 2.57 (1H, d, J=6.6 Hz), 3.22 (3H, d, J=2.7 Hz), 3.30-3.33 (2H, m), 4.14 (2H, d, J=6.6 Hz), 4.41 (4H, d, J=13.5 Hz), 7.02 (1H, s), 7.15 (2H, d, J=9.4 Hz), 7.40 (1H, d, J=2.9 Hz), 7.94 (1H, s), 8.17 (1H, d, J=9.0 Hz), 8.43 (1H, d, J=2.7 Hz); MS: 543 [M+H]$^+$.

Example 89. Preparation of 1-(2-fluoro-5-chlorophenyl)-3-(4-((5-(3-morpholinopropoxy)-2,3-dihydro-[1,4]dioxino[2,3-f]quinazolin-10-yl)oxy)phenyl)urea

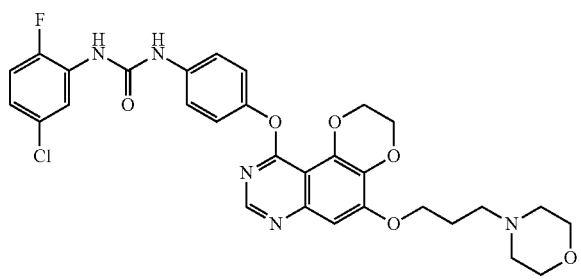 [SMILES: O=C(Nc1ccc(Oc2ncnc3cc(OCCCN4CCOCC4)c4c(c23)OCCO4)cc1)Nc1cc(Cl)ccc1F]

According to the same operation in Example 18, the target product as a white solid was obtained from the reaction of 10-chloro-5-(3-morpholinopropoxy)-2,3-dihydro-[1,4]dioxino[2,3-f]quinazoline and 1-(5-chloro-2-fluorophenyl)-3-(4-hydroxyphenyl)urea, with a yield of 41%; 1H NMR (DMSO-d$_6$, 300 MHz) δ 1.88-2.03 (2H, m), 2.34-2.46 (6H, m), 3.59 (4H, s), 4.14-4.27 (2H, m), 4.34-4.51 (4H, m), 6.98-7.10 (2H, m), 7.16 (2H, d, J=8.3 Hz), 7.26-7.38 (1H, m), 7.52 (2H, d, J=8.4 Hz), 8.29 (1H, d, J=4.2 Hz), 8.42 (1H, s), 8.79 (1H, s), 9.23 (1H, s); MS: 610[M+H]$^+$.

Example 90: Preparation of 1-(4-chloro-3-(trifluoromethyl)phenyl)-3-(4-((5-methoxy-2,3-dihydro-[1,4]dioxino[2,3-f]quinolin-10-yl)oxy)phenyl)urea

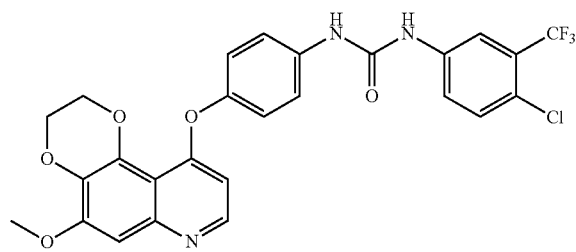 [SMILES: COc1cc2nccc(Oc3ccc(NC(=O)Nc4ccc(Cl)c(C(F)(F)F)c4)cc3)c2c2c1OCCO2]

Step 1) Preparation of 1-(8-methoxy-6-nitro-2,3-dihydrobenzo[b][1,4]dioxin-5-yl)ethan-1-one

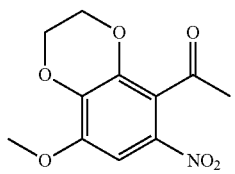

1-(8-methoxy-2,3-dihydrobenzo[b][1,4]dioxin-5-yl)ethan-1-one (20.8 g, 100 mmol), nitric acid (22 mL) and acetic acid (44 mL) were added in a round bottom flask and stirred until the reaction was completed. The mixture was poured onto crushed ice, and filtered to give 16.5 g product as a yellow solid, with a yield of 66%. H NMR (400 MHz, Chloroform-d) δ 7.37 (s, 1H), 4.43 (dd, J=5.4, 2.7 Hz, 2H), 4.35 (dd, J=5.3, 2.7 Hz, 2H), 3.98 (s, 3H), 2.57 (s, 3H); MS: 254[M+H]$^+$.

Step 2) Preparation of 1-(8-methoxy-6-amino-2,3-dihydrobenzo[b][1,4]dioxin-5-yl)ethan-1-one

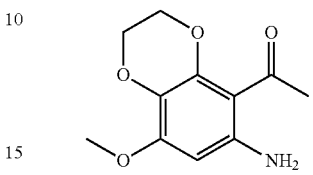

1-(8-methoxy-6-nitro-2,3-dihydrobenzo[b][1,4]dioxin-5-yl)ethan-1-one (16.5 g, 65 mmol) was added in a reaction flask, and palladium on carbon (2 g) was added thereto with stirring under hydrogen atmosphere until the reaction was completed. The mixture was suction filtered and concentrated to give 13.7 g product as an off-white solid, with a yield of 95%. 1H NMR (400 MHz, DMSO-d6) δ 6.90 (s, 2H), 5.96 (s, 1H), 4.32-4.25 (m, 2H), 4.18-4.09 (m, 2H), 3.72 (s, 3H), 2.41 (s, 3H); MS: 224[M+H]$^+$.

Step 3) Preparation of 10-hydroxy-5-methoxy-2,3-dihydro-[1,4]dioxino[2,3-f]quinoline

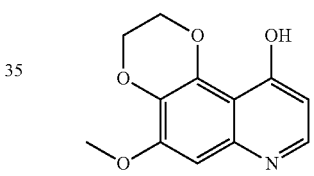

1-(6-amino-8-methoxy-2,3-dihydrobenzo[b][1,4]dioxin-5-yl)ethan-1-one (13.7 g, 62 mmol) and ethyl formate (27.5 g, 372 mmol) were dissolved in dioxane. Sodium tert-butoxide (17.8 g, 186 mmol) was added, and the mixture was stirred until the starting material disappeared. 10 ml of methanol was added and stirring was continued until the reaction was completed, and the reaction solution was neutralized with hydrochloric acid, the mixture was suction filtered and concentrated to give 14.4 g product as an off-white solid, with a yield of 99%. $^1$H NMR (400 MHz, DMSO-d6) δ 11.26 (s, 1H), 7.59 (d, J=7.3 Hz, 1H), 6.55 (s, 1H), 5.77 (d, J=7.2 Hz, 1H), 4.34-4.13 (m, 4H), 3.82 (s, 3H); MS: 234[M+H]$^+$.

Step 4) Preparation of 10-chloro-5-methoxy-2,3-dihydro-[1,4]dioxino[2,3-f]quinoline

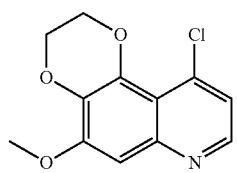 [SMILES: COc1cc2nccc(Cl)c2c2c1OCCO2]

10-hydroxy-5-methoxy-2,3-dihydro-[1,4]dioxino[2,3-f]quinoline (14.4 g, 61 mmol) was added in a reaction flask and toluene was added to solve it. After that, triethylamine (42 mL, 305 mmol) and phosphorus oxychloride (17 mL, 183 mmol) were added and the mixture was stirred until the reaction was completed. The solvent was evaporated, and the obtained solid was washed with aqueous sodium bicarbonate and filtered to give 14.1 g of an off-white solid, with a yield of 92%. $^1$H NMR (400 MHz, DMSO-$d_6$) δ 8.51 (d, J=4.9 Hz, 1H), 7.38 (d, J=4.8 Hz, 1H), 7.12 (s, 1H), 4.49-4.29 (m, 4H), 3.93 (s, 3H); MS: 252[M+H]$^+$.

Step 5) Preparation of 5-methoxy-10-(4-nitrophenoxy)-2,3-dihydro-[1,4]dioxino[2,3-f]quinoline

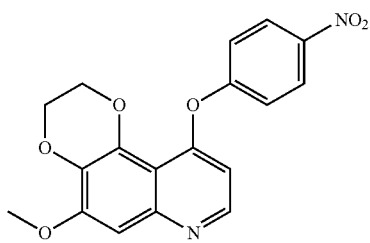 [SMILES: COc1cc2nccc(Oc3ccc([N+](=O)[O-])cc3)c2c2c1OCCO2]

10-chloro-5-methoxy-2,3-dihydro-[1,4]dioxino[2,3-f]quinoline (251 mg, 1 mmol) and p-nitrophenol (139 mg, 1 mmol) were added in a reaction flask, chlorobenzene was added, and the mixture was heated to reflux while stirring until the reaction was completed. After cooling, the mixture was suction filtered, and the resulting solid was washed with aqueous potassium carbonate to give 250 mg of a pale yellow solid, with a yield of 71%. MS: 355[M+H]$^+$.

Step 6) Preparation of 4-((5-methoxy-2,3-dihydro-[1,4]dioxino[2,3-f]quinolin-10-yl)oxy)aniline

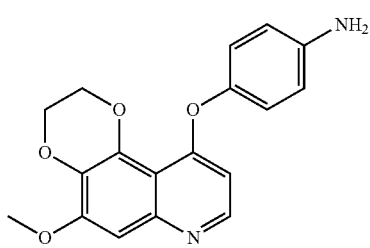

5-methoxy-10-(4-nitrophenoxy)-2,3-dihydro-[1,4]dioxino[2,3-f]quinoline (250 mg, 0.7 mmol) was added in a reaction flask, and methanol and Raney nickel (250 mg) were added, and the mixture was stirred under a hydrogen atmosphere until the reaction was completed. The mixture was suction filtered and concentrated to give 226 mg of an off-white solid product, with a yield of 99%. MS: 325[M+H]$^+$.

Step 7) Preparation of 1-(4-chloro-3-(trifluoromethyl)phenyl)-3-(4-((5-methoxy-2,3-dihydro-[1,4]dioxino[2,3-f]quinoline-10-yl)oxy)phenyl)urea

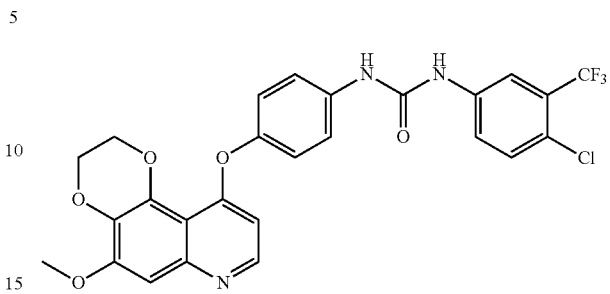

4-((5-methoxy-2,3-dihydro-[1,4]dioxino[2,3-f]quinoline-10-yl)oxy)aniline (226 mg, 0.7 mmol) and 4-chloro-3-(trifluoromethyl)aniline (195 mg, 1 mmol) were dissolved in dichloromethane. Triethylamine (0.4 mL, 3 mmol) and triphosgene (296 mg, 1 mmol) were added thereto. The mixture was stirred until the reaction was completed. The mixture was added with aqueous sodium carbonate and extracted with ethyl acetate. The organic phase was concentrated and subjected to column chromatography to give 306 mg of a white solid, with a yield of 80%. HNMR (400 MHz, DMSO-$d_6$) δ 9.22 (s, 1H), 8.97 (s, 1H), 8.42 (d, J=5.2 Hz, 1H), 8.12 (d, J=2.4 Hz, 1H), 7.73-7.59 (m, 2H), 7.59-7.49 (m, 2H), 7.15-6.98 (m, 3H), 6.44 (d, J=5.2 Hz, 1H), 4.34 (s, 4H), 3.93 (s, 3H); MS: 546[M+H]$^+$.

Example 91 Preparation of 1-(4-chloro-3-(trifluoromethyl)phenyl)-3-(3-fluoro-4-((5-methoxy-2,3-dihydro-[1,4]dioxino[2,3-f]quinoline-10-yl)oxy)phenyl)urea

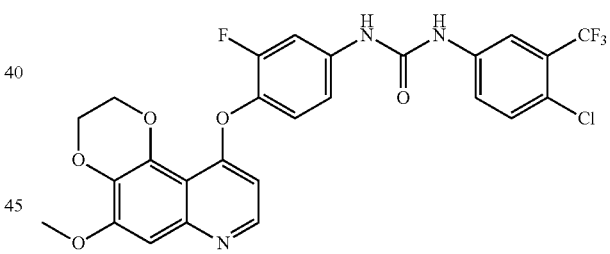

Steps 1 to 4 are the same as steps 1 to 4 in the Preparation of Example 90.

Step 5) Preparation of 10-(2-fluoro-4-nitrophenoxy)-5-methoxy-2,3-dihydro-[1,4]dioxino[2,3-f]quinoline

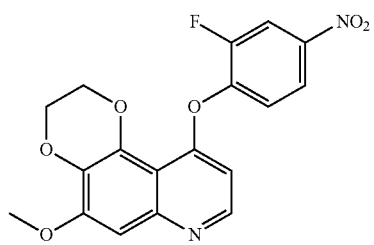 [SMILES: COc1cc2nccc(Oc3ccc([N+](=O)[O-])cc3F)c2c2c1OCCO2]

Referring to Example 90, synthetic step 5, it was prepared with exactly the same operations, using the same molar equivalent of 2-fluoro-4-nitrophenol to replace p-nitrophenol. $^1$H NMR (400 MHz, DMSO-$d_6$) δ 8.67 (d, J=5.0 Hz, 1H), 8.44-8.27 (m, 1H), 8.13-7.93 (m, 1H), 7.19 (s, 1H), 7.07 (d, J=4.9 Hz, 1H), 6.98 (t, J=8.7 Hz, 1H), 4.31-4.18 (m, 2H), 4.16-4.06 (m, 2H), 3.95 (s, 3H); MS: 373[M+H]$^+$.

Step 6) Preparation of 3-fluoro-4-((5-methoxy-2,3-dihydro-[1,4]dioxino[2,3-f]quinoline-10-yl)oxy) aniline

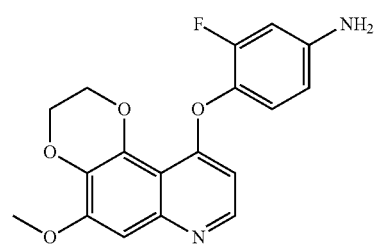

Referring to Example 90, synthetic step 6, it was prepared with exactly the same operates, using the same molar equivalent of 10-(2-fluoro-4-nitrophenoxy)-5-methoxy-2,3-dihydro-[1,4]dioxino[2,3-f]quinoline to replace 5-methoxy-10-(4-nitrophenoxy)-2,3-dihydro-[1,4]dioxino[2,3-f]quinoline. $^1$H NMR (400 Hz, DMSO-d6) δ 8.38 (d, J=5.2 Hz, 1H), 7.05 (s, 1H), 6.99 (t, J=9.0 Hz, 1H), 6.61-6.49 (m, 1H), 6.49-6.38 (m, 1H), 6.33 (d, J=5.3 Hz, 1H), 5.53-5.37 (m, 2H), 4.36-4.38 (m, 4H), 3.92 (s, 3H); MS: 343[M+H]$^+$.

Step 7) Preparation of 1-(4-chloro-3-(trifluoromethyl)phenyl)-3-(3-fluoro-4-((5-methoxy-2,3-dihydro-[1,4]dioxino[2,3-f]quinoline-10-yl)oxy)phenyl)urea

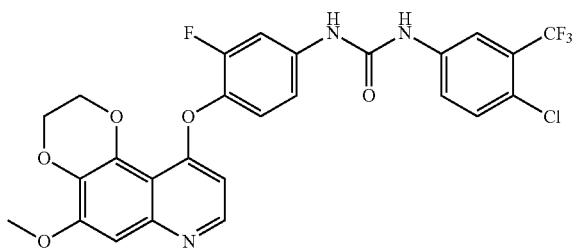 [SMILES: COc1cc2nccc(Oc3ccc(NC(=O)Nc4ccc(Cl)c(C(F)(F)F)c4)cc3F)c2c2c1OCCO2]

Referring to Example 90, synthetic step 7, it was prepared with exactly the same operates, using the same molar equivalent of 3-fluoro-4-((5-methoxy-2,3-dihydro-[1,4]dioxino[2,3-f]quinoline-10-yl)oxy)aniline to replace 4-((5-methoxy-2,3-dihydro-[1,4]dioxino[2,3-f]quinoline-10-yl)oxy)aniline. $^1$HNMR (400 MHz, DMSO-$d_6$) δ 9.32 (s, 1H), 9.22 (s, 1H), 8.48 (d, J=5.3 Hz, 1H), 8.16 (d, J=2.5 Hz, 1H), 7.82-7.61 (m, 3H), 7.37-7.24 (m, 2H), 7.13 (s, 1H), 6.47 (d, J=5.3 Hz, 1H), 4.41 (s, 4H), 3.98 (s, 3H); $^{13}$CNMR (101 MHz, DMSO-$d_6$) δ 161.1, 152.8, 152.5, 152.4, 149.6, 146.6, 139.5, 138.2, 138.2, 136.0, 132.4, 132.3, 123.8, 123.7, 123.0, 117.4, 115.7, 107.9, 107.7, 103.9, 101.5, 64.5, 63.9, 56.2, 49.0; MS: 564[M+H]$^+$.

Example 92 Preparation of 1-(4-chloro-3-(trifluoromethyl)phenyl)-3-(2-fluoro-4-((5-methoxy-2,3-dihydro-[1,4]dioxino[2,3-f]quinoline-10-yl)oxy) phenyl)urea

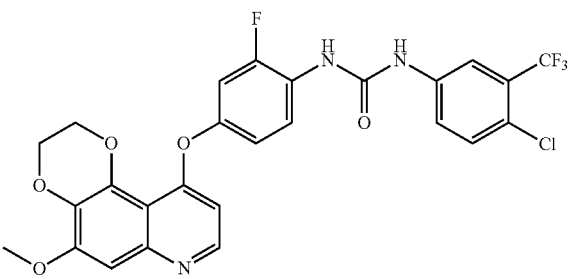 [SMILES: COc1cc2nccc(Oc3ccc(NC(=O)Nc4ccc(Cl)c(C(F)(F)F)c4)c(F)c3)c2c2c1OCCO2]

Step 1 to Step 4 are identical to Step 1 to Step 4 in the Preparation of Example 90.

Step 5) Preparation of 10-(3-fluoro-4-nitrophenoxy)-5-methoxy-2,3-dihydro-[1,4]dioxino[2,3-f] quinoline

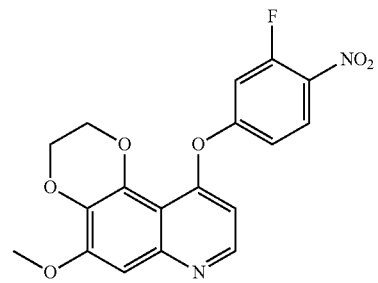 [SMILES: COc1cc2nccc(Oc3ccc([N+](=O)[O-])c(F)c3)c2c2c1OCCO2]

Referring to Example 90, synthetic step 5, it was prepared with exactly the same operates, using the same molar equivalent of 3-fluoro-4-nitrophenol to replace p-nitrophenol. MS: 373[M+H]$^+$.

Step 6) Preparation of 2-fluoro-4-((5-methoxy-2,3-dihydro-[1,4]dioxino[2,3-f]quinoline-10-yl)oxy) aniline

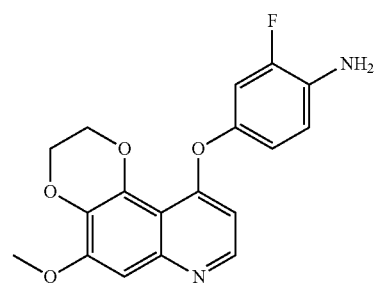 [SMILES: COc1cc2nccc(Oc3ccc(N)c(F)c3)c2c2c1OCCO2]

Referring to Example 90, synthetic step 6, it was prepared with exactly the same operates, using the same molar equivalent of 10-(3-fluoro-4-nitrophenoxy)-5-methoxy-2,3-dihydro-[1,4]dioxino[2,3-f]quinoline to replace 5-methoxy-10-(4-nitrophenoxy)-2,3-dihydro-[1,4]dioxino[2,3-f]quinoline. ¹HNMR (400 MHz, DMSO-d6) δ 8.38 (d, J=5.2 Hz, 1H), 7.04 (s, 1H), 6.98-6.91 (m, 1H), 6.89-6.79 (m, 1H), 6.78-6.67 (m, 1H), 6.37 (d, J=5.2 Hz, 1H), 5.14 (s, 2H), 4.43-4.30 (m, 4H), 3.91 (s, 3H); MS: 343[M+H]⁺.

Step 7) Preparation of 1-(4-chloro-3-(trifluoromethyl)phenyl)-3-(2-fluoro-4-((5-methoxy-2,3-dihydro-[1,4]dioxino[2,3-f]quinoline-10-yl)oxy)phenyl)urea

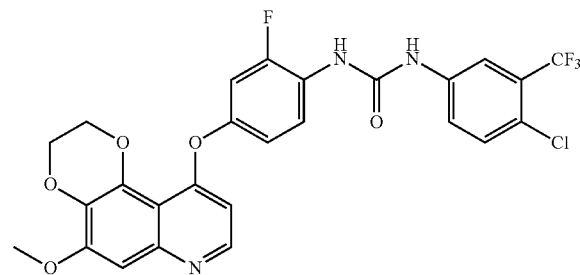 [SMILES: COc1cc2nccc(Oc3ccc(NC(=O)Nc4ccc(Cl)c(C(F)(F)F)c4)c(F)c3)c2c2c1OCCO2]

Referring to Example 90, synthetic step 7, it was prepared with exactly the same operates, using the same molar equivalent of 2-fluoro-4-((5-methoxy-2,3-dihydro-[1,4]dioxino[2,3-f]quinoline-10-yl)oxy)aniline to replace 4-((5-methoxy-2,3-dihydro-[1,4]dioxino[2,3-f]quinoline-10-yl)oxy)aniline. ¹HNMR (400 MHz, DMSO-d6) δ 9.48 (s, 1H), 8.66 (d, J=2.3 Hz, 1H), 8.48 (d, J=5.2 Hz, 1H), 8.20-8.00 (m, 2H), 7.62 (d, J=1.5 Hz, 2H), 7.20-7.13 (m, 1H), 7.09 (s, 1H), 6.97-6.87 (m, 1H), 6.59 (d, J=5.2 Hz, 1H), 4.52-4.18 (m, 4H), 3.93 (s, 3H); 13CNMR (101 MHz, DMSO-d₆) δ 160.4, 152.7, 152.4, 149.7, 146.8, 139.5, 138.0, 132.5, 132.3, 123.4, 123.1, 117.10, 116.1, 108.8, 108.3, 106.7, 101.6, 64.4, 63.9, 56.2, 40.2; MS: 564[M+H]⁺.

Example 93 Preparation of 1-(4-chloro-3-(trifluoromethyl)phenyl)-3-(4-((5-(2-methoxyethoxy)-2,3-dihydro-[1,4]dioxino[2,3-f]quinoline-10-yl)oxy)phenyl)urea

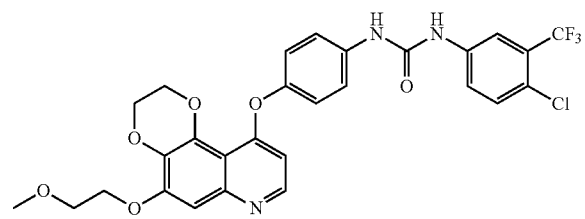 [SMILES: COCCOc1cc2nccc(Oc3ccc(NC(=O)Nc4ccc(Cl)c(C(F)(F)F)c4)cc3)c2c2c1OCCO2]

Steps 1 to 4 are the same with steps 1 to 4 in the Preparation of Example 90.

Step 4a) Preparation of 5-hydroxy-10-chloro-2,3-dihydro-[1,4]dioxino[2,3-f]quinoline

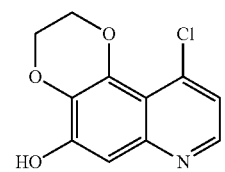 [SMILES: Oc1cc2nccc(Cl)c2c2c1OCCO2]

10-chloro-5-methoxy-2,3-dihydro-[1,4]dioxino[2,3-f]quinoline (251 mg, 1 mmol) was dissolved in dichloromethane. IM solution of boron tribromide in dichloromethane (3 mL, 3 mmol) was added dropwise. The mixture was stirred until the reaction was completed, which was concentrated to give 236 mg product as a pale yellow, with a yield of 99%. MS: 238[M+H]⁺.

Step 4b) Preparation of 10-chloro-5-(2-methoxyethoxy)-2,3-dihydro-[1,4]dioxino[2,3-f]quinoline

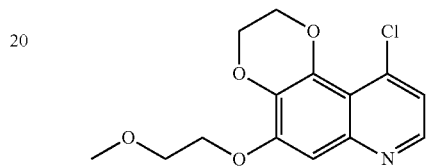

5-hydroxy-10-chloro-2,3-dihydro-[1,4]dioxino[2,3-f]quinoline (236 mg, 1 mmol) was dissolved in N,N-dimethylformamide, and 1-bromo-2-methoxyethane (138 mg, 1 mmol) and potassium carbonate (414 mg, 3 mmol) were added. The mixture was heated and stirred until the reaction was completed. Water was added and the mixture was extracted with ethyl acetate. The organic phase was concentrated and subjected to column chromatography to give 236 mg of an off-white solid, with a yield of 80%. 1H NMR (400 MHz, DMSO-d6) δ 8.70-8.46 (m, 1H), 7.50-7.33 (m, 1H), 7.25-7.09 (m, 1H), 4.40 (s, 4H), 4.30-4.23 (m, 2H), 3.77-3.71 (m, 2H), 3.33-3.32 (m, 3H); MS: 296[M+H]⁺.

Step 5) Preparation of 5-(2-methoxyethoxy)-10-(4-nitrophenoxy)-2,3-dihydro-[1,4]dioxino[2,3-f]quinoline

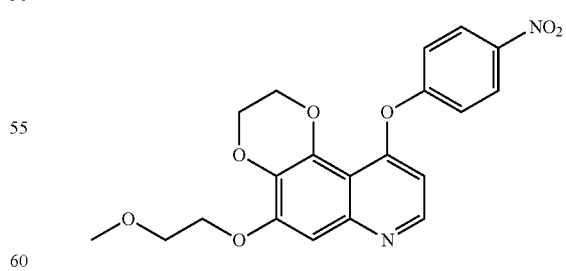

Referring to Example 90, synthetic step 5, it was prepared with exactly the same operates, using the same molar equivalent of 10-chloro-5-(2-methoxyethoxy)-2,3-dihydro-[1,4]dioxino[2,3-f]quinoline to replace 10-chloro-5-methoxy-2,3-dihydro-[1,4]dioxino[2,3-f]quinoline. MS: 399[M+H]⁺.

Step 6) Preparation of 4-((5-(2-methoxyethoxy)-2,3-dihydro-[1,4]dioxino[2,3-f]quinoline-10-yl)oxy)aniline

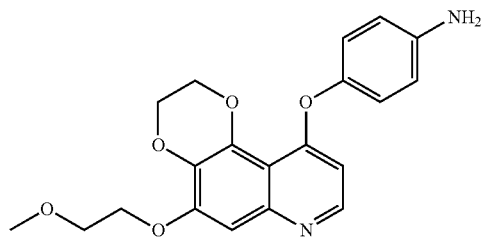 [SMILES: COCCOc1cc2nccc(Oc3ccc([N+](=O)[O-])cc3)c2c2c1OCCO2]

Referring to Example 90, synthetic step 6, it was prepared with exactly the same operates, using the same molar equivalent of 5-(2-methoxyethoxy)-10-(4-nitrophenoxy)-2,3-dihydro-[1,4]dioxino[2,3-f]quinoline to replace 5-methoxy-10-(4-nitrophenoxy)-2,3-dihydro-[1,4]dioxino[2,3-f]quinoline. MS: 369[M+H]$^+$.

Step 7) Preparation of 1-(4-chloro-3-(trifluoromethyl)phenyl)-3-(4-((5-(2-methoxyethoxy)-2,3-dihydro-[1,4]dioxino[2,3-f]quinoline-10-yl)oxy)phenyl)urea

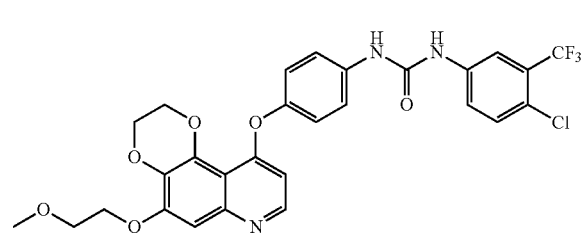 [SMILES: COCCOc1cc2nccc(Oc3ccc(NC(=O)Nc4ccc(Cl)c(C(F)(F)F)c4)cc3)c2c2c1OCCO2]

Referring to Example 90, synthetic step 7, it was prepared with exactly the same operates, using the same molar equivalent of 4-((5-(2-methoxyethoxy)-2,3-dihydro-[1,4]dioxino[2,3-f]quinoline-10-yl)oxy)aniline to replace 4-((5-methoxy-2,3-dihydro-[1,4]dioxino[2,3-f]quinoline-10-yl)oxy)aniline. 1H NMR (400 MHz, DMSO-d6) δ 9.15 (s, 1H), 8.91 (s, 1H), 8.34 (d, J=5.2 Hz, 1H), 8.05 (d, J=2.4 Hz, 1H), 7.63-7.53 (m, 2H), 7.50-7.39 (m, 2H), 7.11-6.90 (m, 3H), 6.36 (d, J=5.2 Hz, 1H), 4.37-4.21 (m, 4H), 4.21-4.13 (m, 2H), 3.70-3.63 (m, 2H), 3.28 (s, 3H); MS: 590[M+H]$^+$.

Example 94 Preparation of 1-(4-chloro-3-(trifluoromethyl)phenyl)-3-(3-fluoro-4-((5-(2-methoxyethoxy)-2,3-dihydro-[1,4]dioxino[2,3-f]quinoline-10-yl)oxy)phenyl)urea

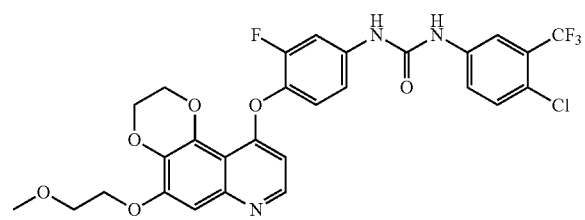 [SMILES: COCCOc1cc2nccc(Oc3ccc(NC(=O)Nc4ccc(Cl)c(C(F)(F)F)c4)cc3F)c2c2c1OCCO2]

Steps 1 to 4b are the same with steps 1 to 4b in the Preparation of Example 93.

Step 5) Preparation of 10-(2-fluoro-4-nitrophenoxy)-5-(2-methoxyethoxy)-2,3-dihydro-[1,4]dioxino[2,3-f]quinoline

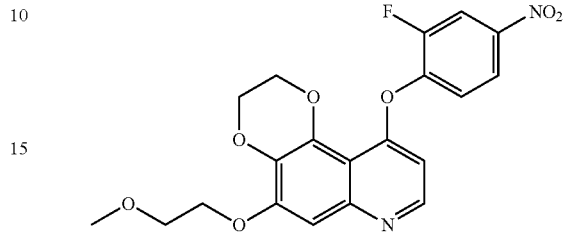

Referring to Example 93, synthetic step 5, it was prepared with exactly the same operates, using the same molar equivalent of 2-fluoro-4-nitrophenol to replace p-nitrophenol. MS: 417[M+H]$^+$.

Step 6) Preparation of 3-fluoro-4-((5-(2-methoxyethoxy)-2,3-dihydro-[1,4]dioxino[2,3-f]quinoline-10-yl)oxy)aniline

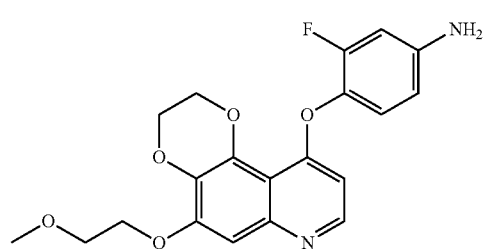 [SMILES: COCCOc1cc2nccc(Oc3ccc([N+](=O)[O-])cc3F)c2c2c1OCCO2]

Referring to Example 90, synthetic step 6, it was prepared with exactly the same operates, using the same molar equivalent of 10-(2-fluoro-4-nitrophenoxy)-5-(2-methoxyethoxy)-2,3-dihydro-[1,4]dioxino[2,3-f]quinoline to replace 5-methoxy-10-(4-nitrophenoxy)-2,3-dihydro-[1,4]dioxino[2,3-f]quinoline. MS: 387[M+H]$^+$.

Step 7) Preparation of 1-(4-chloro-3-(trifluoromethyl)phenyl)-3-(3-fluoro-4-((5-(2-methoxyethoxy)-2,3-dihydro-[1,4]dioxino[2,3-f]quinoline-10-yl)oxy)phenyl)urea

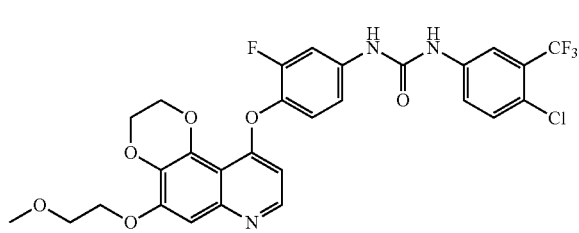 [SMILES: COCCOc1cc2nccc(Oc3ccc(NC(=O)Nc4ccc(Cl)c(C(F)(F)F)c4)cc3F)c2c2c1OCCO2]

Referring to Example 90, synthetic step 7, it was prepared with exactly the same operates, using the same molar equivalent of 3-fluoro-4-((5-(2-methoxyethoxy)-2,3-dihydro-[1,4]dioxino[2,3-f]quinoline-10-yl)oxy)aniline to replace 4-((5-methoxy-2,3-dihydro-[1,4]dioxino[2,3-f]quinoline-10-yl)oxy)aniline. 1H NMR (300 MHz, DMSO-d6) δ 9.33 (s, 1H), 9.22 (s, 1H), 8.42 (d, J=4.8 Hz, 1H), 8.11 (d, J=2.0 Hz, 1H), 7.77-7.52 (m, 3H), 7.25 (d, J=2.5 Hz, 2H), 7.12-7.04 (m, 1H), 6.47-6.35 (m, 1H), 4.47-4.32 (m, 4H), 4.30-4.19 (m, 2H), 3.80-3.69 (m, 2H), 3.35 (s, 3H); MS: 608[M+H]$^+$.

Example 95. Preparation of 1-(2-fluoro-5-(trifluoromethyl)phenyl)-3-(4-((5-(3-morpholinopropoxy)-2,3-dihydro-[1,4]dioxino[2,3-f]quinazolin-10-yl)oxy)phenyl)urea L-malate

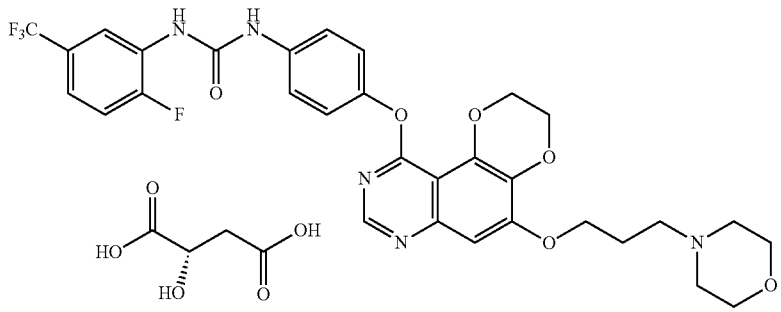 [SMILES: O=C(Nc1ccc(Oc2ncnc3cc(OCCCN4CCOCC4)c4c(c23)OCCO4)cc1)Nc1cc(C(F)(F)F)ccc1F ; O=C(O)C[C@H](O)C(=O)O]

The compound obtained in Example 65 (645 mg, 1 mmol) was dissolved in 15 mL acetone and stirred at room temperature for 15 min, then 2 mL of aqueous solution of L-malic acid (134 mg, 1 mmol) was added, and stirring was continued for 12 hours. The reaction mixture was filtered to give a white solid (400 mg). The solid was dissolved in 15 mL of ethanol and heated under reflux. After completely dissolved, the solution was cooled and allowed to stand, which was filtered to obtain 260 mg of a white crystalline compound, HPLC >99%. 1H NMR (DMSO-d$_6$, 300 MHz) δ 2.03-2.37 (4H, m), 3.24-3.75 (6H, m), 3.61-4.22 (5H, m), 4.23-4.35 (2H, m), 4.37-4.51 (4H, m), 7.07 (1H, s), 7.16 (2H, d, J=8.2 Hz), 7.40 (1H, s), 7.45-7.62 (3H, m), 8.44 (1H, s), 8.63 (1H, d, J=7.1 Hz), 9.08 (1H, s), 9.59 (1H, s); MS: 644[M+H]$^+$.

Biological Example 1. Test of Small Molecule Compounds for Inhibiting the Activity of VEGFR-2 Kinase The test was carried out as follows:
1. Dilution of the compound: a total of 12 concentrations were obtained using a 4-fold gradient dilution from the highest concentration of 10000 nM (the maximum final concentration of the drug used in this experiment is 10000 nM, and the minimum final concentration is 0.002384 nM),
2. 2.5 µl of the gradient-diluted compounds was taken with a transfer pipette to a 384-well plate,
3. Addition of enzyme: 5 µl of 2×VEGFR-2 kinase was taken with a transfer pipette to the corresponding reaction well of the 384-well plate, which was mixed and pre-reacted at room temperature for 30 min,
4. 2.5 µl of 4× substrate/ATP Mix was taken with a transfer pipette to the corresponding reaction well of the 384-well plate,
5. Negative control: 2.5 µl/well 4× substrate/ATP Mix and 7.5 µl 1× Kinase Assay Buffer were added to the wells of the 384-well plate, Positive control: 2.5 µl/well 4× substrate/ATP Mix, 2.5 µl/well 1× Kinase Assay Buffer containing 4% DMSO, and 5 µl/well 2×VEGFR-2 solution were added to the 384-well plate. The final concentration of DMSO in the reaction system is 4%,
6. The mixture was mixed well and then centrifuged and reacted at room temperature in dark for 60 min,
7. Termination of the enzymatic reaction: 5 µl of 4× Stop solution was taken with a transfer pipette to the wells of the 384-well plate, mixed and then centrifuged, and reacted at room temperature for 5 min,
8. Development of the reaction: 5 µl of 4× Detection Mix was taken with a transfer pipette to the wells of the 384-well plate for color development, and the mixture was mixed and then centrifuged and reacted at room temperature for 60 min,
9. The 384-well plate was placed into the Envision plate reader and the signal was detected using the appropriate program,
10. Analysis and processing of the raw data:

The drug concentrations and the corresponding inhibition rates were input into GraphPad Prism5 for calculation, and the inhibition rate of the compound was calculated as follows: inhibition rate (%)=[1−(experimental well reading value−negative control well reading value)/(positive control well reading value−negative control well reading value)]× 100%. Processing with GraphPad Prism5 software yielded the corresponding IC$_{50}$ value (the concentration of the compound at which 50% of the highest inhibition of the enzyme is achieved).

Table (1) lists the determination results of the inhibitory activity of some of the compounds of the present disclosure on the tyrosine kinase, and uses A, B, C, and D to represent the ranges of IC$_{50}$, wherein A indicates that the IC$_{50}$ is less than or equal to 50 nM, B indicates that the IC$_{50}$ is greater than 50 nM but less than or equal to 500 nM, C indicates that the IC$_{50}$ is greater than 500 nM but less than or equal to 5000 nM, and D indicates that the IC$_{50}$ is greater than 5000 nM.

TABLE (1)

determination results of the inhibitory activity of some of the compounds of the present disclosure on the tyrosine kinase

| Example No. | VEGFR-2 IC$_{50}$ |
|---|---|
| 1 | B |
| 2 | A |
| 3 | B |
| 4 | A |
| 5 | D |
| 6 | B |

TABLE (1)-continued determination results of the inhibitory activity of some of the compounds of the present disclosure on the tyrosine kinase

| Example No. | VEGFR-2 IC$_{50}$ |
|---|---|
| 7 | A |
| 8 | B |
| 9 | B |
| 10 | A |
| 11 | A |
| 12 | A |
| 13 | D |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | B |
| 29 | C |
| 30 | A |
| 31 | A |
| 32 | A |
| 33 | A |
| 34 | A |
| 35 | A |
| 36 | D |
| 37 | A |
| 38 | A |
| 39 | A |
| 40 | B |
| 41 | A |
| 42 | A |
| 43 | A |
| 44 | D |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | B |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | C |
| 73 | C |
| 74 | A |
| 75 | A |
| 76 | D |
| 77 | A |
| 78 | A |
| 79 | A |
| 80 | A |
| 81 | A |
| 82 | A |
| 83 | B |
| 84 | A |
| 85 | C |
| 86 | A |
| 87 | B |
| 88 | A |
| 89 | A |
| 90 | A |
| 91 | B |
| 92 | B |
| 93 | B |
| 94 | B |

Biological Example 2. Test of Small Molecule Compounds for Inhibiting the Activity of C-RAF and B-RAF Kinases The test was carried out as follows:

1. Preparation of test compounds: according to the molecular weight of the compounds, an appropriate volume of DMSO was directly added to dissolve the test compounds. For storing the compound, the concentration of DMSO is 100%, and the final concentration of DMSO in the experimental system is 1%. The compounds were 3-fold serially diluted with DMSO to obtain a total of 8 dilutions, with a maximum concentration of 1000 nM and a minimum concentration of 0.46 nM.

2. Preparation of the sorafenib positive control: sorafenib, a selective inhibitor of BRAF and RAF1, was used as the positive control of this experiment, and the dilution method thereof was the same as that of the above test compounds.

3. Test Conditions:
   Enzyme: B-RAF: 0.1 ng/l (the final concentration in the reaction system); C-RAF: 0.1 ng/μl (the final concentration in the reaction system)
   Substrate and ATP: inactive MEKI: 2 ng/μl (the final concentration in the reaction system); ATP: 35 μM (the final concentration in the reaction system)
   HPE: the reaction without enzyme (1% DMSO)
   ZPE: the reaction with enzyme but without compound (1% DMSO)

4. Test procedure:
   a) 1 ul of 10-fold diluted compound or 10% DMSO was added to a 384-well assay plate,
   b) 4 ul enzyme solution or assay buffer was added to the wells of the assay plate,
   c) the plate was centrifuged at 1000 rpm for 1 minute to homogeneous,
   d) 5 ul of ATP-substrate mixture was added to the wells of the assay plate,
   e) the plate was shaked for mixing for 2 minutes,
   f) the plate was incubated at 30° C. for 1 hour,
   g) 10 ul of ADP-Glo reagent was added to the wells of the assay plate, and the plate was incubated for 40 minutes at 27° C.,
   h) 20 ul of kinase assay solution was added to the wells of the plate, and the plate was incubated for 30 minutes at 27° C.,
   i) the chemiluminescent signal was read with Envision.

5. Analysis of the results: calculation of the compound inhibition rate:

Inhibition rate (%)=(control measurement without compound–sample measurement)/(control measurement without compound–control measurement without enzyme)*100%

The $IC_{50}$ values of the positive control compound and the test compounds were calculated using the Prism software according to the variable slope of the curve.

Table (2) lists the determination results of the inhibitory activities of some of the compounds in the present disclosure on tyrosine kinases, C-RAF and B-RAF. The ranges of $IC_{50}$ are represented by A, B, C and D, where A indicates that the $IC_{50}$ is less than or equal to 200 nM, B indicates that the $IC_{50}$ is greater than 200 nM but less than or equal to 500 nM, C indicates that the $IC_{50}$ is greater than 500 nM but less than or equal to 1000 nM, and D indicates that the $IC_{50}$ is greater than 1000 nM.

TABLE (2)

determination results of the inhibitory activities of some of the compounds in the present disclosure on tyrosine kinases, C-RAF and B-RAF

| Example No. | C-RAF $IC_{50}$ | B-RAF $IC_{50}$ |
|---|---|---|
| 11 | C | B |
| 17 | D | D |
| 18 | B | B |
| 19 | A | A |
| 20 | B | B |
| 42 | C | A |
| 45 | D | D |
| 46 | C | C |
| 47 | B | B |
| 48 | B | A |
| 49 | D | D |
| 50 | D | D |
| 62 | D | D |
| 64 | D | D |
| 65 | B | B |
| 66 | B | B |
| 67 | C | B |
| 68 | C | B |
| Sorafenib | $IC_{50}$ = 47.0 nM | $IC_{50}$ = 41.0 nM |

Biological Example 3. Cell Survival Assay for Small Molecule Compounds

The specific procedure was carried out as follows:

1. 600 μL of trypsin was added to a T75 cell culture flask, it was digested in a 37° C. incubator for about 1 min, then 5 mL of DMEM complete medium was added, which was blowed evenly, transferred to a 15 mL centrifuge tube, and centrifuged at 1000 rpm for 4 min;

2. The supernatant was discarded, 5 mL of DMEM complete medium was added, which was blowed evenly, and then mixed with 10 μL of cell suspension and 10 μL of 0.4% trypan blue, and reading was recorded using a cell counter;

3. Cells of 6 different cell lines (MHCC97H, HuH7, HepG2, A549, 8505C) were seeded in 96-well plates at a cell density of 6000 cells/80 μL of complete medium/well, and cultured overnight. Only sterile water was added in the outer 36 wells of the 96-well plates, and the remaining inside 60 wells were used for cell experiments and controls;

4. Dilution of compounds: a total of 10 concentrations of the compounds were obtained using a 3-fold dilution from the starting concentration of 10 mM.

5. 20 μL of different compounds in different concentrations were added to each corresponding well, and the remaining wells were added with 20 μL of complete medium, the plate was shaked, and the concentration of DMSO in each well is 0.25%.

6. After incubation for 72 h, 10 μL of CCK-8 reagent was added to each well, and cultured at 37° C. for 1-2 h; the OD value was read at 450 nm.

7. Cell Viability (%)=[(As−Ab)/(Ac−Ab)]*100%
   As: Experimental well (medium containing cells, CCK-8, compound)
   Ac: Control well (medium containing cells, CCK-8)
   Ab: Blank well (medium without cell and compound, CCK-8)

8. Values were input into Graphpad Prism 5 software to calculate $IC_{50}$ (the concentration of the compound at which 50% of the maximum survival rate is achieved).

Table (3) lists the determination results of the activity of representative compounds of the present disclosure against various cancer cells, wherein MHCC97H, HuH7, and HepG2 are liver cancer cell lines, A549 is a lung cancer cell line, and 8505C is a thyroid cancer cell line.

TABLE (3)

determination results of cell activity of representative compounds of the present disclosure

| Example No. | MHCC97H $IC_{50}$ (nM) | HuH7 $IC_{50}$ (nM) | HepG2 $IC_{50}$ (nM) | A549 $IC_{50}$ (nM) | 8505C $IC_{50}$ (nM) |
|---|---|---|---|---|---|
| 18 | >2500 | 1330.0 | 1743.0 | 1038.0 | 23.2 |
| 20 | 1719.0 | 856.0 | 301.7 | 1121.0 | 20.29 |
| 46 | >2500 | 1260.0 | 2365.0 | 428.3 | 8.57 |
| 47 | 714.0 | 585.0 | 123.1 | 194.2 | 5.35 |
| 48 | 1229.0 | 1269.0 | 925.6 | 590.0 | 21.9 |

The biological data provided by the present disclosure indicates that the compounds of the present disclosure are useful for treating or preventing diseases caused by abnormalities of tyrosine kinases such as VEGFR-2 and/or C-RAF and/or B-RAF. Some of the compounds of the present disclosure exhibit strong in vitro inhibitory activities against cancer cells, including liver cancer cells MHCC97, HuH7, HepG2, lung cancer cell A549, and thyroid cancer cell 8505C. Thus, the compounds of the disclosure are useful in the treatment of cancer, including primary and metastatic cancers, including solid tumors. Such cancers include, but are not limited to, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal interstitialoma, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, cholangiocarcinoma. The compounds of the disclosure also treat cancers that are resistant to one or more other therapeutic methods.

The compounds of the present disclosure are also useful in diseases associated with tyrosine kinases other than cancer, including, but not limited to, ocular fundus diseases, psoriasis, rheumatoid arthritis, atheroma, pulmonary fibrosis, and liver fibrosis. The compounds of the present disclosure may be administered as a monotherapy or a combination therapy, i.e., in combination with a plurality of compounds of the present disclosure or in combination with other drugs other than the present disclosure.

The above is a preferred embodiment of the present disclosure, and it should be noted that those skilled in the art can make various improvements and modifications to the embodiments of the present disclosure without departing from the principles of the present disclosure. These improvements and modifications are also considered to be within the scope of the disclosure.

The invention claimed is:

1. A compound of Formula (I), or a pharmaceutically acceptable salt, enantiomer, stereoisomer, hydrate, or solvate thereof:

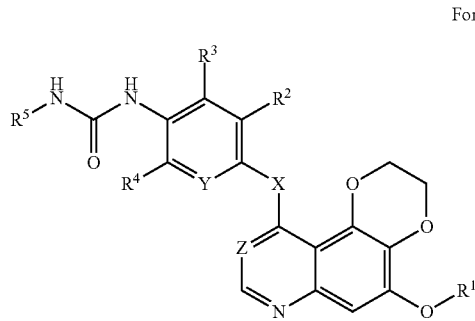

Formula (I)

in the Formula (I),

X is O or NH;
Y is N or CH;
Z is N;
$R^1$ is H, a $C_1$-$C_9$ alkyl, a $C_3$-$C_7$ cycloalkyl, a 4-7 membered heterocyclyl, a $C_1$-$C_6$ alkyl substituted by $C_3$-$C_7$ cycloalkyl, a $C_1$-$C_6$ alkyl substituted by 4-7 membered heterocyclyl, or a substituted $C_1$-$C_9$ alkyl, and the substituents in the substituted $C_1$-$C_9$ alkyl are one or more of the following groups consist of hydroxyl, $C_1$-$C_6$ alkoxyl, $C_1$-$C_6$ alkylthio group, amino group substituted by one or two $C_1$-$C_6$ alkyl, and unsubstituted amino group,
the said 4-7 membered heterocyclyl is a 4-7 membered heterocyclyl containing 1-2 atoms selected from N, O, and S, and the 4-7 membered heterocyclyl is unsubstituted or substituted by $C_1$-$C_6$ alkyl, $C_1$-$C_3$ acyl, or is oxidized by one or two oxygen atoms;
$R^2$ is H or halogen;
$R^3$ is H or halogen;
$R^4$ is H or halogen;
$R^5$ is H, $C_1$-$C_9$ alkyl, $C_3$-$C_8$ cycloalkyl, $C_1$-$C_6$ alkyl substituted by $C_3$-$C_8$ cycloalkyl, or substituted or unsubstituted aryl or heteroaryl, and the substituents of the substituted aryl or heteroaryl are one or more of the following groups consist of $C_1$-$C_3$ alkyl, $C_1$-$C_3$ alkoxyl, $C_1$-$C_3$ alkylthio group, amino group substituted by one or two $C_1$-$C_3$ alkyl or unsubstituted amino group, halogen, trifluoromethyl, aryloxy, or methylsulfonyl; and
the heteroaryl is a monocyclic or bicyclic group having 5 to 10 ring atoms, and containing 1-3 atoms selected from N, O, and S in the ring.

2. The compound, or the pharmaceutically acceptable salt, enantiomer, stereoisomer, hydrate, or solvate thereof according to claim 1, wherein $R^1$ is H, $C_1$-$C_6$ alkyl, $C_3$-$C_6$ cycloalkyl, 5-6 membered heterocyclyl, $C_1$-$C_3$ alkyl substituted by $C_3$-$C_6$ cycloalkyl, $C_1$-$C_3$ alkyl substituted by 5-6 membered heterocyclyl, or substituted $C_1$-$C_6$ alkyl, and the substituents in the substituted $C_1$-$C_6$ alkyl are one or more of the following groups consist of hydroxyl, $C_1$-$C_3$ alkoxyl, $C_1$-$C_3$ alkylthio group, amino group substituted by one or two $C_1$-$C_3$ alkyl, and unsubstituted amino group,
the said 5-6 membered heterocyclyl is a 5-6 membered heterocyclyl having 1-2 atoms selected from N, O, and S, and the 5-6 membered heterocyclyl is unsubstituted or substituted by $C_1$-$C_3$ alkyl, $C_1$-$C_3$ acyl, or is oxidized by one or two oxygen atoms.

3. The compound, or the pharmaceutically acceptable salt, enantiomer, stereoisomer, hydrate, or solvate thereof according to claim 2,
wherein $R^1$ is selected from the groups consisting of: H, methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholinyl)-4-ethyl, (1,1-dioxothiomorpholinyl)-4-propyl, methylthioethyl, methylthiopropyl, dimethylaminoethyl, dimethylaminopropyl, dimethylaminobutyl, diethylaminoethyl, diethylaminopropyl, hydroxyethyl, hydroxypropyl, hydroxybutyl, hydroxypentyl, hydroxyhexyl, aminoethyl, aminopropyl, aminobutyl, 2-methyl-2-hydroxypropyl, 3-methyl-3-hydroxybutyl, (3S)-3-aminobutyl, (3R)-3-aminobutyl, (3S)-3-hydroxybutyl, or (3R)-3-hydroxybutyl.

4. The compound, or the pharmaceutically acceptable salt, enantiomer, stereoisomer, hydrate, solvate thereof according to claim 1, wherein the halogen in $R^2$, $R^3$, $R^4$ is F, Cl or Br.

5. The compound, or the pharmaceutically acceptable salt, enantiomer, stereoisomer, hydrate, or solvate thereof according to claim 1, wherein $R^5$ is H, $C_1$-$C_6$ alkyl, $C_3$-$C_6$ cycloalkyl, $C_1$-$C_3$ alkyl substituted by $C_3$-$C_6$ cycloalkyl, or substituted or unsubstituted aryl or heteroaryl, and the substituents of the substituted aryl or heteroaryl are one or more of the following groups consist of $C_1$-$C_3$ alkyl, $C_1$-$C_3$ alkoxyl, $C_1$-$C_3$ alkylthio group, amino group substituted by one or two $C_1$-$C_3$ alkyl or unsubstituted amino group, halogen, trifluoromethyl, aryloxy and methylsulfonyl;
the heteroaryl is a monocyclic or bicyclic group having 5-10 ring atoms, and containing 1-2 ring atoms selected from N, O, and S in the ring.

6. The compound, or the pharmaceutically acceptable salt, enantiomer, stereoisomer, hydrate, or solvate thereof according to claim 1, wherein $R^5$ is H, $C_1$-$C_6$ alkyl, $C_3$-$C_6$ cycloalkyl, $C_1$-$C_3$ alkyl substituted by $C_3$-$C_6$ cycloalkyl, or substituted or unsubstituted phenyl, naphthyl or heteroaryl, wherein the substituents of phenyl, naphthyl or heteroaryl are one or more of the following groups consist of methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluoro, chloro, bromo, trifluoromethyl, phenoxy, and methylsulfonyl;
the heteroaryl is selected from the groups consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

7. The compound, or the pharmaceutically acceptable salt, enantiomer, stereoisomer, hydrate, or solvate thereof according to claim 1, wherein $R^5$ is selected from the groups consisting of H, methyl, ethyl, propyl, isopropyl, isopentyl, cyclopropyl, cyclobutyl, cyclopentyl, cyclohexyl, phenyl, 2-methoxyphenyl, 3-methoxyphenyl, 4-methoxyphenyl, 2-fluorophenyl, 3-fluorophenyl, 4-fluorophenyl, 4-phenoxyphenyl, 3-(methylsulfonyl)phenyl, 4-(methylsulfonyl)phenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-trifluoromethyl-4fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-trifluoromethyl-4-chlorophenyl, 2-chloro-4-fluorophenyl, 2-chloro-5-fluorophenyl, 3-chloro-4-fluorophenyl, pyridin-2-yl, pyridin-3-yl, pyridin-4-yl, 2-methoxy-pyridin-4-yl, 3-methyl-isoxazol-5-yl, and naphthalen-1-yl.

8. A salt of the compound of Formula (I) according to claim 1, wherein the salt is an acidic/anionic salt or a basic/cationic salt; a pharmaceutically acceptable acidic/anionic salt is in the form in which the basic nitrogen is protonated by an inorganic or organic acid; representative organic or inorganic acids are selected from hydrochloric acid, hydrobromic acid, hydroiodic acid, perchloric acid, sulfuric acid, nitric acid, phosphoric acid, formic acid, acetic acid, propionic acid, glycolic acid, lactic acid, succinic acid, maleic acid, tartaric acid, malic acid, citric acid, fumaric acid, gluconic acid, benzoic acid, mandelic acid, methanesulfonic acid, isethionic acid, benzenesulfonic acid, oxalic acid, palmitic acid, 2-naphthalenesulfonic acid, p-toluenesulfonic acid, cyclohexylsulfamic acid, salicylic acid, hexonic acid, and trifluoroacetic acid, and pharmaceutically acceptable basic/cationic salts are selected from salts of aluminum, calcium, chloroprocaine, choline, diethanolamine, ethylenediamine, lithium, magnesium, potassium, sodium and zinc.

9. A method of preparing the compound, or the pharmaceutically acceptable salt, enantiomer, stereoisomer, hydrate, or solvate thereof according to claim 1, comprising the preparation of the compound of Formula (I) by reacting the compound of Formula (II) with $H_2N-R^5$, wherein, X, Y, Z, $R^1$, $R^2$, $R^3$, $R^4$, and $R^5$ are as defined in claim 1,

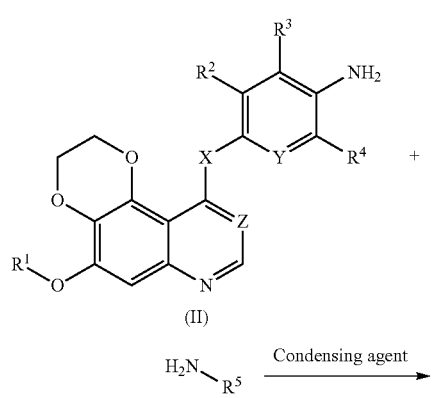

(II)

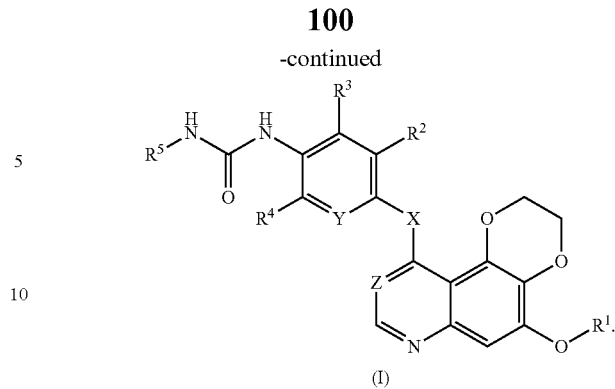

(I)

10. A method of preparing the compound, or the pharmaceutically acceptable salt, enantiomer, stereoisomer, hydrate, or solvate thereof according to claim 1, comprising the preparation of the compound of Formula (I) by reacting the compound of Formula (II') with the compound of Formula (III), wherein, X, Y, Z, $R^1$, $R^2$, $R^3$, $R^4$, and $R^5$ are as defined in claim 1,

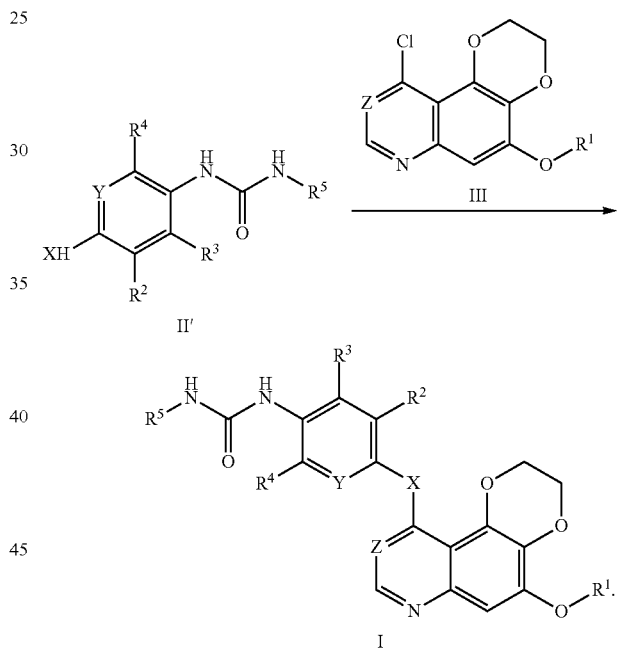

11. A compound of Formula (II),

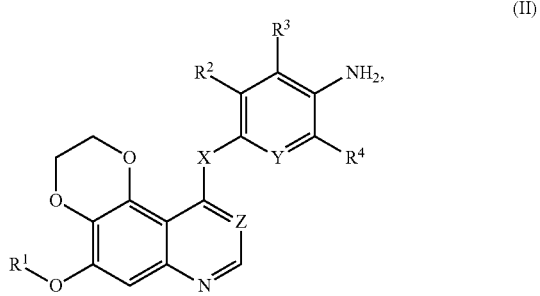

wherein,
X is O or NH,
Y is N or CH;
Z is N;
R$^1$ is H, a C$_1$-C$_9$ alkyl, a C$_3$-C$_7$ cycloalkyl, a 4-7 membered heterocyclyl, a C$_1$-C$_6$ alkyl substituted by C$_3$-C$_7$ cycloalkyl, a C$_1$-C$_6$ alkyl substituted by 4-7 membered heterocyclyl, or a substituted C$_1$-C$_9$ alkyl, and the substituents in the substituted C$_1$-C$_9$ alkyl are one or more of the following groups consist of hydroxyl, C$_1$-C$_6$ alkoxyl, C$_1$-C$_6$ alkylthio group, amino group substituted by one or two C$_1$-C$_6$ alkyl, and unsubstituted amino group,
the said 4-7 membered heterocyclyl is a 4-7 membered heterocyclyl containing 1-2 atoms selected from N, O, and S, and the 4-7 membered heterocyclyl is unsubstituted or substituted by C$_1$-C$_6$ alkyl, C$_1$-C$_3$ acyl, or is oxidized by one to two oxygen atoms;
R$^2$ is H or halogen;
R$^3$ is H or halogen; and
R$^4$ is H or halogen.

12. A pharmaceutical composition, comprising:
the compound of Formula (I), or the pharmaceutically acceptable salt, enantiomer, stereoisomer, hydrate, or solvate thereof according to claim 1, and
pharmaceutically acceptable carriers or excipients.

13. A pharmaceutical composition, comprising
the compound of Formula (I), or the pharmaceutically acceptable salt, enantiomer, stereoisomer, hydrate, or solvate thereof according to claim 1 as an active ingredient,
one or more additional therapeutic agents, and
one or more pharmaceutically acceptable carriers or excipients.

14. A method of treating a disease associated with a tyrosine kinase selected from VEGFR-2, C-RAF, or B-RAF in a subject, comprising administering to the subject a compound of Formula (I), or a pharmaceutically acceptable salt, enantiomer, stereoisomer, hydrate, or solvate thereof according to claim 1, wherein the disease is a tumor consisting of non-small cell lung, cancer, small cell lung cancer pancreatic cancer, colorectal cancer, melanoma, liver cancer, and thyroid cancer.

15. The compound, or the pharmaceutically acceptable salt, enantiomer, stereoisomer, hydrate, or solvate thereof according to claim 1, wherein
X is O or NH;
Y is N or CH;
Z is N;
R$^1$ is a C$_1$-C$_6$ alkyl, a C$_1$-C$_6$ alkyl substituted by 5-6 membered heterocyclyl, or a C$_1$-C$_6$ alkyl substituted by C$_1$-C$_6$ alkoxyl,
R$^2$ is H or halogen;
R$^3$ is H or halogen;
R$^4$ is H or halogen;
R$^5$ is substituted or unsubstituted aryl, and the substituents of the substituted aryl are one or more of the following groups consist of C$_1$-C$_3$ alkyl, halogen, or trifluoromethyl.

16. The compound, or the pharmaceutically acceptable salt, enantiomer, stereoisomer, hydrate, or solvate thereof according to claim 1, wherein the said compound is selected from the group consisting of:
1-(4-((5-methoxy-2,3-dihydro-[1,4]dioxino[2,3-f]quinazolin-10-yl)amino)phenyl)-3-cyclopropylurea,
1-(2-chloro-4-((5-methoxy-2,3-dihydro-[1,4]dioxino[2,3-f]quinazolin-10-yl)amino)phenyl)-3-cyclopropylurea,
1-(4-((5-methoxy-2,3-dihydro-[1,4]dioxino[2,3-f]quinazolin-10-yl)amino)phenyl)-3-(3-methoxyphenyl)urea,
1-(2-chloro-4-((5-methoxy-2,3-dihydro-[1,4]dioxino[2,3-f]quinazolin-10-yl)amino)phenyl)-3-(3-methoxyphenyl)urea,
1-(2-chloro-4-((5-methoxy-2,3-dihydro-[1,4]dioxino[2,3-f]quinazolin-10-yl)amino)phenyl)-3-(pyridin-2-yl)urea,
1-(2-chloro-4-((5-methoxy-2,3-dihydro-[1,4]dioxino[2,3-f]quinazolin-10-yl)amino)phenyl)-3-phenylurea,
1-(2-chloro-4-((5-methoxy-2,3-dihydro-[1,4]dioxino[2,3-f]quinazolin-10-yl)amino)phenyl)-3-(4-fluorophenyl)urea,
1-(2-chloro-4-((5-methoxy-2,3-dihydro-[1,4]dioxino[2,3-f]quinazolin-10-yl)amino)phenyl)-3-(3-methylisoxazol-5-yl)urea,
1-(2-chloro-4-((5-methoxy-2,3-dihydro-[1,4]dioxino[2,3-f]quinazolin-10-yl)amino)phenyl)-3-isopropylurea,
1-(2-chloro-4-((5-methoxy-2,3-dihydro-[1,4]dioxino[2,3-f]quinazolin-10-yl)amino)phenyl)-3-(2-methoxypyridin-4-yl)urea,
1-(2-chloro-4-((5-methoxy-2,3-dihydro-[1,4]dioxino[2,3-f]quinazolin-10-yl)amino)phenyl)-3-(4-chloro-3-(trifluoromethyl)phenyl)urea,
1-(2-chloro-4-((5-methoxy-2,3-dihydro-[1,4]dioxino[2,3-f]quinazolin-10-yl)amino)phenyl)-3-(2-fluoro-4-(trifluoromethyl)phenyl)urea,
1-(2-chloro-4-((5-methoxy-2,3-dihydro-[1,4]dioxino[2,3-f]quinazolin-10-yl)amino)phenyl)-3-(4-(phenoxy)phenyl)urea,
1-(2-chloro-4-((5-methoxy-2,3-dihydro-[1,4]dioxino[2,3-f]quinazolin-10-yl)oxy)phenyl)-3-phenylurea,
1-(2-chloro-4-((5-methoxy-2,3-dihydro-[1,4]dioxino[2,3-f]quinazolin-10-yl)oxy)phenyl)-3-isopropylurea,
1-(2-chloro-4-((5-methoxy-2,3-dihydro-[1,4]dioxino[2,3-f]quinazolin-10-yl)oxy)phenyl)-3-(4-fluorophenyl)urea,
1-(2-chloro-4-((5-methoxy-2,3-dihydro-[1,4]dioxino[2,3-f]quinazolin-10-yl)amino)phenyl)-3-(3-methylsulfonylphenyl)urea,
1-(4-chloro-3-(trifluoromethyl)phenyl)-3-(4-((5-methoxy-2,3-dihydro-[1,4]dioxino[2,3-f]quinazolin-10-yl)oxy)phenyl)urea,
1-(4-chloro-3-(trifluoromethyl)phenyl)-3-(2-fluoro-4-((5-methoxy-2,3-dihydro-[1,4]dioxino[2,3-f]quinazolin-10-yl)oxy)phenyl)urea,
1-(2-fluoro-5-(trifluoromethyl)phenyl)-3-(4-((5-methoxy-2,3-dihydro-[1,4]dioxino[2,3-f]quinazolin-10-yl)oxy)phenyl)urea,
1-(2,4-difluorophenyl)-3-(2-fluoro-4-((5-methoxy-2,3-dihydro-[1,4]dioxino[2,3-f]quinazolin-10-yl)oxy)phenyl)urea,
1-(2-chloro-4-((5-methoxy-2,3-dihydro-[1,4]dioxino[2,3-f]quinazolin-10-yl)oxy)phenyl)-3-cyclopropylurea,
1-(4-((5-methoxy-2,3-dihydro-[1,4]dioxino[2,3-f]quinazolin-10-yl)oxy)phenyl)-3-(3-methoxyphenyl)urea,
1-(3-chloro-4-((5-methoxy-2,3-dihydro-[1,4]dioxino[2,3-f]quinazolin-10-yl)oxy)phenyl)-3-(3-methoxyphenyl)urea,
1-(4-((5-methoxy-2,3-dihydro-[1,4]dioxino[2,3-f]quinazolin-10-yl)oxy)phenyl)-3-(2-methoxypyridin-4-yl)urea,
1-(3-chloro-4-((5-methoxy-2,3-dihydro-[1,4]dioxino[2,3-f]quinazolin-10-yl)oxy)phenyl)-3-(2-methoxypyridin-4-yl)urea, 1-(2-chloro-4-((5-methoxy-2,3-dihydro-[1,4]dioxino[2,3-f]quinazolin-10-yl)amino)phenyl)-3-cyclobutylurea, 1-(2-chloro-4-((5-methoxy-2,3-dihydro-[1,4]dioxino[2,3-f]quinazolin-10-yl)amino)phenyl)-3-cyclopentylurea, 1-(2-chloro-4-((5-methoxy-2,3-dihydro-[1,4]dioxino[2,3-f]quinazolin-10-yl)amino)phenyl)-3-cyclohexylurea, 1-(2-chloro-4-((5-methoxy-2,3-dihydro-[1,4]dioxino[2,3-f]quinazolin-10-yl)amino)phenyl)-3-isopentylurea, 1-(4-((5-(3-morpholinopropyloxy)-2,3-dihydro-[1,4]dioxino[2,3-f]quinazolin-10-yl)oxy)phenyl)-3-(naphthalen-1-yl)urea, 1-(2-chloro-4-((5-methoxy-2,3-dihydro-[1,4]dioxino[2,3-f]quinazolin-10-yl)oxy)phenyl)-3-cyclopentylurea, 1-(2-chloro-4-((5-methoxy-2,3-dihydro-[1,4]dioxino[2,3-f]quinazolin-10-yl)oxy)phenyl)-3-cyclohexylurea, 1-(2-chloro-4-((5-(2-methoxyethoxy)-2,3-dihydro-[1,4]dioxino[2,3-f]quinazolin-10-yl)amino)phenyl)-3-cyclopropylurea, 1-(2-chloro-4-((5-(2-methoxyethoxy)-2,3-dihydro-[1,4]dioxino[2,3-f]quinazolin-10-yl)amino)phenyl)-3-(3-methoxyphenyl)urea, 1-(2-chloro-4-((5-(2-methoxyethoxy)-2,3-dihydro-[1,4]dioxino[2,3-f]quinazolin-10-yl)amino)phenyl)-3-(pyridin-2-yl)urea, 1-(2-chloro-4-((5-(2-methoxyethoxy)-2,3-dihydro-[1,4]dioxino[2,3-f]quinazolin-10-yl)amino)phenyl)-3-phenylurea, 1-(2-chloro-4-((5-(2-methoxyethoxy)-2,3-dihydro-[1,4]dioxino[2,3-f]quinazolin-10-yl)amino)phenyl)-3-(4-fluorophenyl)urea, 1-(2-chloro-4-((5-(2-methoxyethoxy)-2,3-dihydro-[1,4]dioxino[2,3-f]quinazolin-10-yl)amino)phenyl)-3-(3-methylisoxazol-5-yl)urea, 1-(2-chloro-4-((5-(2-methoxyethoxy)-2,3-dihydro-[1,4]dioxino[2,3-f]quinazolin-10-yl)amino)phenyl)-3-isopropylurea, 1-(2-chloro-4-((5-(2-methoxyethoxy)-2,3-dihydro-[1,4]dioxino[2,3-f]quinazolin-10-yl)amino)phenyl)-3-(2-methoxypyridin-4-yl)urea, 1-(2-chloro-4-((5-(2-methoxyethoxy)-2,3-dihydro-[1,4]dioxino[2,3-f]quinazolin-10-yl)amino)phenyl)-3-(4-chloro-3-(trifluoromethyl)phenyl)urea, 1-(2-chloro-4-((5-(2-methoxyethoxy)-2,3-dihydro-[1,4]dioxino[2,3-f]quinazolin-10-yl)amino)phenyl)-3-(2-fluoro-4-(trifluoromethyl)phenyl)urea, 1-(2-chloro-4-((5-(2-methoxyethoxy)-2,3-dihydro-[1,4]dioxino[2,3-f]quinazolin-10-yl)amino)phenyl)-3-(4-(phenoxy)phenyl)urea, 1-(2-chloro-4-((5-(2-methoxyethoxy)-2,3-dihydro-[1,4]dioxino[2,3-f]quinazolin-10-yl)oxy)phenyl)-3-cyclopropylurea, 1-(4-chloro-3-(trifluoromethyl)phenyl)-3-(4-((5-(2-methoxyethoxy)-2,3-dihydro-[1,4]dioxino[2,3-f]quinazolin-10-yl)oxy)phenyl)urea, 1-(2-fluoro-5-(trifluoromethyl)phenyl)-3-(4-((5-(2-methoxyethoxy)-2,3-dihydro-[1,4]dioxino[2,3-f]quinazolin-10-yl)oxy)phenyl)urea, 1-(4-chloro-3-(trifluoromethyl)phenyl)-3-(2-fluoro-4-((5-(2-methoxyethoxy)-2,3-dihydro-[1,4]dioxino[2,3-f]quinazolin-10-yl)oxy)phenyl)urea, 1-(2,4-difluorophenyl)-3-(2-fluoro-4-((5-(2-methoxyethoxy)-2,3-dihydro-[1,4]dioxino[2,3-f]quinazolin-10-yl)oxy)phenyl)urea, 1-(4-((5-(2-methoxyethoxy)-2,3-dihydro-[1,4]dioxino[2,3-f]quinazolin-10-yl)oxy)phenyl)-3-(3-methoxyphenyl)urea, 1-(3-chloro-4-((5-(2-methoxyethoxy)-2,3-dihydro-[1,4]dioxino[2,3-f]quinazolin-10-yl)oxy)phenyl)-3-(3-methoxyphenyl)urea, 1-(4-((5-(2-methoxyethoxy)-2,3-dihydro-[1,4]dioxino[2,3-f]quinazolin-10-yl)oxy)phenyl)-3-(2-methoxypyridin-4-yl)urea, 1-(3-chloro-4-((5-(2-methoxyethoxy)-2,3-dihydro-[1,4]dioxino[2,3-f]quinazolin-10-yl)oxy)phenyl)-3-(2-methoxypyridin-4-yl)urea, 1-(2-chloro-4-((5-(2-methoxyethoxy)-2,3-dihydro-[1,4]dioxino[2,3-f]quinazolin-10-yl)oxy)phenyl)-3-cyclobutylurea, 1-(2-chloro-4-((5-(2-methoxyethoxy)-2,3-dihydro-[1,4]dioxino[2,3-f]quinazolin-10-yl)oxy)phenyl)-3-cyclopentylurea, 1-(2-chloro-4-((5-(2-methoxyethoxy)-2,3-dihydro-[1,4]dioxino[2,3-f]quinazolin-10-yl)oxy)phenyl)-3-cyclohexylurea, 1-(2-fluoro-4-((5-(2-methoxyethoxy)-2,3-dihydro-[1,4]dioxino[2,3-f]quinazolin-10-yl)oxy)phenyl)-3-(2-fluoro-5-(trifluoromethyl)phenyl)urea, 1-(3-fluoro-4-((5-(2-methoxyethoxy)-2,3-dihydro-[1,4]dioxino[2,3-f]quinazolin-10-yl)oxy)phenyl)-3-(2-fluoro-5-(trifluoromethyl)phenyl)urea, 1-(4-chloro-3-(trifluoromethyl)phenyl)-3-(3-fluoro-4-((5-(2-methoxyethoxy)-2,3-dihydro-[1,4]dioxino[2,3-f]quinazolin-10-yl)oxy)phenyl)urea, 1-(4-chloro-3-(trifluoromethyl)phenyl)-3-(6-((5-(2-methoxyethoxy)-2,3-dihydro-[1,4]dioxino[2,3-f]quinazolin-10-yl)oxy)pyridin-3-yl)urea, 1-(2-chloro-4-((5-(3-(pyrrolidin-1-yl)propoxy)-2,3-dihydro-[1,4]dioxino[2,3-f]quinazolin-10-yl)amino)phenyl)-3-cyclopropylurea, 1-(2-chloro-4-((5-(3-(pyrrolidin-1-yl)propoxy)-2,3-dihydro-[1,4]dioxino[2,3-f]quinazolin-10-yl)oxy)phenyl)-3-cyclopropylurea, 1-(2-chloro-4-((5-(3-(morpholinopropyloxy)-2,3-dihydro-[1,4]dioxino[2,3-f]quinazolin-10-yl)amino)phenyl)-3-cyclopropylurea, 1-(2-chloro-4-((5-(3-(morpholinopropyloxy)-2,3-dihydro-[1,4]dioxino[2,3-f]quinazolin-10-yl)oxy)phenyl)-3-cyclopropylurea, 1-(2-fluoro-5-(trifluoromethyl)phenyl)-3-(4-((5-(3-morpholinopropoxy)-2,3-dihydro-[1,4]dioxino[2,3-f]quinazolin-10-yl)oxy)phenyl)urea, 1-(4-chloro-3-(trifluoromethyl)phenyl)-3-(4-((5-(3-morpholinopropoxy)-2,3-dihydro-[1,4]dioxino[2,3-f]quinazolin-10-yl)oxy)phenyl)urea, 1-(3-fluoro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea, 1-(4-chloro-3-(trifluoromethyl)phenyl)-3-(3-fluoro-4-((5-(3-morpholinopropoxy)-2,3-dihydro-[1,4]dioxino[2,3-f]quinazolin-10-yl)oxy)phenyl)urea, 1-(4-chloro-3-(trifluoromethyl)phenyl)-3-(2-fluoro-4-((5-(3-morpholinopropoxy)-2,3-dihydro-[1,4]dioxino[2,3-f]quinazolin-10-yl)oxy)phenyl)urea, 1-(2-fluoro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea, 1-(2-chloro-4-((5-(3-morpholinopropoxy)-2,3-dihydro-[1,4]dioxino[2,3-f]quinazolin-10-yl)oxy)phenyl)-3-(2-fluoro-5-(trifluoromethyl)phenyl)urea, 1-(4-chloro-3-(trifluoromethyl)phenyl)-3-(4-((5-(2-morpholinoethoxy)-2,3-dihydro-[1,4]dioxino[2,3-f]quinazolin-10-yl)oxy)phenyl)urea, 1-(2-fluoro-5-(trifluoromethyl)phenyl)-3-(4-((5-(3-morpholinoethoxy)-2,3-dihydro-[1,4]dioxino[2,3-f]quinazolin-10-yl)oxy)phenyl)urea, 1-(3-chloro-4-fluorophenyl)-3-(4-((5-(3-morpholinopropoxy)-2,3-dihydro-[1,4]dioxino[2,3-f]quinazolin-10-yl)oxy)phenyl)urea, 1-(4-fluoro-3-(trifluoromethyl)phenyl)-3-(4-((5-(3-morpholinopropoxy)-2,3-dihydro-[1,4]dioxino[2,3-f]quinazolin-10-yl)oxy)phenyl)urea, 1-(2-fluoro-5-(trifluoromethyl)phenyl)-3-(4-((5-(2-(tetrahydropyrrol-1-yl)ethoxy)-2,3-dihydro-[1,4]dioxino[2,3-f]quinazolin-10-yl)oxy)phenyl)urea, 1-(4-((5-ethoxy-2,3-dihydro-[1,4]dioxino[2,3-f]quinazolin-10-yl)oxy)phenyl)-3-(2-fluoro-5-(trifluoromethyl)phenyl)urea, 1-(4-((5-isopropoxy-2,3-dihydro-[1,4]dioxino[2,3-f]quinazolin-10-yl)oxy)phenyl)-3-(2-fluoro-5-(trifluoromethyl)phenyl)urea, 1-(2-fluoro-5-(trifluoromethyl)phenyl)-3-(4-((5-((tetrahydro-2H-pyran-4-yl)oxy)-2,3-dihydro-[1,4]dioxino[2,3-f]quinazolin-10-yl)oxy)phenyl)urea, 1-(2-fluoro-5-(trifluoromethyl)phenyl)-3-(4-((5-((tetrahydrofuran-3-yl)oxy)-2,3-dihydro-[1,4]dioxino[2,3-f]quinazolin-10-yl)oxy)phenyl)urea, 1-(4-((5-(3-(1,1-dioxidothiomorpholino)propoxy)-2,3-dihydro-[1,4]dioxino[2,3-f]quinazolin-10-yl)oxy)phenyl)-3-(2-fluoro-5-(trifluoromethyl)phenyl)urea, 1-(2-chloro-4-((5-(3-(dimethylamino)propoxy)-2,3-dihydro-[1,4]dioxino[2,3-f]quinazolin-10-yl)amino)phenyl)-3-cyclopropylurea, 1-(2-chloro-4-((5-(2-(1-methylpiperazin-4-yl)ethoxy)-2,3-dihydro-[1,4]dioxino[2,3-f]quinazolin-10-yl)amino)phenyl)-3-cyclopropylurea, 1-(2-chloro-4-((5-(2-methylthioethoxy)-2,3-dihydro-[1,4]dioxino[2,3-f]quinazolin-10-yl)amino)phenyl)-3-cyclopropylurea, 1-(2-chloro-4-(((5-(2-methylthio)ethoxy)-2,3-dihydro-[1,4]dioxino[2,3-f]quinazolin-10-yl)oxy)phenyl)-3-cyclopropylurea, 1-(2-chloro-4-(((5-(3-methoxy)propoxy)-2,3-dihydro-[1,4]dioxino[2,3-f]quinazolin-10-yl)oxy)phenyl)-3-cyclopropylurea, 1-(2-chloro-4-((5-(2-dimethylamino)ethoxy)-2,3-dihydro-[1,4]dioxino[2,3-f]quinazolin-10-yl)amino)phenyl)-3-cyclopropylurea, 1-(2-chloro-4-((5-(6-methoxy)hexyloxy)-2,3-dihydro-[1,4]dioxino[2,3-f]quinazolin-10-yl)oxy)phenyl)-3-cyclopropylurea, 1-(2-fluoro-5-chlorophenyl)-3-(4-((5-(3-morpholinopropoxy)-2,3-dihydro-[1,4]dioxino[2,3-f]quinazolin-10-yl)oxy)phenyl)urea, and 1-(2-fluoro-5-(trifluoromethyl)phenyl)-3-(4-((5-(3-morpholinopropoxy)-2,3-dihydro-[1,4]dioxino[2,3-f]quinazolin-10-yl)oxy)phenyl)urea L-malate.

17. The compound, or the pharmaceutically acceptable salt, enantiomer, stereoisomer, hydrate, or solvate thereof according to claim 1, wherein the said compound is selected from the group consisting of:

1-(2-chloro-4-((5-methoxy-2,3-dihydro-[1,4]dioxino[2,3-f]quinazolin-10-yl)amino)phenyl)-3-(4-chloro-3-(trifluoromethyl)phenyl)urea, 1-(4-chloro-3-(trifluoromethyl)phenyl)-3-(4-((5-methoxy-2,3-dihydro-[1,4]dioxino[2,3-f]quinazolin-10-yl)oxy)phenyl)urea, 1-(4-chloro-3-(trifluoromethyl)phenyl)-3-(2-fluoro-4-((5-methoxy-2,3-dihydro-[1,4]dioxino[2,3-f]quinazolin-10-yl)oxy)phenyl)urea, 1-(2-chloro-4-((5-(2-methoxyethoxy)-2,3-dihydro-[1,4]dioxino[2,3-f]quinazolin-10-yl)amino)phenyl)-3-(4-chloro-3-(trifluoromethyl)phenyl)urea, 1-(4-chloro-3-(trifluoromethyl)phenyl)-3-(4-((5-(2-methoxyethoxy)-2,3-dihydro-[1,4]dioxino[2,3-f]quinazolin-10-yl)oxy)phenyl)urea, 1-(4-chloro-3-(trifluoromethyl)phenyl)-3-(2-fluoro-4-((5-(2-methoxyethoxy)-2,3-dihydro-[1,4]dioxino[2,3-f]quinazolin-10-yl)oxy)phenyl)urea, 1-(4-chloro-3-(trifluoromethyl)phenyl)-3-(3-fluoro-4-((5-(2-methoxyethoxy)-2,3-dihydro-[1,4]dioxino[2,3-f]quinazolin-10-yl)oxy)phenyl)urea, 1-(4-chloro-3-(trifluoromethyl)phenyl)-3-(6-((5-(2-methoxyethoxy)-2,3-dihydro-[1,4]dioxino[2,3-f]quinazolin-10-yl)oxy)pyridin-3-yl)urea, 1-(4-chloro-3-(trifluoromethyl)phenyl)-3-(4-((5-(3-morpholinopropoxy)-2,3-dihydro-[1,4]dioxino[2,3-f]quinazolin-10-yl)oxy)phenyl)urea, 1-(4-chloro-3-(trifluoromethyl)phenyl)-3-(3-fluoro-4-((5-(3-morpholinopropoxy)-2,3-dihydro-[1,4]dioxino[2,3-f]quinazolin-10-yl)oxy)phenyl)urea, 1-(4-chloro-3-(trifluoromethyl)phenyl)-3-(2-fluoro-4-((5-(3-morpholinopropoxy)-2,3-dihydro-[1,4]dioxino[2,3-f]quinazolin-10-yl)oxy)phenyl)urea, and 1-(4-chloro-3-(trifluoromethyl)phenyl)-3-(4-((5-(2-morpholinoethoxy)-2,3-dihydro-[1,4]dioxino[2,3-f]quinazolin-10-yl)oxy)phenyl)urea.

18. The compound according to claim 16 having the following structure:

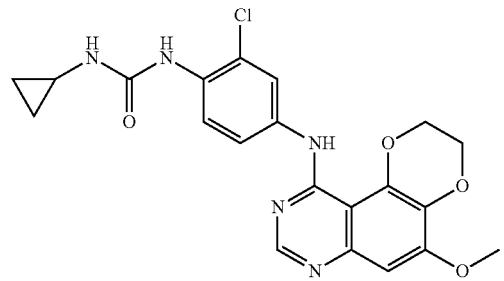 [SMILES: COc1cc2ncnc(Nc3ccc(NC(=O)NC4CC4)c(Cl)c3)c2c2c1OCCO2]

or the pharmaceutically acceptable salt thereof.

19. The compound according to claim 16 having the following structure:

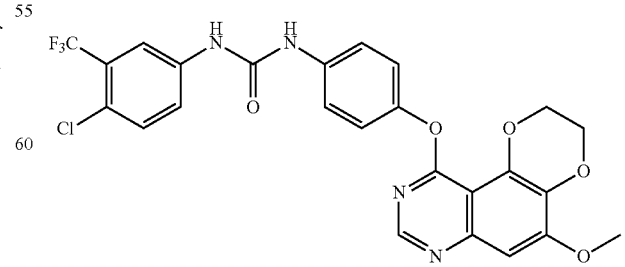

or the pharmaceutically acceptable salt thereof.

20. The compound according to claim 16 having the following structure:
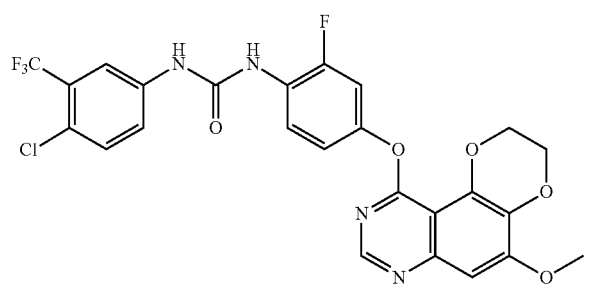 [SMILES: COc1cc2ncnc(Oc3ccc(NC(=O)Nc4ccc(Cl)c(C(F)(F)F)c4)c(F)c3)c2c2c1OCCO2]
or the pharmaceutically acceptable salt thereof.
21. The compound according to claim 16 having the following structure:
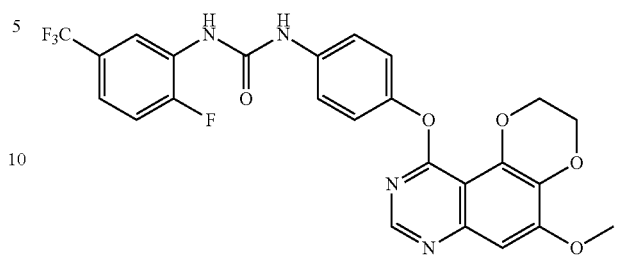
or the pharmaceutically acceptable salt thereof.
* * * * *